US006369252B1

(12) United States Patent
Akoh

(10) Patent No.: US 6,369,252 B1
(45) Date of Patent: Apr. 9, 2002

(54) STRUCTURED LIPIDS

(75) Inventor: Casimir C. Akoh, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/255,749

(22) Filed: Feb. 23, 1999

Related U.S. Application Data

(60) Provisional application No. 60/076,167, filed on Feb. 26, 1998.

(51) Int. Cl.[7] ............................................... C07C 57/00
(52) U.S. Cl. ...................................... 554/227; 435/135
(58) Field of Search .......................... 554/227; 435/135

(56) References Cited

U.S. PATENT DOCUMENTS

| | | | |
|---|---|---|---|
| 4,906,664 A | | 3/1990 | Bistrian et al. .............. 514/552 |
| 5,204,251 A | * | 4/1993 | Kyotani et al. .............. 435/134 |
| 5,312,836 A | | 5/1994 | Bistrian ....................... 554/224 |
| 5,571,553 A | | 11/1996 | Stein .......................... 426/607 |
| 5,661,180 A | | 8/1997 | DeMichele et al. ......... 514/547 |

OTHER PUBLICATIONS

Chem. Abstr. of 5,204,251 Showing Compound, 1993.*
Lee et al, JAOCS, vol. 74, No. 5, pp. 579–584, 1997.*
Lee et al., JAOCS, vol. 73, No. 5, pp. 611–615, 1996.*
Akoh et al., JAOCS, vol. 74, No. 11, pp. 1409–1413, 1997.*
Fomuso et al., JAOCS, vol. 74, No. 3, pp. 269–272, 1997.*
Akoh et al., "Enzymatic Synthesis of Structured Lipids: Transesterification of Triolein and Caprylic Acid,", *Journal of Food Lipids*, 2:219–230 (1995).
Akoh, "New Developments on Low Calorie Fats and Oils Substitutes," *Journal of Food Lipids*, 3:223–232 (1996).
Akoh et al., "Enzymatic Modification of Trilinolein: Incorporation of n–3 Polyunsaturated Fatty Acids," *JAOCS*, 72(11):1317–1321 (1995).
Akoh, In: *Food Lipids and Health*, (eds. R.E. McDonald and D.B. Min). Marcel Dekker, New York, 117–138 (1996).
Akoh, "Structured Lipids–Enzymatic Approach," *Inform* 6(9):1055–1061 (1995).
Akoh et al., "Enzymatic Modification of Borage Oil: Incorporation of Eicosapentaenoic Acid," *Journal of Food Lipids* 2:231–238 (1995).
Akoh, "Making New Structured Fats by Chemical Reaction and Enyzmatic Modification," *Lipid Technology*, 61–66 (May 1997).
Akoh et al., "Enzymatic Synthesis of Position–Specific Low–Calorie Structured Lipids," *JAOCS* 74(11):1409–1413 (1997).
Akoh et al., "Lipase–Catalyzed Modification of Borage Oil: Incorporation of Capric and Eicosapentaenoic Acids to Form Structured Lipids," *JAOCS* 75(6):697–701 (1998).
Fomuso et al., "Enzymatic Modification of Triolein: Incorporation of Caproic and Butyric Acids to Produce Reduced- –Calorie Structured Lipids," *JAOCS* 74(3):269–272 (1997).

(List continued on next page.)

Primary Examiner—Deborah Carr
(74) Attorney, Agent, or Firm—Richard F. Trecartin, Esq.; Flehr Hohbach Test Albritton & Herbert LLP

(57) ABSTRACT

Described herein are novel structured lipids as well as novel mixtures comprising structured lipids. Also described herein are enzymatic methods of forming these structured lipids and mixtures comprising structured lipids. Also described herein are methods of modulating total cholesterol levels, low-density lipoprotein cholesterol, triacylglycerol levels, and/or the ratio of T-helper cells to T-cytotoxic cells in an individual comprising administrating a structured lipid mixture as provided herein. It is further an object to provide a method of modulating weight in an individual comprising administrating a structured lipid mixture as provided herein.

27 Claims, 16 Drawing Sheets

OTHER PUBLICATIONS

Fomuso et al., "Structured Lipids: Lipase–Catalyzed Interesterification of Tricaproin and Trilinolein," *JAOCS* 75(3):405–410 (1998).

Lee et al., "Effects of Selected Substrate Forms on the Synthesis of Structured Lipids by Two Immobilized Lipases," *JAOCS* 74(5):579–585 (1997).

Huang et al., "Optimization and Scale–Up of Enzymatic Synthesis of Structured Lipids Using RSM," *Journal of Food Science*, 61(1):137–141 (1996).

Huang et al., "Enzymatic Synthesis of Structured Lipids: Transesterification of Triolein and Caprylic Acid Ethyl Ester," *JAOCS*, 73(2):245–250 (1996).

Haumann, "Structured Lipids Allow Fat Tailoring," *INFORM*, 8(10):1004–1011 (Oct. 1997).

Lee et al., "Immobilized Lipase–Catalyzed Production of Structured Lipids with Eicosapentaenoic Acid at Specific Positions," *JAOCS*, 73(5):611–615 (1996).

Lee et al., "Characterization of Enzymatically Synthesized Structured Lipids Containing Eicosapentaenoic, Docosahexaenoic, and Caprylic Acids," *JAOCS* 75(4):495–499 (1998).

Shieh et al., "Four–Factor Response Surface Optimization of the Enzymatic Modification of Triolein to Structured Lipids," *JAOCS*, 72(6):619–623 (1995).

* cited by examiner

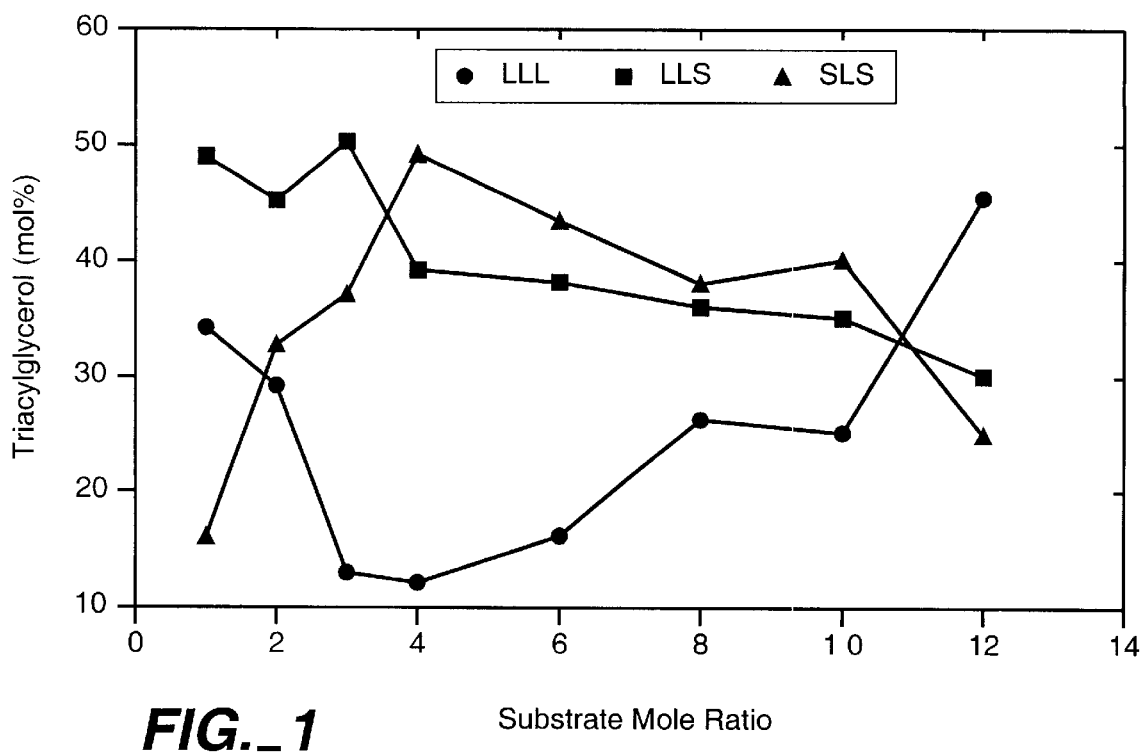
*FIG._1*
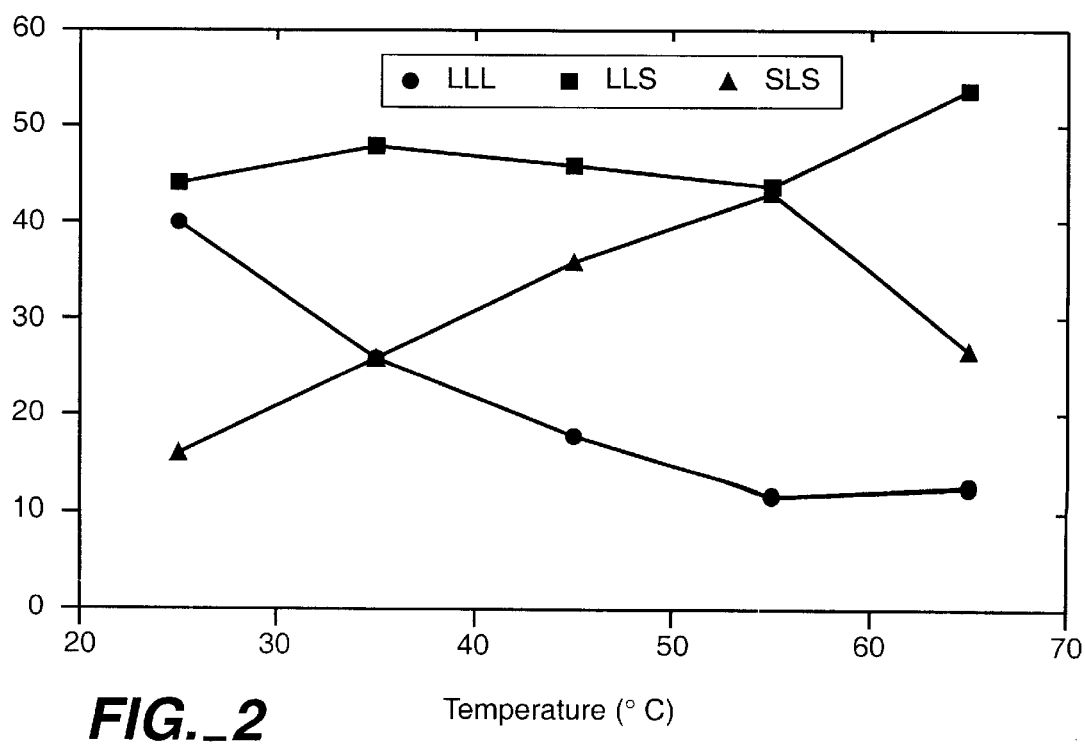
*FIG._2*

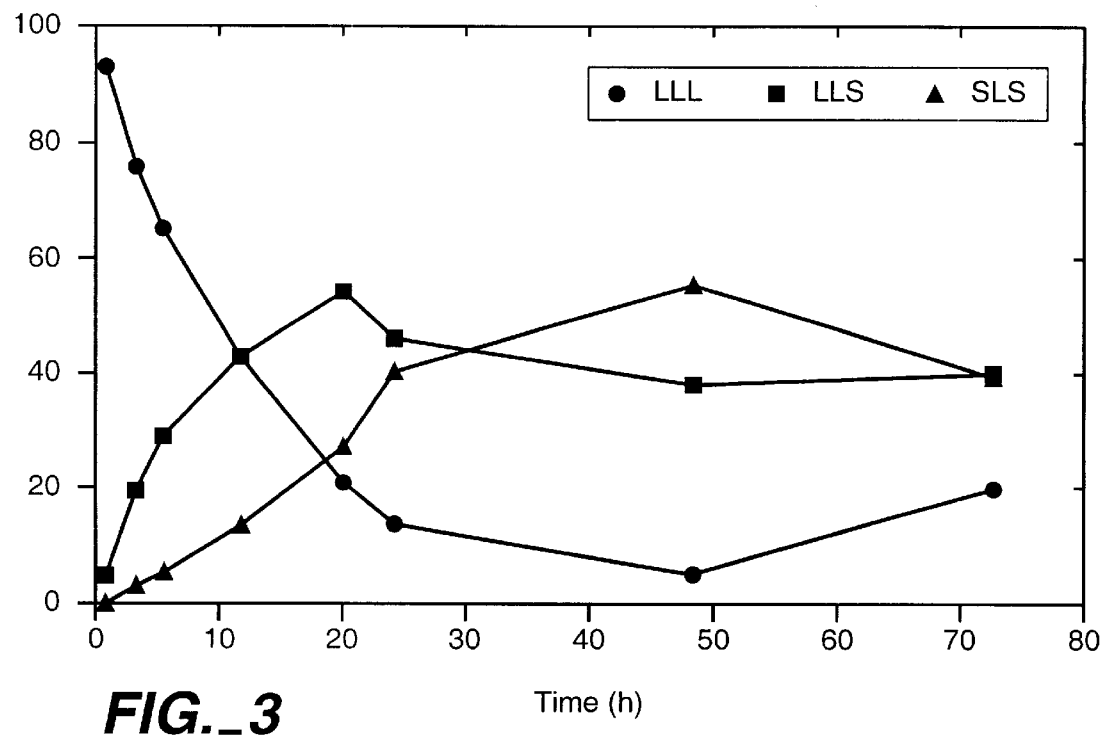
FIG._3
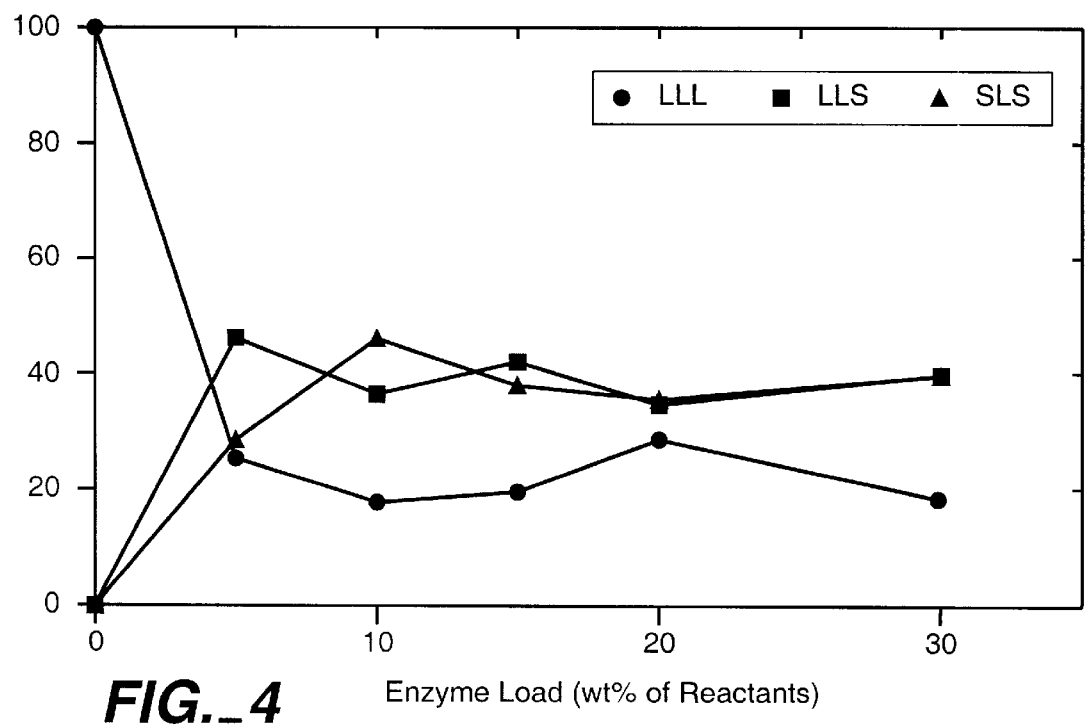
FIG._4

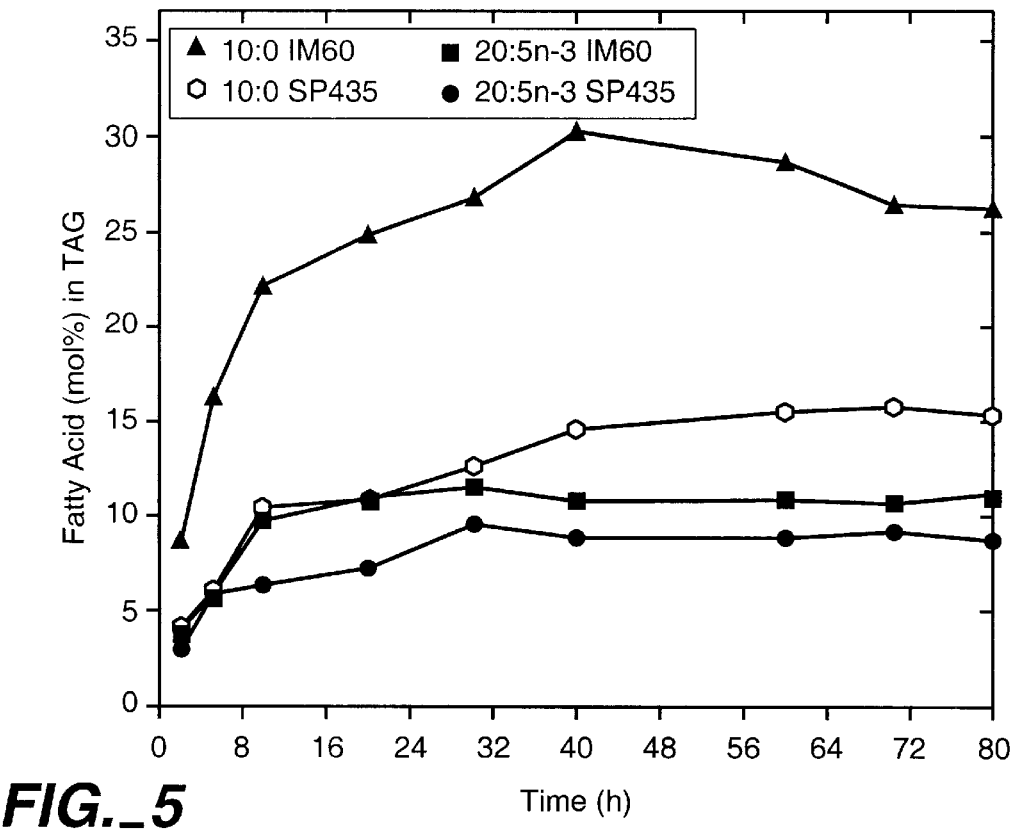
FIG._5
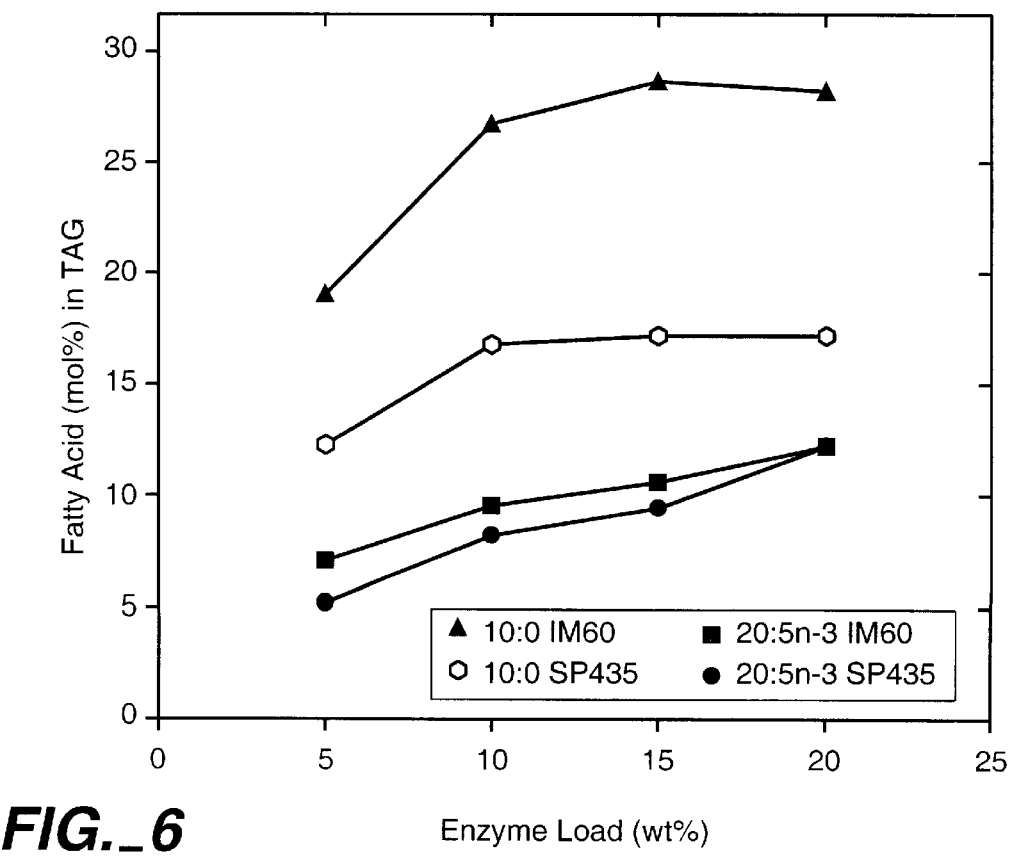
FIG._6

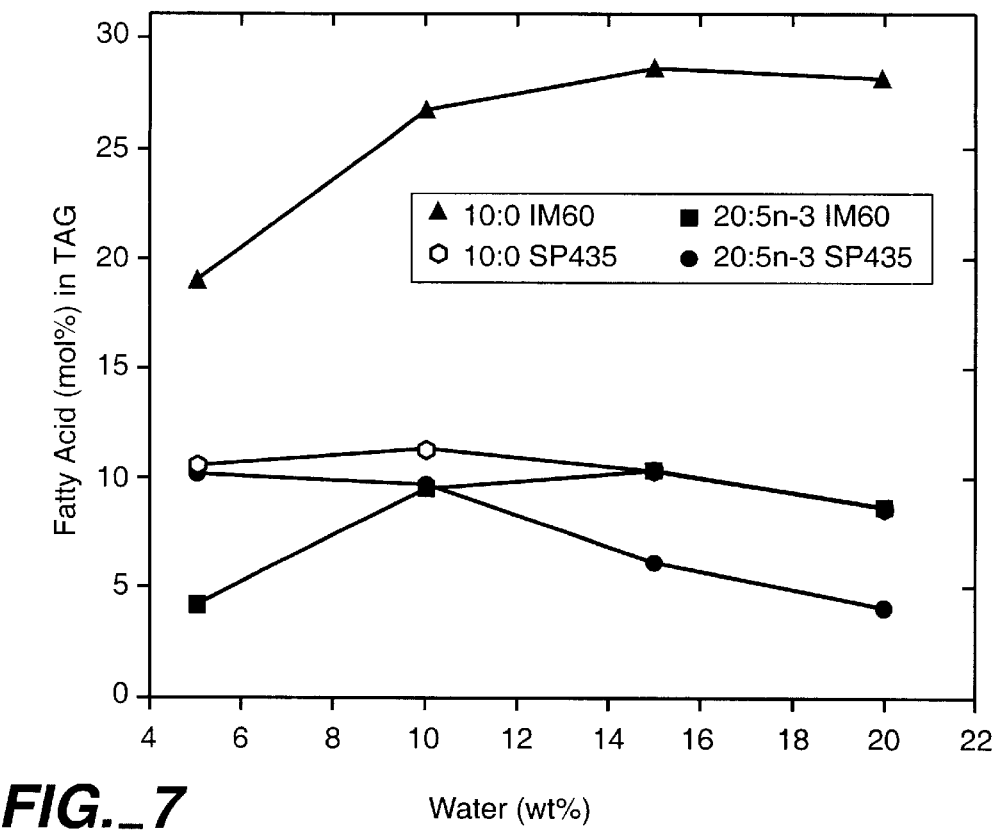
FIG._7
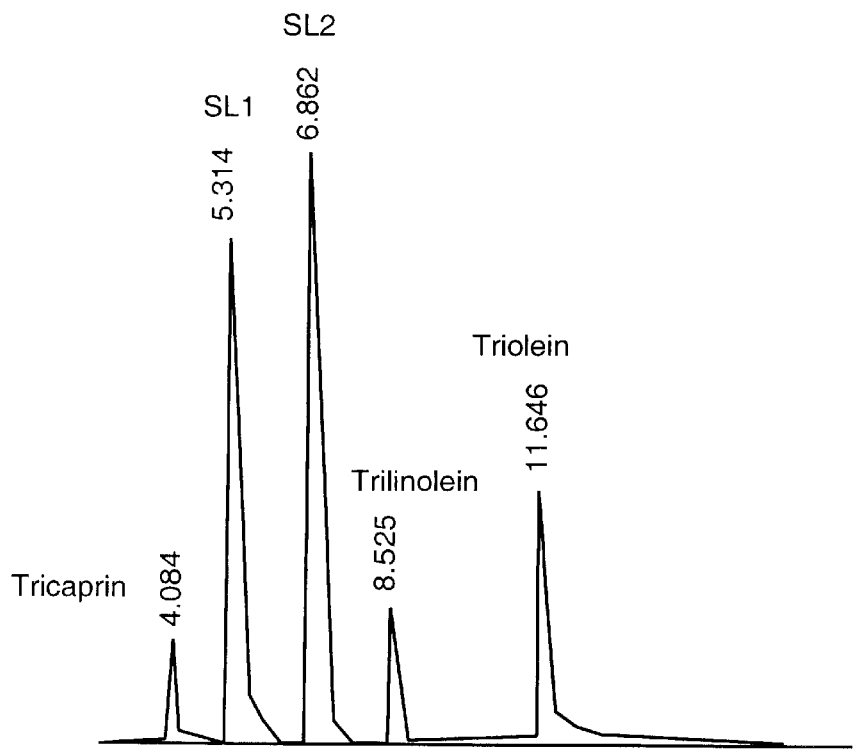
FIG._8

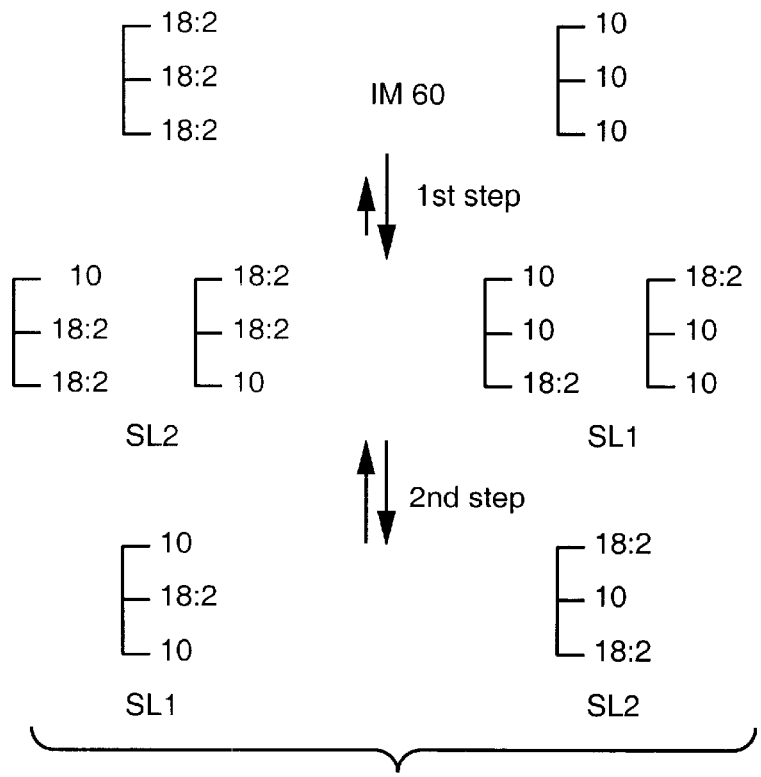
FIG._9A
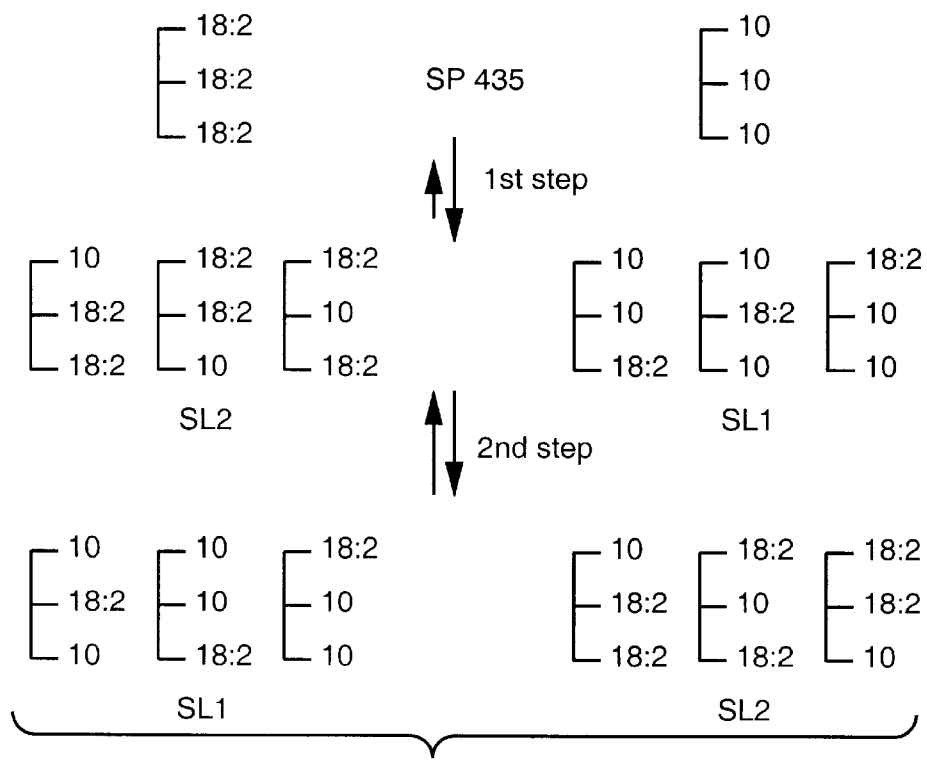
FIG._9B

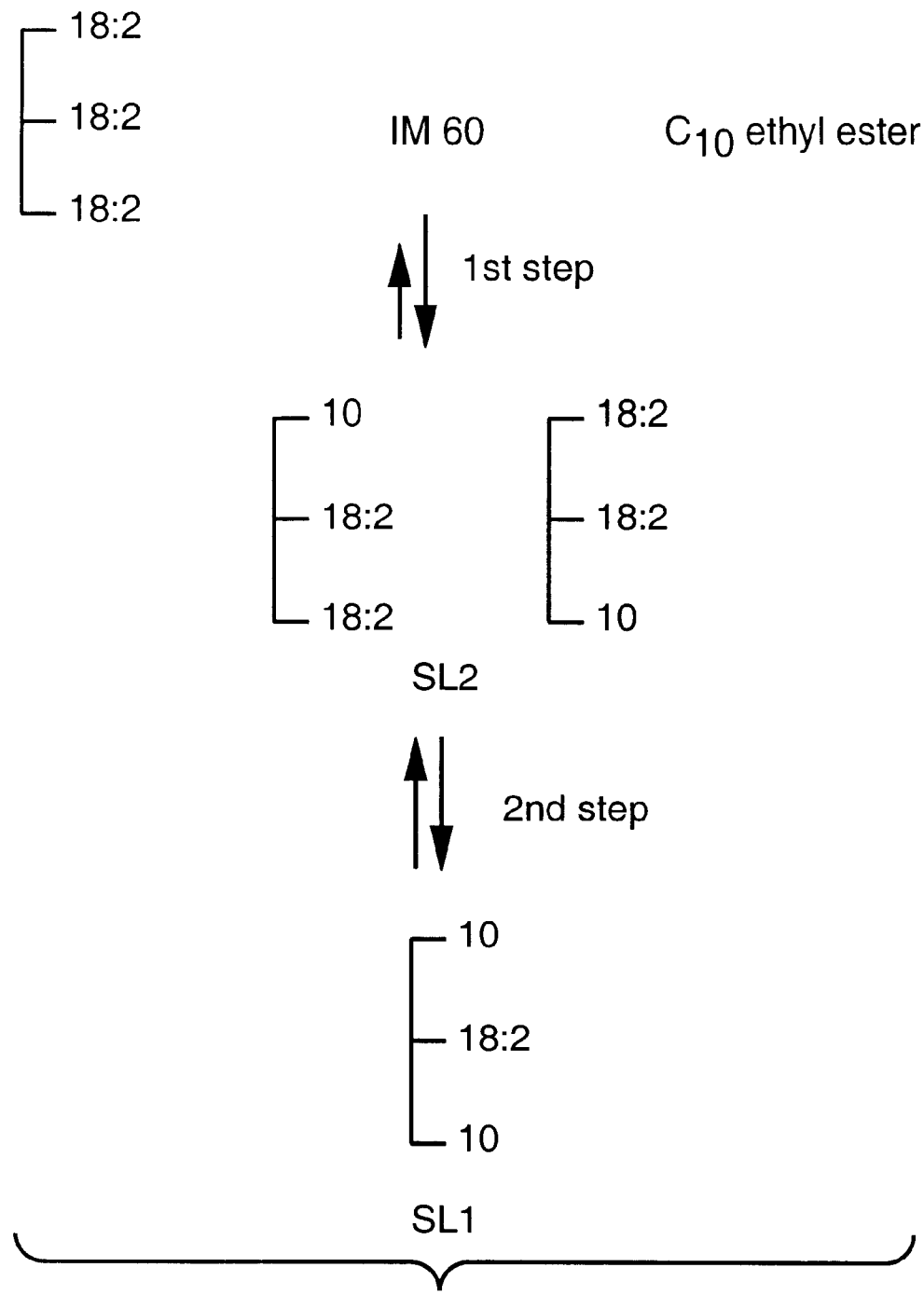
FIG. _10A

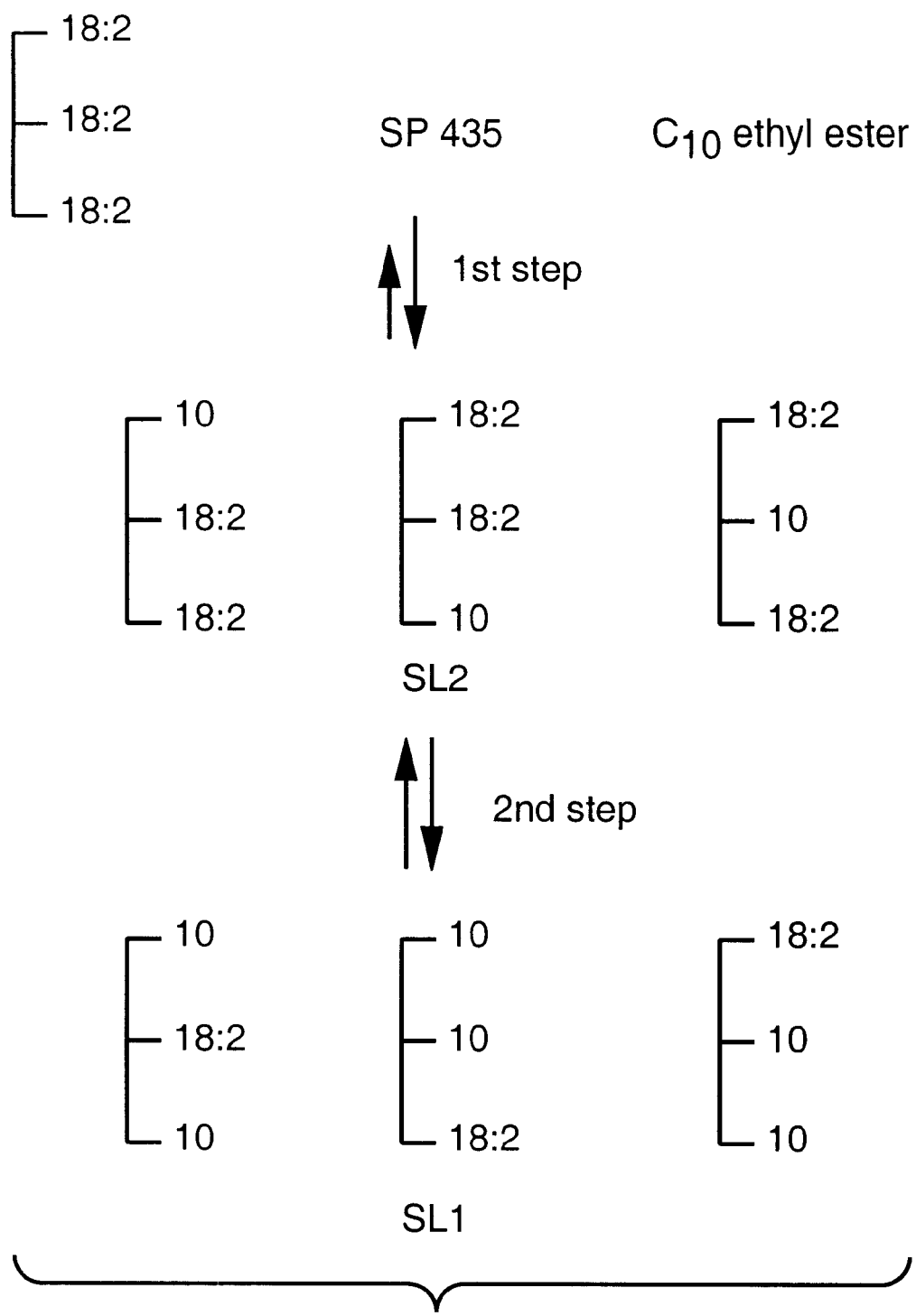
FIG._10B

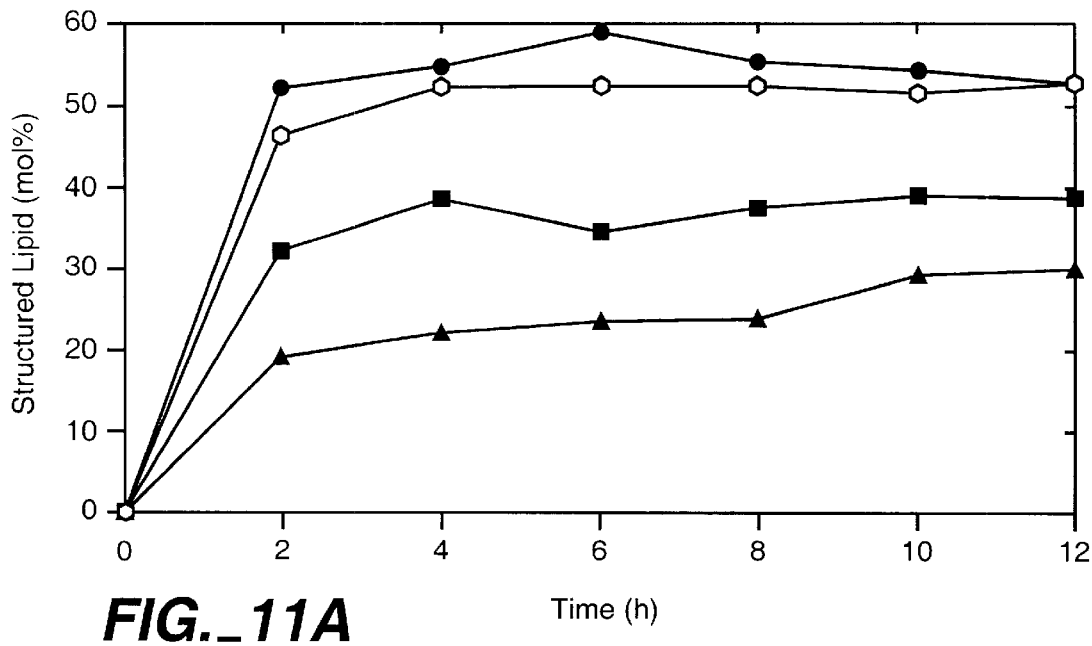
FIG._11A
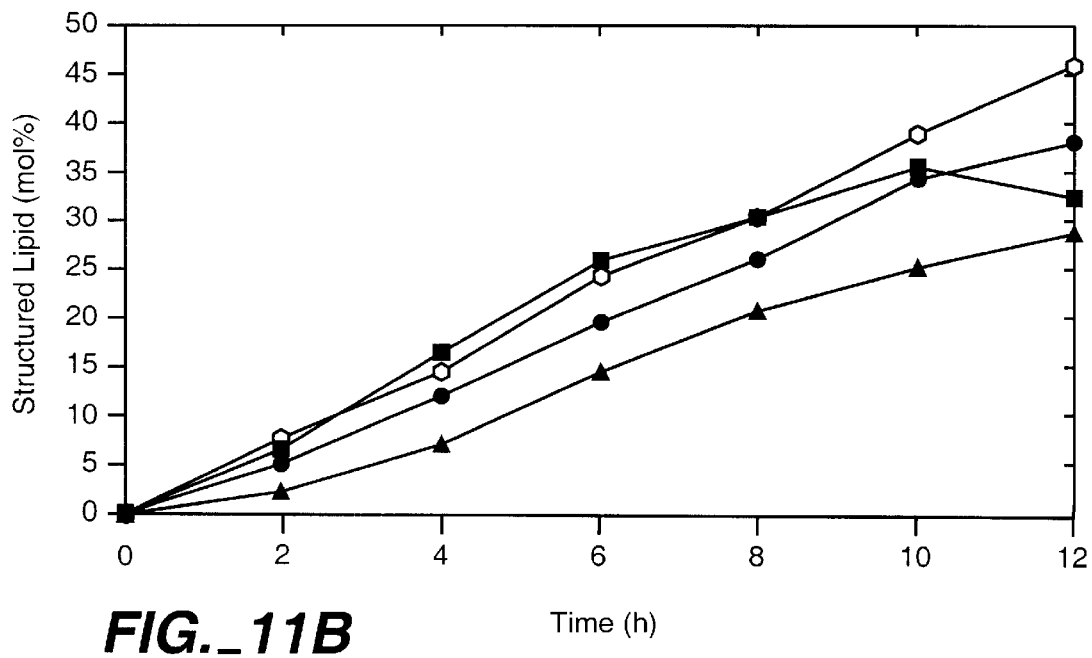
FIG._11B

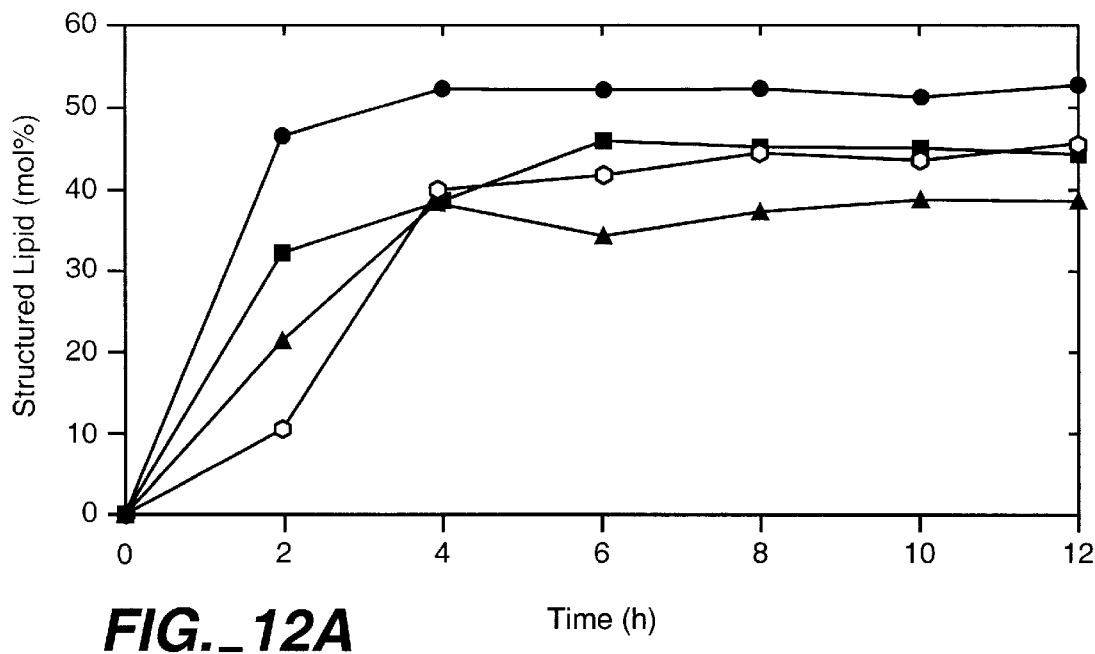
FIG._12A
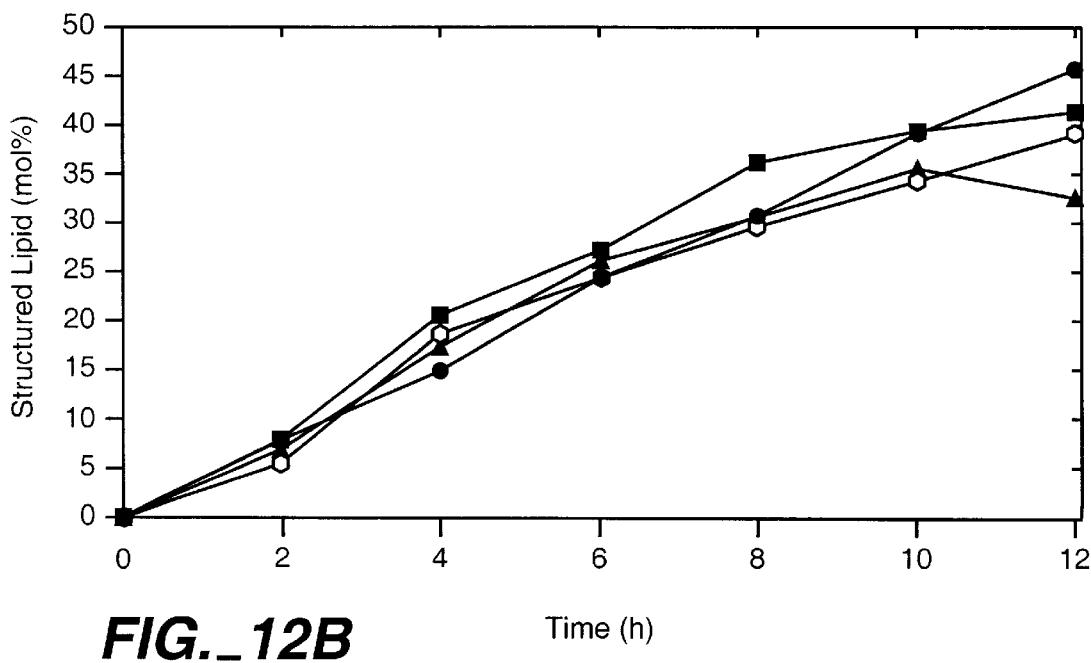
FIG._12B

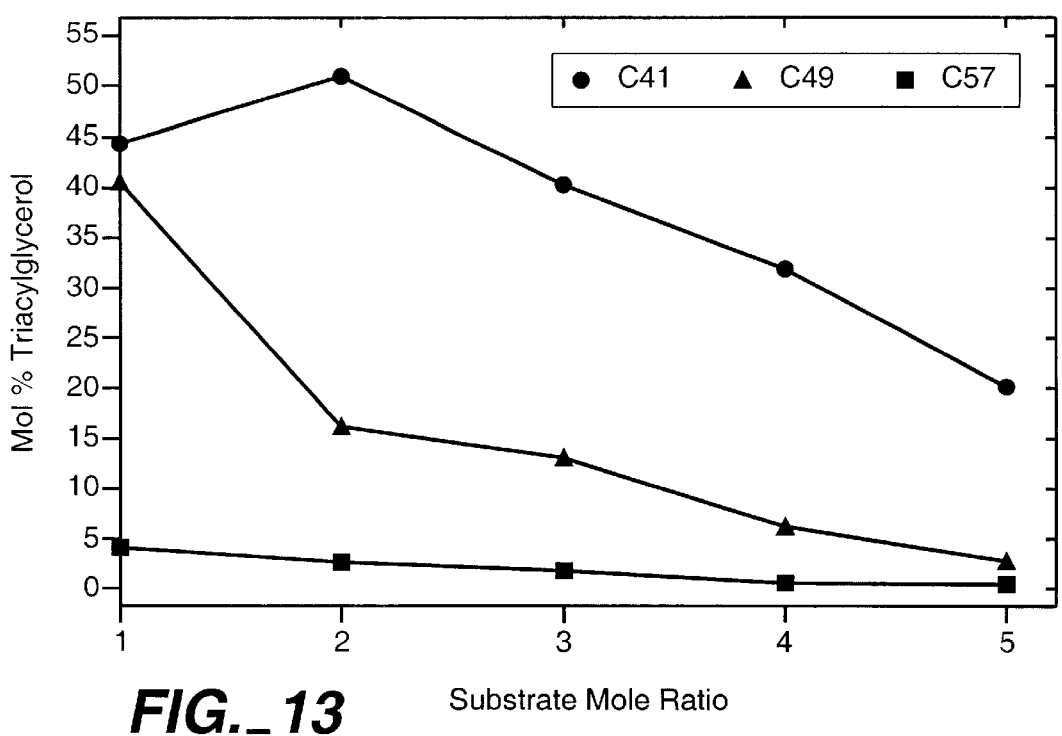
FIG._13
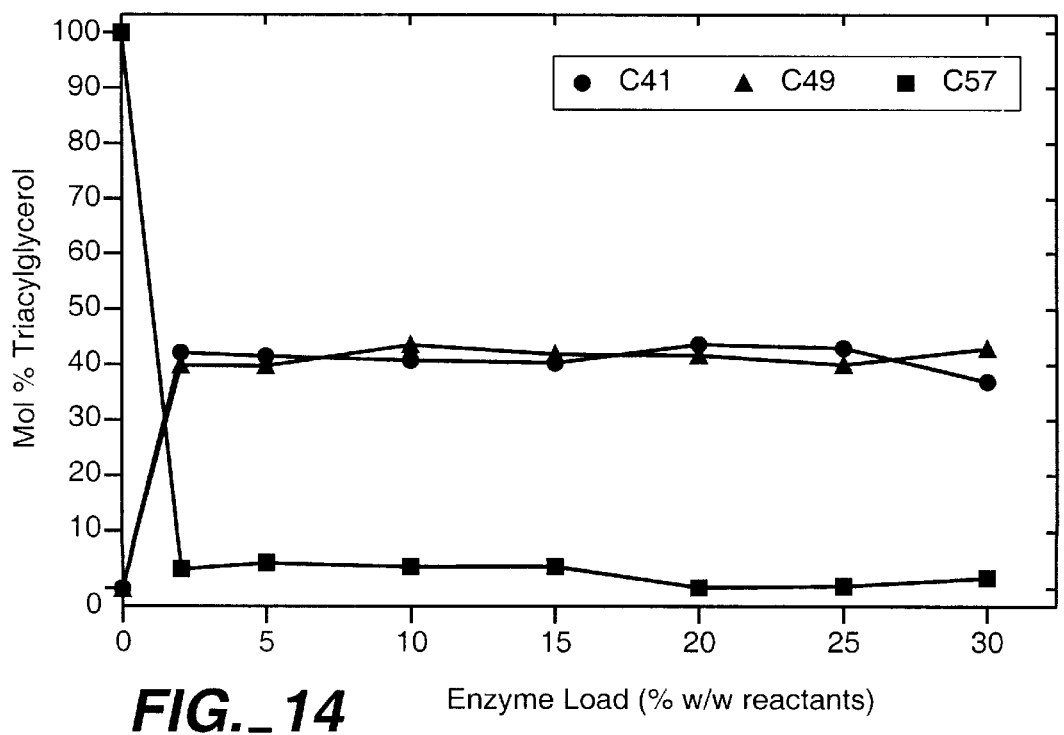
FIG._14

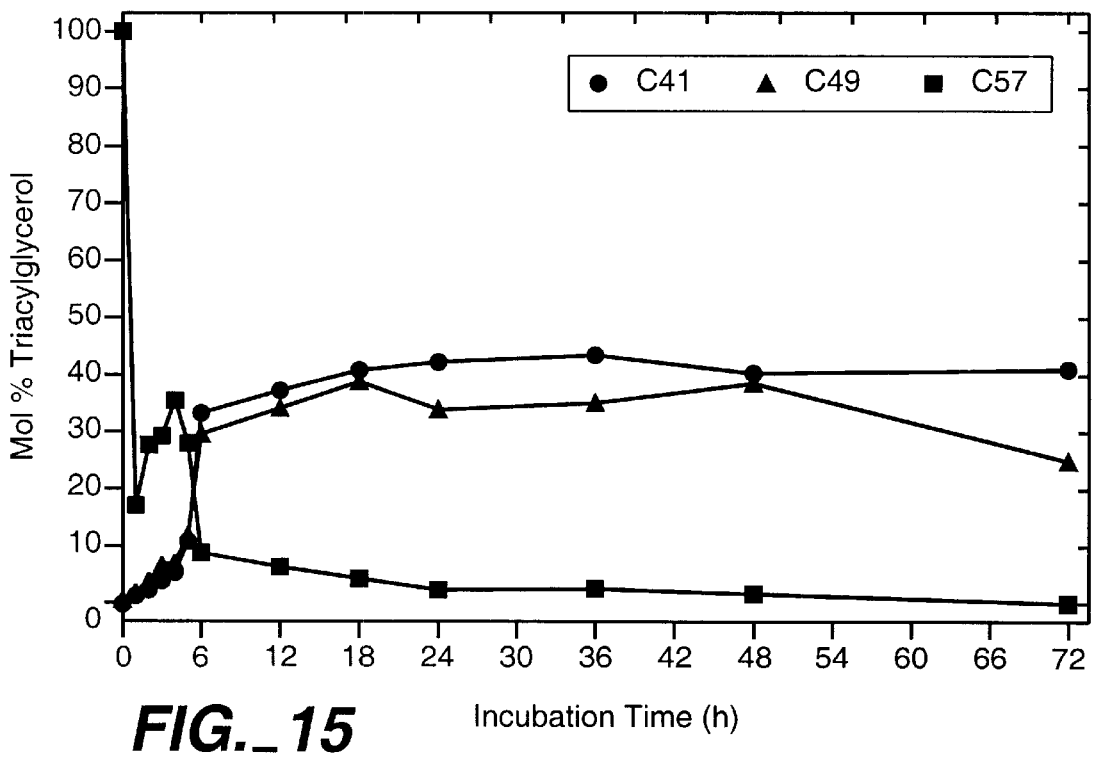
FIG._15
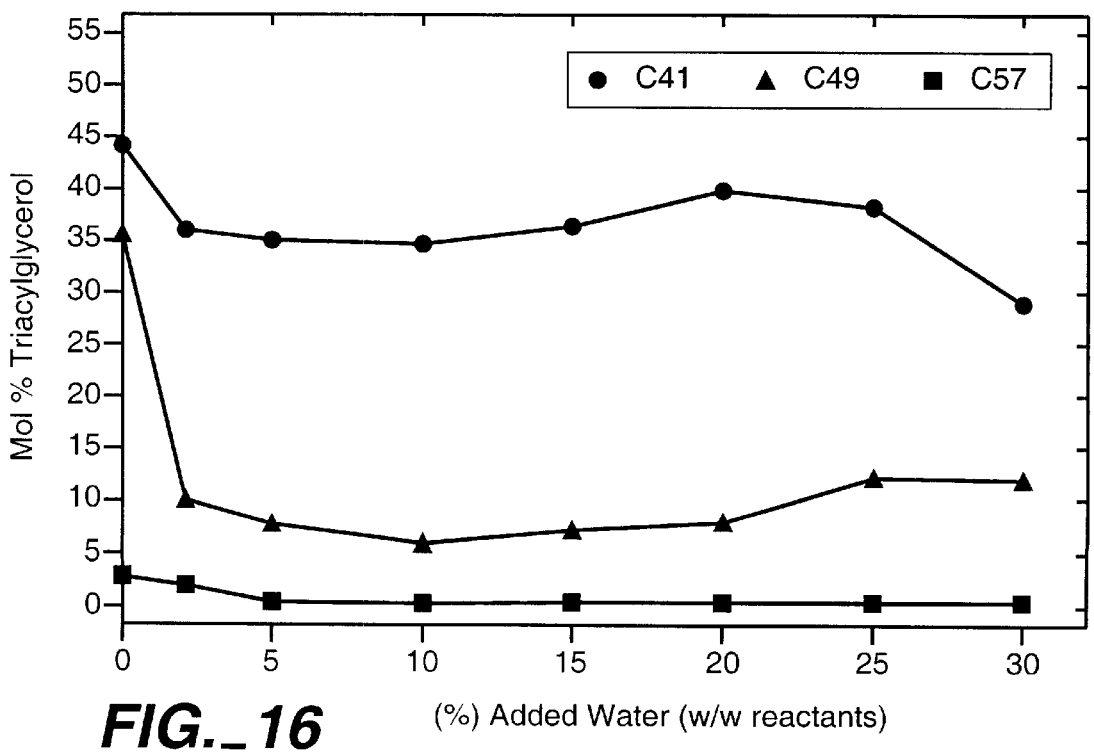
FIG._16

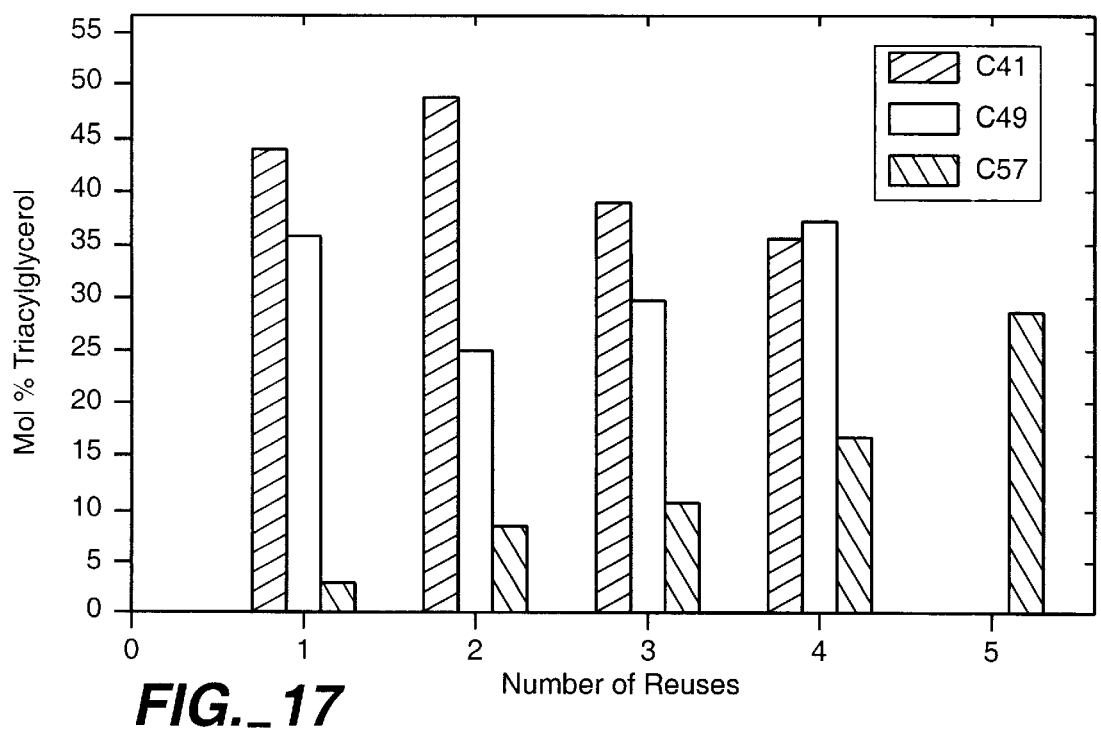
FIG._17
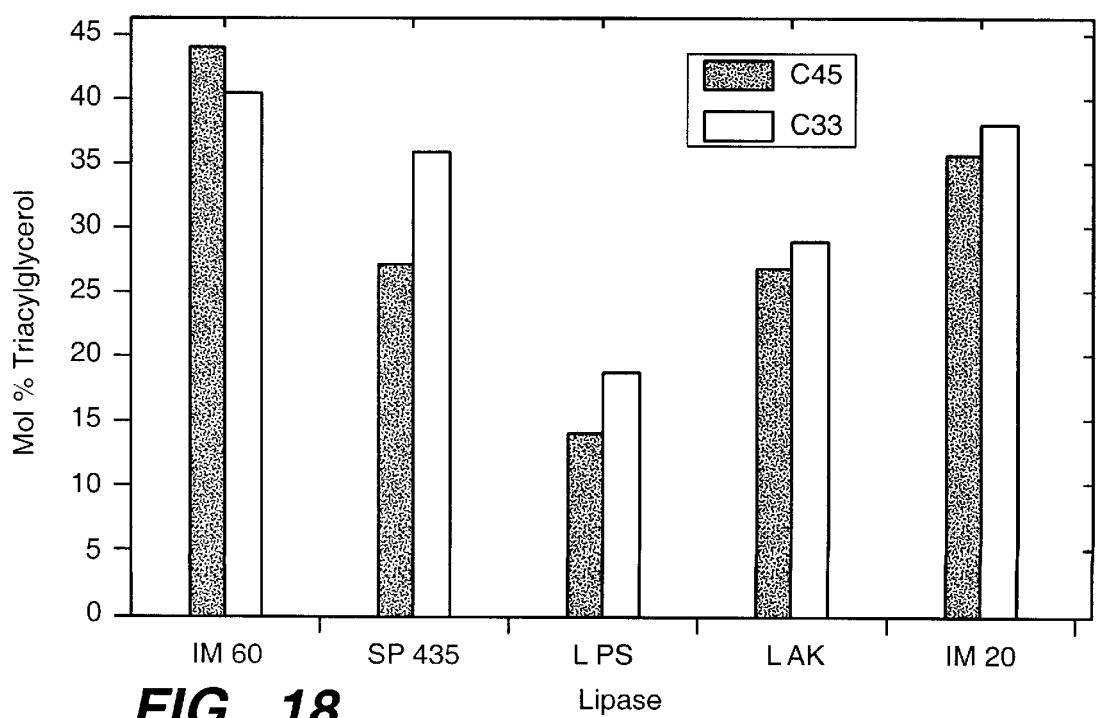
FIG._18

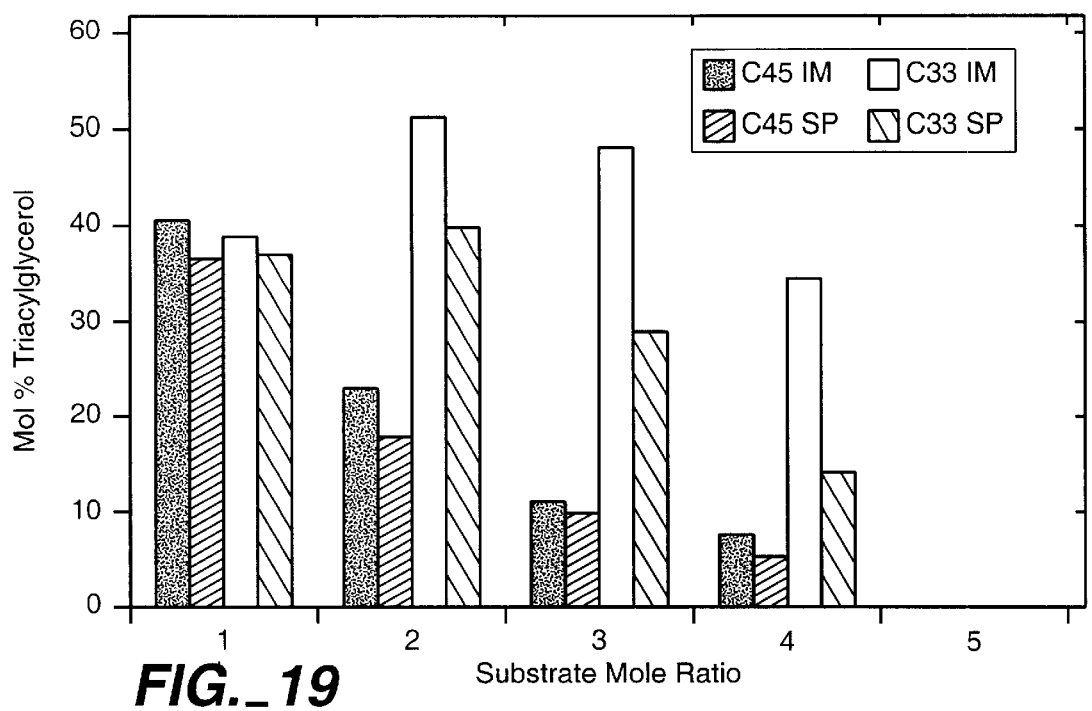
FIG._19
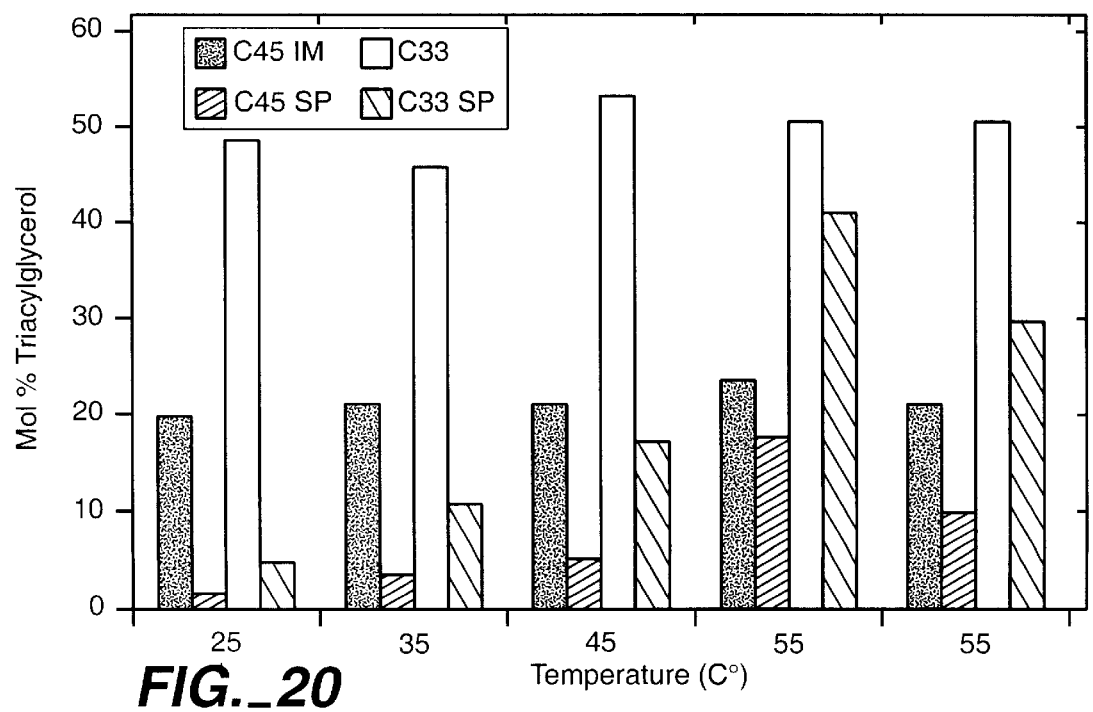
FIG._20

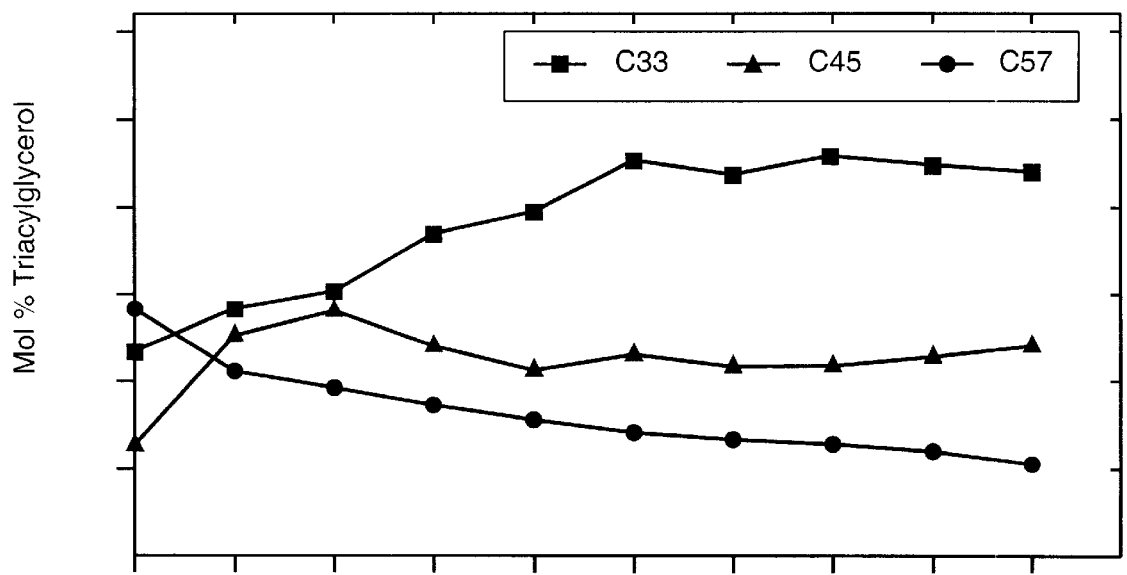
FIG._21
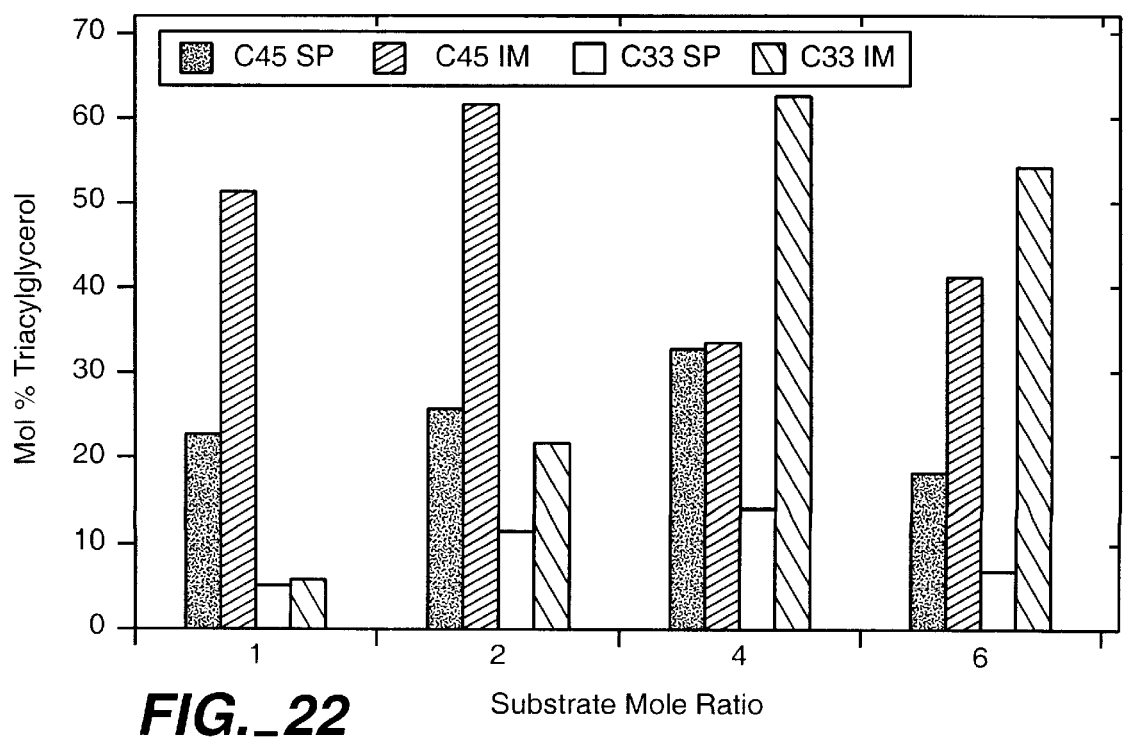
FIG._22

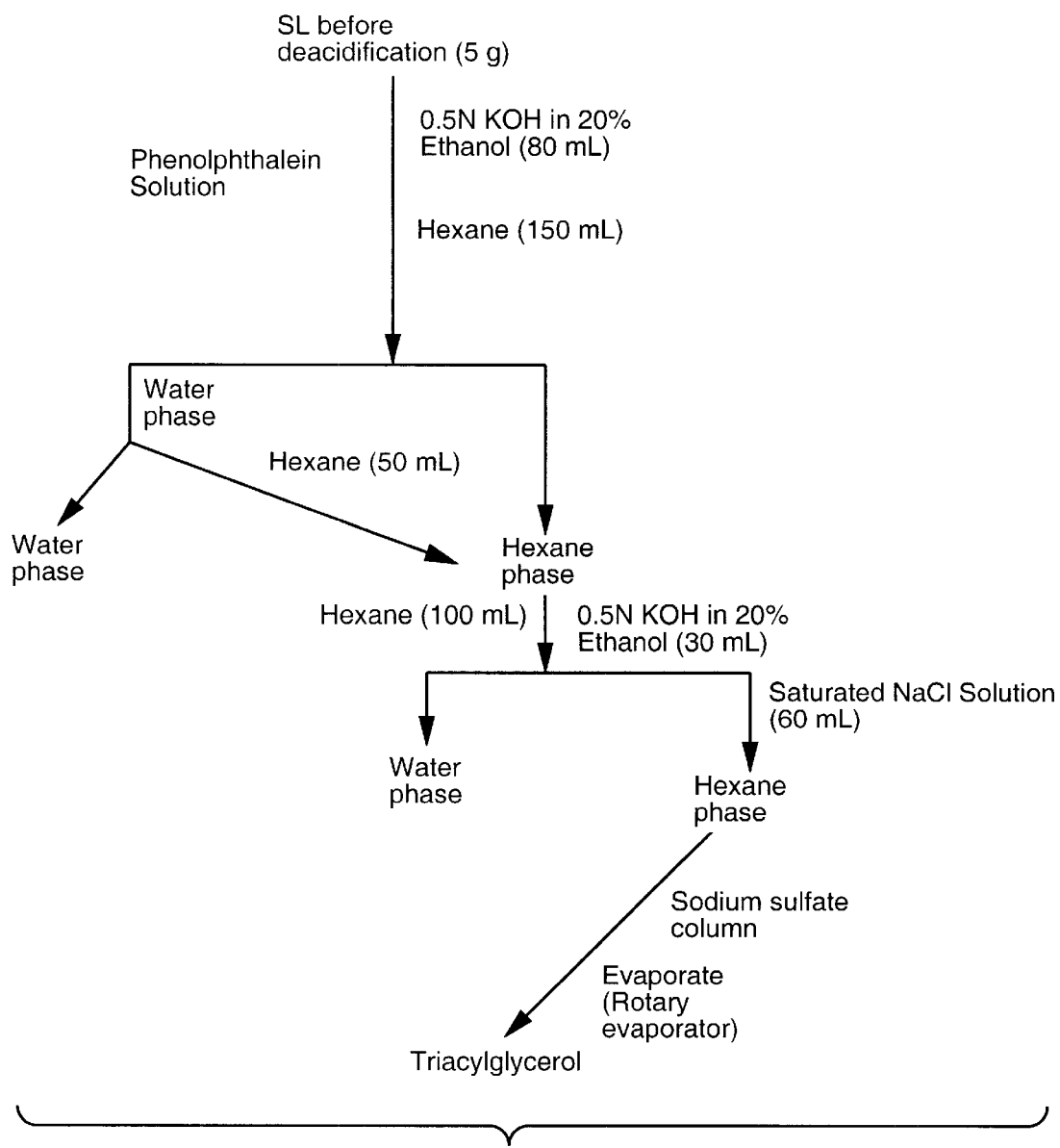
FIG._23

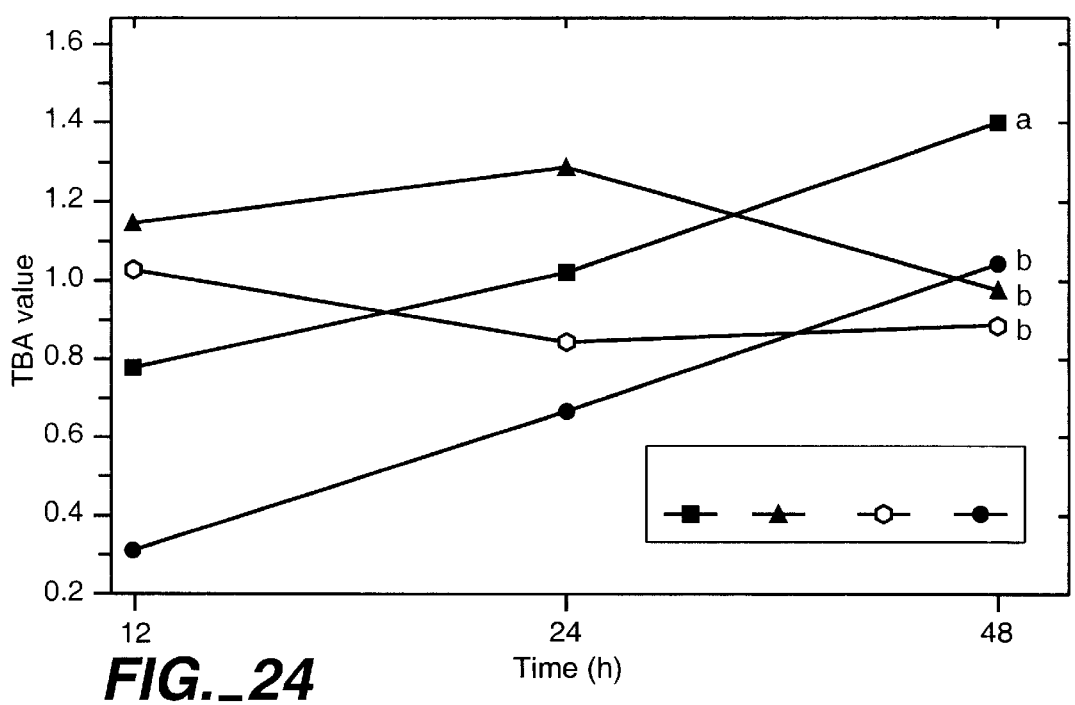
FIG._24
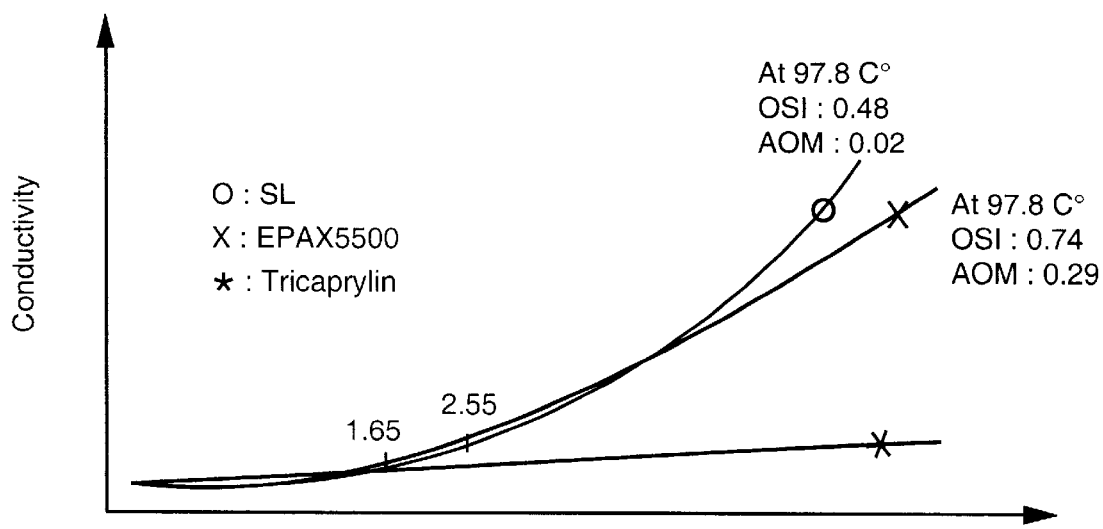
FIG._25

STRUCTURED LIPIDS

RELATED APPLICATIONS

This application claims priority to U.S. Provisional Application No. 60/076,167, filed Feb. 26, 1998, which is incorporated herein in its entirety for all purposes.

FIELD OF THE INVENTION

The present invention is directed to structured lipids comprising triacylglycerols containing at least two different fatty acids esterified to the same glycerol moiety. In particular, the invention is directed to structured lipids, methods of forming structured lipids enzymatically, and methods of use of such lipids.

BACKGROUND OF THE INVENTION

Long-chain triacylglycerols (LCTs) from soybean and safflower oils have been the standard lipids used in making fat emulsions for total parenteral nutrition and enteral administration. However, long-chain fatty acids are metabolized slowly in the body. Medium-chain triacylglycerols (MCTs) have therefore been proposed as being more desirable than LCTs because they are readily metabolized to quickly release energy. Unfortunately, pure MCT emulsions are problematic, particularly when administered intravenously.

In some cases, particular triacylglycerols have been correlated with certain physiological conditions. For example, there are indications that high levels of certain polyunsaturated fatty acids found in fish oils in Eskimo diets are responsible for their remarkably low incidence of arterial disease. Therefore, there is an interest in providing compositions which have clinical applications such as reducing the risk of arterial disease, yet which have increased absorption rates over pure LCTs.

In one approach, MCTs and LCTs are chemically interesterified, so that a single glycerol moiety contains a mixture of fatty acid chains thereon. This structure is termed a structured lipid (also called a synthetic triacyiglycerol herein).

Structured lipids are disclosed in U.S. Pat. No. 4,906,664 to Bistrian, et al., which describes a nutritional supplement for the treatment of cancer cachexia including specific structured lipids having long and medium chain fatty acids. U.S. Pat. No. 5,661,180 to DeMichele discloses a method for modulating metabolic response to trauma and disease comprising administering a structured lipid containing a gamma-linolenic or dihomogamma-linolenic fatty acid, a medium chain fatty acid, and an n-3 fatty acid. Additionally, U.S. Pat. No. 5,312,836 to Bistrian describes specific triglycerides which have at least one short chain fatty acid and at least one medium chain fatty acid, wherein at least one of the short or medium chain fatty acids is at the sn-2 position. These disclosures however provide a limited number of structured lipids for specific purposes. Moreover, they do not disclose mixtures containing a relatively high concentration or proportion of the desired structured lipid.

In efforts to provide structured lipids, a number of different approaches have been taken. In one approach, structured lipids are chemically synthesized. Chemical synthesis usually involves reaction of glycerol esters from one source with alkyl esters or glycerol esters from another to form a product with a random distribution of acyl groups. The reaction is catalyzed by alkali metals or alkali metal alkylates such as sodium methoxide. This process usually requires a temperature of 80–90° C. and anhydrous conditions. Chemical synthesis has a number of drawbacks including the high temperature conditions, randomness of the reaction, a low percentage yield of the desired structured lipid and production of undesirable by-products.

Examples of chemically synthesized structured lipids include caprenin which is a common name for caprocaprylobehenin, a structured lipid containing 8:0, 10:0, and 22:0 fatty acids esterified to glycerol. See, e.g., Akoh, *Lipid Technology*, 61–66 (May 1997). Another product is salatrim which contains 2:0, 3:0, 4:0, and 18:0 fatty acids esterified to glycerol. See, e.g., Akoh, *Lipid Technology*, 61–66 (May 1997). The fatty acids of these structured lipids are each saturated.

An alternative to the chemical synthesis of structured lipids is the use of lipases. Lipases can catalyze the transesterification of triacylglycerols with fatty acids (acidolysis), the transesterification of glycerol esters (ester-ester transfer) or direct esterification of free fatty acids with glycerol. Enzymatic approaches to forming structured lipids have been previously described, e.g., Akoh, INFORM, 6(9):1056–1061 (September 1995) and Akoh and Sista, *J. Food Lipids*, 2:231–238 (1995). However, despite these disclosures, there remains a need for a greater variety of structured lipids and mixtures comprising structured lipids.

It is therefore an object of the invention to provide novel structured lipids. It is also an object to provide novel mixtures comprising structured lipids in relatively high yields. It is further an object to provide enzymatic methods of forming these structured lipids and mixtures comprising structured lipids.

It is additionally an object of the invention to provide methods of modulating total cholesterol levels, low-density lipoprotein cholesterol levels, triacylglycerol levels, and/or the ratio of T-helper cells to T-cytotoxic cells in an individual comprising administrating a structured lipid mixture. It is further an object to provide a method of modulating weight in an individual comprising administrating a structured lipid mixture.

SUMMARY OF THE INVENTION

In accordance with the foregoing objectives, structured lipids and mixtures comprising structured lipids are disclosed as well as enzymatic methods of forming them.

The invention includes a synthetic triacylglycerol having fat acids $R_1$, $R_2$ and $R_3$ esterified to the glycerol moiety. In one embodiment, at least one of $R_1$, $R_2$ and $R_3$ is a short chain fatty acid and $R_2$, in the sn-2 position, is an unsaturated fatty acid. In another embodiment, at least one of $R_1$, $R_2$ and $R_3$ is a short chain fatty acid and at least one of $R_1$, $R_2$ and $R_3$ is an n-9 fatty acid. In an alternative embodiment, two of $R_1$, $R_2$ and $R_3$ is a short chain fatty acid and one of $R_1$, $R_2$ and $R_3$ is an unsaturated fatty acid. In yet another embodiment, one of $R_1$, $R_2$ and $R_3$ is a short chain fatty acid and each of the remaining $R_1$, $R_2$ and $R_3$ is a long chain fatty acid. Additional synthetic triacylglycerols provided by the methods described herein are also provided.

The enzymatic methods of the invention generally include combining acylglycerols, preferably triacylglycerols, or glycerophospholipids with one or more lipases under conditions which allow formation of mixtures comprising structured lipids by transesterification. In some cases, fatty acids and/or esters are combined with one or more acylglycerols or glycerophospholipids in the presence of an appropriate lipase(s).

In a specific embodiment, triolein, caproic acid, butyric acid and a lipase are combined. In another specific embodiment, a gamma-linolenic rich oil, a short or medium chain fatty acid, an unsaturated fatty acid other than the gamma-linolenic fatty acid and a lipase are combined. In an alternative specific embodiment, an n-3 fatty acid rich oil, tricaprylin and a lipase are combined. In yet another specific embodiment, tricaprin or trilinolein, capric acid ethyl ester and a lipase are combined. In yet a further specific embodiment, tristearin, a medium chain fatty acid and a lipase are combined. In an additional specific embodiment, trilinolein, tricaprin or caproic acid and a lipase are combined. In another specific embodiment, tricaprylin, an n-3 unsaturated fatty acid and a lipase are combined.

The lipase(s) used in the specific embodiments can be specific, non-specific, or a combination thereof. In a preferred embodiment, the lipase is specific for the sn-1 and sn-3 positions of the triacylglycerol.

All of the mixtures and structured lipids formed from the methods herein are within the scope of this invention. Generally, the mixtures resulting from the enzymatic reactions have higher percentages of the desired structured lipid than when using chemical synthesis. Moreover, the enzymatic reactions result in less side products than chemical synthesis using the same starting materials.

Also provided herein are methods of modulating total cholesterol levels, low-density lipoprotein cholesterol levels, triacylglycerol levels, and/or the ratio of T-helper cells to T-cytotoxic cells in an individual comprising administrating a structured lipid mixture in accordance with this invention. It is further an object to provide a method of modulating weight in an individual comprising administrating a structured lipid mixture in accordance with this invention.

BRIEF DESCRIPTION OF THE DRAWINGS

FIG. 1 is a graph showing the effect of mole ratio of substrates on structured lipids synthesis with IM 60 as a biocatalyst. The letter S designates short-chain fatty acids ($C_{6:0}$, $C_{4:0}$) and L designates long-chain fatty acid (18:1n-9). LLL=triolein (unreacted), LLS=monosubstituted structured lipid, and SLS=disubstituted structured lipid.

FIG. 2 is a graph showing the effect of temperature on incorporation of caproic and butyric acids into triolein. The letter S designates short-chain fatty acids ($C_{6:0}$, $C_{4:0}$) and L designates long-chain fatty acid (18:1n-9). LLL=triolein (unreacted), LLS=monosubstituted structured lipid, and SLS=disubstituted structured lipid.

FIG. 3 is a graph showing the time course of caproic and butyric acids incorporation into triolein catalyzed by IM 60 lipase. Samples were analyzed at 2, 4, 6, 12, 24, 48 and at 72 hours in duplicate. The letter S designates short-chain fatty acids ($C_{6:0}$, $C_{4:0}$) and L designates long-chain fatty acid (18:1n-9). LLL=triolein (unreacted), LLS=monosubstituted structured lipid, and SLS=disubstituted structured lipid.

FIG. 4 is a graph showing the effect of enzyme load on incorporation of butyric and caproic acids into triolein. Amount of enzyme varied from 0 to 30%, total weight of substrates. The letter S designates short-chain fatty acids ($C_{6:0}$, $C_{4:0}$) and L designates long-chain fatty acid (18:1n-9). LLL=triolein (unreacted), LLS=monosubstituted structured lipid, and SLS=disubstituted structured lipid.

FIG. 5 is a graph depicting the time course of incorporation of eicosapentaenoic acid (EPA) (20:5n-3) and capric acid (10:0) into borage oil triacylglycerols (TAG) by IM 60 and SP 435 lipase catalyzed transesterification. Mole ratio of borage oil, 20:5n-3 and 10:0 is 1:2:2.

FIG. 6 is a graph depicting the effect of IM 60 and SP 435 lipase load on incorporation of 20:5n-3 and 10:0 into borage oil TAG.

FIG. 7 is a graph depicting the effect of added water on incorporation of 20:5n-3 and 10:0 into borage oil TAG using IM 60 and SP 435 lipases.

FIG. 8 depicts a high-performance liquid chromatography chromatogram showing the molecular species of reactants and structured lipid (SL) products. The reaction is with tricaprin and trilinolein as substrates and SP 435 as biocatalyst, where (from left) peak #1=unreacted tricaprin; #2=SL1; #3=SL2; #4=unreacted trilinolein; and #5=internal standard.

FIGS. 9A and 9B are schematics showing interesterification between trilinolein and tricaprin with either IM 60 lipase, (FIG. 9A), or SP 435 lipase (FIG. 9B).

FIGS. 10A and 10B are schematics showing the possible products from a reaction between capric acid ethyl ester and trilinolein with either IM 60 lipase, (FIG. 10A), or SP 435 lipase (FIG. 10B).

FIGS. 11A and 11B are graphs depicting mol % of synthesized SL1 and SL2 after the interesterification of tricaprin or capric acid ethyl ester with trilinolein and IM 60 (FIG. 11A) or SP 435 (FIG. 11B). SL1 with capric acid ethyl ester (-♦-); SL: with one linoleic acid in the reaction between trilinolein and capric acid ethyl ester; SL2 with capric acid ethyl ester (-◊-); SL: with two linoleic acids in the reaction between trilinolein and capric acid ethyl ester; SL1 with tricaprin (-■-); SL: with one linoleic acid in the reaction between tricaprin and trilinolein; SL2 with tricaprin (-□-); SL: with two linoleic acids in the reaction between tricaprin and trilinolein.

FIGS. 12A and 12B are graphs depicting mol % of synthesized SL1 and SL2 after the interesterification of tricaprin or tristearin with trilinolein. FIG. 12A shows IM 60 and FIG. 12B shows SP 435. SL1 with tricaprin (-♦-); SL with one linoleic acid in the reaction between trilinolein and tricaprin; SL2 with tricaprin (-◊-); with two linoleic acids in the reaction between trilino lein and tricaprin; SL1 with tristearin (-■-); SL one linoleic acid in the reaction between tristearin and trilinolein; SL2 with tristearin (-□-); SL: with two linoleic acids in the reaction between tristearin and trilinolein.

FIG. 13 is a graph depicting the effect of substrate mole ratio on the interesterification of tristearin and tricaprin with IM 60 lipase. Mole ratios were varied from 1:1 to 1:5 (tristearin:tricaprin).

FIG. 14 is a graph depicting the effect of enzyme load on structured lipid production from tricaprin and tristearin. The amount of enzyme ranged from 0 to 30% (w/w of reactants).

FIG. 15 is a graph depicting the time course of IM 60 lipase-catalyzed interesterification of tristearin and tricaprin.

FIG. 16 is a graph depicting the effect of added water on lipase-catalyzed interesterification of tristearin and tricaprin with IM 60 as biocatalyst. Amount of water added varied from 0 to 30% (w/w of reactants).

FIG. 17 is a bar graph depicting the effect of enzyme reuse on lipase-catalyzed interesterification of tristearin and tricaprin with IM 60 as the biocatalyst.

FIG. 18 is a bar graph depicting lipase screening for the interesterification reaction between trilinolein and tricaprin. C33=dicaproyllinolein, C45=monocaproyldilinolein. The number after C indicates total carbon number of the triacylglycerols.

FIG. 19 is a bar graph depicting the effect of mole ratio of substrates on interesterification of trilinolein and tricaprin with IM 60 or SP 435 lipase as biocatalysts. The mole ratio of trilinolein and tricaprin was varied from 1:1 to 1:4 IM=IM 60, SP=SP 435, C33=dicaproyllinolein, C45=monocaproyldilinolein. The number after C indicates total carbon number of the triacylglycerols.

FIG. 20 is a bar graph depicting the effect of temperature on the lipase-catalyzed interesterification of trilinolein and tricaprin (1:2 mole ratio) with IM 60 or SP 435 lipase.

FIG. 21 is a graph depicting the time course of IM 60 lipase-catalyzed interesterification of trilinolein and tricaprin. The mole ratio of trilinolein to tricaprin was 1:2.

FIG. 22 is a bar graph depicting the effect of free fatty acid as acyl donor. The mole ratio of trilinolein to caproic acid was varied from 1:1 to 1:6.

FIG. 23 is a schematic for deacidification by alkaline extraction.

FIG. 24 is a bar graph depicting thiobarbituric acid (TBA) number of SL without or with α-tocopherol (1, 2, 4%).

FIG. 25 is a bar graph depicting the graphical determination of the induction period of SL, EPAX 5500 (fish oil TAG) and tricaprylin by a slope/change algorithm method. OSI values were converted to AOM values by the automated Omnion Instrument. SL=structured lipids, OSI=oxidative stability index, AOM=active oxygen method (o:SL, x:EPAX 5500, *:Tricaprylin).

DETAILED DESCRIPTION OF THE INVENTION

The types of fatty acids bound to a single triacylglycerol molecule which are generally thought to be the most beneficial to an individual, are either not naturally present in available fats and oils or are not arranged in the desired stereochemical order. The present invention provides methods for modifying existing fats and oils or, alternatively, to synthesize new ones which have desirable properties. This process is sometimes referred to as structuring lipids and the products are referred to as structured lipids. Structured lipids are synthetic acylglycerols, preferably triacylglycerols, containing at least two different fatty acids esterified to the same glycerol moiety. Alternatively, the structured lipid is a phosphoglyceride having one or more fatty acids esterified to a hydroxyl group of the phosphoglyceride. Both chemical and enzymatic processes, namely direct esterification, acidolysis and ester-ester interchange reactions can be used to synthesize or re-structure lipids as provided herein.

The present invention also provides a novel set of structured lipids defined in part by the starting materials and processes used to make them. Generally, the processes provided herein provide novel structured lipids and/or novel mixtures which comprise structured lipids.

The synthetic triacylglycerols provided herein contain specific mixtures of short-chain ($C_2$–$C_6$), medium-chain ($C_7$–$C_{12}$), and/or long chain ($C_{13}$–$C_{24}$) fatty acids esterified to a glycerol moiety. In some cases the fatty acids are saturated, in that they have only single carbon bonds in the fatty acid backbone. Saturated fatty acids herein include those of the formula:

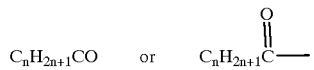

when used as an R group covalently linked to an oxygen of glycerol. In other cases, the fatty acids are unsaturated, e.g., have at least one double carbon bond in the fatty acid backbone. Unsaturated fatty acids herein include those of the formula: $C_nH_{2n-1}CO$; $C_nH_{2n-3}CO$; $C_nH_{2n-5}CO$ and so on, where the CO is C=O as shown above when used as an R covalently linked to an oxygen of glycerol. These fatty acids can be summarized as

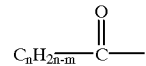

where m is the number of double bonds and is an odd integer from 1 to (n-1)/2 when n is odd and n/2 when n is even. Unsaturated fatty acids are sometimes also identified by the position of the unsaturated bond. For example, if there is, i.e., a double bond, between the third and fourth carbon atoms from the methyl ($CH_3$) group, the molecules are referred to as n-3; n-6 refers to a non-single bond between the sixth and seventh carbon atoms, n-9 refers to a non-single bond between the ninth and tenth carbon atoms and so on.

Examples of short chain fatty acids that can be used herein are: acetic ($C_{2:0}$); propionic ($C_{3:0}$); butyne ($C_{4:0}$); valeric ($C_{5:0}$); and caproic ($C_{6:0}$) acid.

Examples of medium chain fatty acids that can be used herein are: enanthic ($C_{7:0}$); caprylic ($C_{8:0}$); pelargonic ($C_{9:0}$); capric ($C_{10:0}$); and lauric ($C_{12:0}$).

Examples of saturated and unsaturated long chain fatty acids that can be used herein are systematically named: tridecanoic ($C_{13:0}$); tetradecanoic ($C_{14:0}$); pentadecanoic ($C_{15:0}$); hexadecanoic ($C_{16:0}$); 9-hexadecenoic ($C_{16:in-7}$); octadecanoic ($C_{18:0}$), 9-octadecenoic ($C_{18:in-9}$); 9,12-octadecadienoic ($C_{18:2n-6}$); 9,12,15-octadecatrienoic ($C_{18:3n-3}$), 6,9,12-octadecatrienoic ($C_{18:3n-6}$); eicosanoic ($C_{20:0}$); 11-eicosenoic ($C_{20:1n-9}$); 8,11,14-eicosatrienoic ($C_{20:3n-6}$); 5,8,11,14-eicosatetraenoic ($C_{20:4n-6}$); 5,8,11,14,17-eicosapentaenoic (EPA, $C_{20:5n-3}$); docosanoic ($C_{22:0}$); 13-docosenoic ($C_{22:1n-9}$); 7,10,13,16,19-docosapentaenoic (DPA, $C_{22:5n-3}$); 4,7,10,13,16,19-docosahexaenoic (DHA, $C_{2:6n-3}$); tetracosanoic ($C_{24:0}$); and 15-tetracosenoic ($C_{24:in-9}$) acid. Numbers before the name indicate the positions of the double bonds while the number after the colon denotes the number of double bonds from the methyl end of the acid.

The structured lipids can also be formed by incorporating short and/or medium chain fatty acids onto various lipids such as glycerophospholipids. Glycerophospholipids such as phosphatidylcholine (PC), phosphatidylethanolamine (PE), phosphatidylinositol (PI), and phosphatidylglycerol (PCG) can be used with the addition of lipases or phospholipases $A_1$ and $A_2$.

The component fatty acids and their position in the triacylglycerol or glycerophospholipid molecule contribute to the function and physical properties, metabolic fate, and putative health benefits of the structured lipid. For example, structured lipids may be preferably targeted for either portal or lymphatic transport. Generally, fatty acids of chain length 2:0 to 12:0 (e.g., short and medium chain fatty acids) are transported through the portal system, while those of 13:0 to 24:0 (predominately long chain fatty acids) pass through the lymphatic system.

The absorption and transport of structured lipids is also influenced by the position of the constituent fatty acids esterified to the glycerol moiety. To improve absorption, it is preferable that the fatty acid be esterified to the oxygen at the sn-2 position of the glycerol moiety. All of these factors can be taken into account when forming the structured lipids provided herein.

The triacylglycerols can also be made to contain one or more fatty acids to provide a structured lipid with desirable properties, (see generally, Akoh, *Lipid Technology*, 61–66 (May 1997) and particularly the specific examples herein). For example, n-3 fatty acids (long unsaturated fatty acids) generally enhance immune function, reduce blood clotting, lower serum triacylglycerols, and reduce risk of coronary heart disease. Generally, n-6 fatty acids (long unsaturated fatty acids) satisfy essential fatty acid requirement in the diet. Also, n-9 fatty acids, i.e., mono-unsaturated long chain fatty acid 18:1n-9, are useful for the balance of long-chain fatty acids. Structured lipids containing at least one short-chain (SCFA) and/or medium chain fatty acid (MCFA) are useful for rapid absorption and energy release, especially for immature neonates, hospitalized patients and individuals with lipid malabsorption disorders. These factors are also considered when forming the structured lipids herein.

The structured lipids and mixtures can be formed chemically or enzymatically. Preferably, the structured lipids are formed enzymatically. The enzymatic reactions are catalyzed by lipases. Preferably, the lipase enzyme is immobilized to enable enzyme re-use and to facilitate continuous processes. Suitable support materials for lipase immobilization are widely available. Immobilized lipases can be commercially obtained from Novo Nordisk Biochem North America, Inc. (Franklinton, N.C.). The lipases are immobilized in ion exchange resins by adsorption. Moreover, lipases can be immobilized by adsorption, covalent attachment, or by crosslinking with suitable crosslinking agents as described in Akoh, *Food Lipids and Health*. Marcel Dekker, New York pp. 117–138 (1996); Malcata, et al., *Enzyme Microb. Technol.*, 14:426–446 (1992). In addition, the lipases are preferably thermostable.

The specificity of lipases has been divided classically into five major types: lipid class (e.g., simple, compound and derived lipids); positional, e.g., sn-1, –2 or 3; fatty acid, e.g., substrate specific; stereochemical; and combinations of these as described in Malcata, et al., *Enzyme Microb.Technol.*, 14:426–446 (1992). Lipases from each of these categories may be used herein, including combinations derived from the same or different class.

Examples of suitable lipases include: nonspecific lipases from *Pseudomonas cepacia, Candida antarctica*, Aspergillus sp., *Penicillium expansum*; sn-1,3 regiospecific lipases from *Rhizomucor miehei, Aspergillus arrhizus*; sn-2 regiospecific lipase from Candida antarctica A. Others include cis-9 unsaturated fatty acid specific lipase from *Geotrichum candidum* and short chain fatty acid specific lipase from *Penicillium roqueforti*.

Examples of suitable phospholipases include phospholipase $A_1$ and $A_2$ from snake venom which are specific for the sn-1 and sn-2 positions of the glycerophospholipids, respectively.

Lipases can be used in several ways in the modification of triacylglycerols (Akoh, *Food Lipids and Health*, Marcel Dekker, New York pp. 117–138 [1996]). In an aqueous medium, hydrolysis is the dominant reaction when a lipase is combined with an appropriate ester substrate. In organic media, esterification and interesterification reactions are predominant. Moreover, when these enzymes are placed in an organic or mixed organic-aqueous environment, they exhibit novel characteristics such as altered chemoselectivity, altered stereoselectivity, enhanced stability and increased rigidity. In the preferred embodiments, both water and organic solvents are used.

Various methods can be used for the lipase-catalyzed production of the structured lipids provided herein. The method of choice depends to a large extent on the products desired. Generally, direct esterification or transesterification is used.

In more detail, direct esterification can be used for the preparation of the structured llipids of this invention by reacting free fatty acids with glycerol. A representative reaction is: Glycerol+a medium chain fatty acid (MCFA)+a long chain fatty acid (LCFA)+Lipase→SL+Water. Preferably the water is removed as it is formed to minimize hydrolysis of the product.

Transesterification by acidolysis can also be utilized to form the structured lipids of the present invention. Acidolysis is a type of transesterification reaction involving the exchange of acyl groups between an ester and a free acid. Representative reactions are: MCT+LCFA+Lipase→SL+MCFA; and, LCT+MCFA+Lipase→SL+LCFA.

In another embodiment, the structured lipids of the present invention are formed by transesterification by ester-ster interchange. This reaction involves the exchange of acyl groups between one ester and another ester. Representative reactions are: MCT +LCT+Lipase→SL; LCT+a medium-chain fatty acid aklyl ester (i.e., ethyl ester) (MCFAAE)+Lipase→SL+a long-chain fatty acid aklyl ester (i.e., ethyl ester) (LCFAAE); and MCT+LCFAAE+Lipase→SL+MCFAAE.

Purification, if desired, can be by standard techniques after the enzymatic reaction. For example, thin layer chromatography (TLC), solvent evaporation, column or flash chromatography, preparative high-performance liquid chromatography (prep-HPLC), supercritical fluid chromatography (SFC) and short-path distillation techniques can be used. Free fatty acids are removed by distillation or by other appropriate techniques. In general, enzymatic reactions produce less side or by-products than chemical synthesis of structured lipids.

In the above examples, short-chain triacylglycerol or short chain fatty acids can replace MCAE and medium-chain fatty acids, respectively, or can be used in combination. Enzymes can thus be used to synthesize position-specific structured lipids, such as, e.g., structured lipids containing n-3 polyunsaturated fatty acids. Such structured lipids can be used to improve immune function and reduce serum cholesterol.

The most useful properties of lipases are their regiospecificity and stereospecificity. These properties result in structured lipids with a more predictable chemical composition and structure than those obtained by chemical catalysis. Advantages of using lipase enzymes instead of chemical procedures include the specificity of enzymes and the relatively mild reaction conditions under which enzymes operate. Chemical catalysts randomize fatty acids in triacylglycerol mixtures and often fail to yield speciality products with desired physicochemical characteristics.

In one embodiment, sn-1,3 specific lipases are used to provide structured lipid products which retain the starting fatty acid at the sn-2 position. This is important when providing nutritional supplements. For example, the 2-mono-acylglycerols produced by pancreatic lipase during digestion are the primary carriers of fatty acids through the intestinal wall. Structured lipids containing fatty acids esterified at the sn-2 position are therefore generally more efficiently absorbed than those esterified at the sn-1 and sn-3 positions. Triacylglycerols containing an essential fatty acid (EFA) at the sn-2 position and short-chain or medium-chain fatty acids at the sn-1 or sn-3 positions therefore have the advantage of efficiently providing an EFA and a quick energy source.

In addition, the rate of autoxidation and melting properties of triacylglycerols can be affected by the position of unsaturated fatty acids in the triacylglycerol molecule. Triacylglycerols having unsaturated fatty acids at the sn-2 position of glycerol are more stable toward oxidation than those linked at the sn-1 and sn-3 positions.

In other embodiments, non-specific lipases are preferred so as to incorporate the desired fatty acid chain at the sn-2 position. This is desirable so as to provide a wide variety of structured lipids which are not otherwise found in nature.

Uses of the structured lipids and mixtures comprising structured lipids provided herein include their use as ingredients in margarine, butter, spreads, shortening, dressings, dips, and sauces, confectioneries, sport and beverage drinks, soft candies, baking chips and baked goods, and snack foods and dairy products. They also can be used as reduced calorie or low calorie fats, for improving the melting properties of fats and as a cocoa butter substitute.

The structured lipids and mixtures comprising structured lipids can also be used for a variety of physiological applications. For example, they can be used to provide superior nitrogen retention, preservation of reticuloendothelial system function and attenuation of protein catabolism and the hypermetabolic stress response to thermal injury. The structured lipids and mixtures provided herein can also be used to enhance absorption of the fatty acid at the sn-2 position, e.g., 18:2n-6 in cystic fibrosis patients; reduce serum triacylglycerol, LDL-cholesterol and cholesterol, improve immune function and prevent thrombosis. Furthermore, this invention provides lipid emulsions and structured lipids for enteral and parenteral feeding, calorie reduction, and improved absorption of other fats.

In one embodiment, a synthetic triacylglycerol having fatty acids $R_1$, $R_2$ and $R_3$ esterified to the glycerol moiety is provided. At least one of $R_1$, $R_2$ and $R_3$ is a short chain fatty acid and $R_2$, in the sn-2 position, is an unsaturated fatty acid. In another embodiment, at least one of $R_1$, $R_2$ and $R_3$ is a short chain fatty acid and at least one of $R_1$, $R_2$ and $R_3$ is an n-9 fatty acid. In an alternative embodiment, two of $R_1$, $R_2$ and $R_3$ is a short chain fatty acid and one of $R_1$, $R_2$ and $R_3$ is an unsaturated fatty acid. In yet another embodiment, one of $R_1$, $R_2$ and $R_3$ is a short chain fatty acid and each of the remaining $R_1$, $R_2$ and $R_3$ is a long chain fatty acid. Additional synthetic triacylglycerols yielded from the methods described herein are also provided.

In another embodiment, lipase-catalyzed acidolysis of triolein with caproic and butyric acids is used to produce reduced-calorie structured lipids. Preferably, a 1:4:4 mole ratio of triolein, caproic acid, and butyric acid, respectively, is incubated with lipase. From this method, one can produce about 13 mol % unreacted triolein, about 49% disubstituted, and about 38% monosubstituted triacylglycerols that contain short-chain fatty acids ($C_4$ to $C_6$). The yields obtained demonstrate that a structured lipid with long-chain and short-chain fatty acids can be synthesized by using IM 60 lipase in organic medium.

In yet another embodiment, two immobilized lipases, a non-specific SP 435 from *Candida antarctica* and an sn-1,3 specific IM 60 from *Rhizomucor miehei*, are used as biocatalysts for the restructuring of a gamma-linolenic rich oil to incorporate a second polyunsaturated fatty acid and a short or medium-chain fatty acid with the free fatty acids as acyl donors. Preferably, medium chain fatty acids and n-3 fatty acids are used. The oil can be selected from borage oil, primrose oil, black currant seed oil, algae oil and fungal oil. hn a preferred embodiment, the modified oil comprises at least 20 mol % saturated fatty acids and at least 3 mol % n-3 unsaturated fatty acids.

In a further embodiment provided herein, IM 60 or SP 435 was combined with tricaprin and trilinolein. Interesterification produced SL that contained one linoleic acid per triacylglycerol molecule (SL1) and SL with two linoleic acids (SL2). With IM 60, 57.7 mol % capric acid and 42.3 mol % linoleic acid were found at the sn-2 position of SL1, while 43.3 mol % capric acid and 56.7 mol % linoleic acid were at the sn-2 position of SL2. The fatty acid at the sn-2 position of SL1 with SP 435 as biocatalyst was 43.6 mol % capric acid and 56.4 mol % linoleic acid, while SL2 contained 56.6 mol % capric acid and 43.4 mol % linoleic acid.

In yet another embodiment, IM 60 was used to catalyze the interesterification of tristearin (C18:0) and tricaprin (C10:0) to produce reduced-calorie structured lipids. A 1:1 mole ratio of both triacylglycerols with 10% (w/w of reactants) of IM 60 was utilized. The SL molecular species based on total carbon number were 44.2% C41 and 40.5% C49 with 3.8 and 11.5% unreacted tristearin C57 and tricaprin C27, respectively, remaining in the product mixture. Tricaprylin (C8:0) was also successfully interesterified with tristearin in good yields at 1:1 mole ratio. Hydrolysis by pancreatic lipase revealed the specific fatty acids present at the sn-1,3 positions of SL.

In an alternative embodiment provided herein, structured lipids were synthesized by interesterification of trilinolein and tricaprin using IM 60 and SP 435. The interesterification reaction was performed by incubating a 1:2 mole ratio of trilinolein and tricaprin. The fatty acids at the sn-2 position were identified after pancreatic lipase hydrolysis. IM 60 lipase produced 53.5 mol % dicaproyllinolein (total carbon number, TCN=C33), and 22.2% monocaproyldilinolein (C45). SP 435 lipase produced 41% C33 and 18% C45. When caproic acid was used in place of tricaprin as the acyl donor, the IM 60 lipase produced 62.9% C33.

In another embodiment, structured lipids containing polyunsaturated n-3, preferably, eicosapentaenoic or docosahexaenoic fatty acids, and medium-chain fatty acids, preferably caprylic, were synthesized in gram quantities. Tricaprylin was mixed with n-3-rich polyunsaturated fatty acids in a 1:2 molar ratio and transesterified with SP 435 lipase (10% by weight of total substrates). Up to 240 grams of SL was isolated and deacidified by alkaline extraction or ethanol-water solvents.

In yet a further embodiment, an unsaturated fatty acid rich oil and a short or medium chain fatty acid are combined with a lipase. Preferably, an n-3 fatty acid rich oil and tricaprylin are utilized. The mixture formed from this reaction is also provided. This mixture is used herein to modulate total cholesterol levels, low-density lipoprotein cholesterol levels, triacylglycerol levels, and/or the ratio of T-helper cells to T-cytotoxic cells in an individual upon administration. This mixture can also be used as a substitute in diets which contain fat. The fats or oils are substituted with the structured lipids or mixtures comprising structured lipids provided herein.

Also provided herein is a structured lipid mixture comprising from 40 mol % to 70 mol % medium chain fatty acids, 0 mol % to 3 mol % saturated long chain fatty acids, and 30 mol % to 50 mol % unsaturated long chain fatty acids. This mixture is also used herein to modulate total cholesterol levels, low-density lipoprotein cholesterol levels, triacylglycerol levels, calorie intake, and/or the ratio of T-helper cells to T-cytotoxic cells in an individual upon administration.

In yet a further embodiment, diets are supplemented with structural lipids containing n-3 polyunsaturated fatty acids, preferably, eicosapentaenoic and decosahexaenoic, and short or medium chain fatty acids, preferably, caprylic acid, or soybean oil (16.7 g/100 g). The concentration of total cholesterol (−49%), LDL-cholesterol (−35.4%) and triacylglycerol (−53.2%) were significantly lower in SL-fed group. The body weight gain in mice fed the soybean oil diet was significantly (p<0.05) greater than that in mice fed the SL diet after 21 days. A 16% higher CD4+/CD8+ratio was observed in the SL-fed group compared to the soybean oil-fed group.

All of the mixtures formed from the methods herein are within the scope of this invention. Generally, the mixtures resulting from the enzymatic reactions have higher percentages of the desired structured lipid than when using chemical synthesis. Moreover, the enzymatic reactions result in less side products than chemical synthesis of structured lipids.

The following examples are intended merely to illustrate embodiments of the invention and are not to be considered as limited to the details of each example.

SPECIFIC EXAMPLE 1

ENZYTIC MODIFICATION OF TRIOLEIN: INCORPORATION OF CAPROIC AND BUTYRIC ACIDS TO PRODUCE REDUCED-CALORIE STRUCTURED LIPIDS

In this example, reduced-calorie structured lipids are formed to have short chain and unsaturated long chain fatty acids.

MATERIALS AND METHODS

Materials. Butyric acid, caproic acid, and triolein were obtained from Sigma Chemical Company (St. Louis, Mo.). Lipase G from *Penicillium cyclopium*, PS from Pseudomonas sp., L from *Candida lipolytica*, N from *Rhizopus niveus*, AK from Pseudomonas sp., and AY-30 from *C. ragosa* were kindly provided by Amano Enzyme Co. (Troy, Va.). IM 60 and IM 20 with immobilized lipase from *Rhizomucor miehei*, and SP 435 immobilized lipase from *C. antarctica* were obtained from Novo Nordisk Biochem North America Inc. (Franklinton, N.C.). Porcine pancreatic lipase and 1,3 distearoyl-2-oleoyl-glycerol were purchased from Sigma. All solvents used were of high-performance liquid chromatograph (HPLC) grade and were obtained from Fisher Scientific (Norcross, Ga.).

Transesterification reaction. SL synthesis was performed in screw-capped test tubes in an orbital shaking waterbath at 200 rpm and 55° for 24 hours. The reaction mixture contained typically 50 mg triolein, 26 mg caproic acid, 20 mg butyric acid, and 9.6 mg lipase (i.e., 10% w/w of total substrates) in 1.5 mL of hexane that was previously dried over molecular sieve 4 Å. All reactions were performed in duplicate.

Extraction and analytical methods. The reaction products were cooled and filtered through a sodium sulfate column to remove any moisture and enzyme particles. Products were analyzed in a Hewlett-Packard 1090 HPLC (Avondale, Pa.), equipped with a Sedex 45 evaporative light-scattering detector (ELSD) (Richard Scientific, Novato, Calif.). The ELSD was set at 40° C., a nitrogen nebulizer gas pressure of 2.1 atmospheres, and a gain of 5 for the nonaqueous reverse-phase system. A Hewlett-Packard 35900 digital A/D analog interface connected the ELSD electronically to the on-line computer. TAG species were separated by nonaqueous reverse-phase HPLC on a Beckman/Altex (San Ramon, Calif.) Ultrasphere ODS 51μm (4.6 mm×25 cm) column. The mobile phase was comprised of acetronitrile (A) and acetone (B) with a gradient profile as follows: initial conditions (A/B) 60:40 at a flow rate of 1.3 mL/min. held for 4 min., then 30:70 (A/B) at a flow rate of 1.5 mL/min. held for 8.5 min., 50:50 (A/B) at 1.5 mL/min. for 5.5 min., and then brought back to 60:40 (A/B) at 1.3 mL/min. Tricaprin was the internal standard.

Product identification was based on polarity, equivalent carbon number (ECN), and by use of TAG standards as previously described in Akoh and Huang, *J. Food Lipids*, 2:219–230 (1995). For identification of fatty acid species at the sn-2 position of the TAG, samples were spotted on thin-layer chromatography (TLC) plates along with standards and developed in petroleum ether/diethyl ether/acetic acid (90:10:1, vol/vol/vol). TAG bands were visualized under ultraviolet (UV) radiation after spraying the plate with 0.2% 2,7-dichlorofluorescein in methanol. TAG bands were scraped, pooled, and eluted with ethyl ether. Pancreatic lipase analysis was carried out according to the method described by Luddy, et al., *J. Am. Oil Chem. Soc.*, 41:693–696 (1964).

After pancreatic lipase hydrolysis, the products were extracted with ethyl ether, filtered and dried over anhydrous sodium sulfate. Products were separated by silica gel (TLC) with hexane/diethyl ether/acetic acid (50:50:1, vol/vol/vol). The sn-2 monoacylglycerol (MAG) was scraped and propylated with 6% HCl in propanol at 75° C. for 2 hours. The propyl esters were extracted with hexane and 0.1 M KCl solution. To establish the accuracy of the pancreatic hydrolysis method for sn-2 positional analysis, a TAG standard with known structure, 1,3 distearoyl-2-oleoyl-glycerol, was similarly analyzed except that the standard was dissolved in 0.5 mL hexane prior to hydrolysis. This was done because the standard was not soluble in the assay buffer. The fatty acid composition of the MAG band was determined in a Hewlett-Packard 5890 gas chromatograph, equipped with a flame-ionization detector (FID) and operated in a splitless mode. Helium was the carrier gas, and the total gas flow rate was 24 mL/min. The oven temperature was 70° C. initially and held for 4 min., and then programmed to 210° C. at 10° C./min. and held isothermally for 10 min. Heptadecanoic acid was the internal standard. The mol % of the fatty acid propyl esters were analyzed and integrated by an on-line computer.

RESULTS AND DISCUSSION

Lipase screening. Nine commercially available lipases from different sources were screened by incubating 7.3 mg of lipase with a 1:2:2 mole ratio of triolein, caproic acid, and butyric acid at 55° C. for 24 hour. The enzymes screened were lipase G, PS, L, N, AK, AY-30 (Amano Enzyme Co.), and IM 20, IM 60, and SP 435 (Novo Nordisk Biochem North America Inc., Franklinton, N.C.). IM 20, IM 60, and SP 435 and, to a limited extent, lipase AK incorporated short-chain fatty acids into triolein. Lipase G from Penicillium sp. has been shown to attached LCFA acids to glycerol to form MAG, but we now found that it was not efficient in incorporating butyric and caproic acids into triolein. IM 60 lipase from *R. miehei* produced 32% disubstituted (SLS) and 45% monosubstituted (LLS) TAG. IM 60 lipase was used further in this study because of its relative activity at the conditions described above and specificity for the sn-1 and sn-3 positions of TAG.

Mole ratio. A substrate mole ratio study was done by varying the mole ratio of triolein to butyric and caproic acids, respectively, from 1:1:1 to 1:12:12 (FIG. 1). The enzyme amount was kept constant at 7.3 mg instead of being kept at 10% by weight of total substrates. The mol % of SL formed increased with increasing mole ratio, up to a mole ratio of 1:4:4. A yield of 49% SLS and 38% LLS structured TAG was obtained at a mole ratio of 1:4:4. Hydrolysis was not a significant event in these reactions. Less than 5% of diacylglycerol was detected at this level (small scale) of assay. All yield calculations were based on the amount of SL formed and the unreacted triolein (LLL). This mole ratio was used for the remainder of the study. Beyond 1:4:4 ratio, an increase in unreacted triolein was observed.

Temperature effect. Adequate temperature control is important for the reproducible assay of enzyme-catalyzed reactions. Temperature changes can affect parameters, such as enzyme stability, affinity of enzyme for substrate, etc. The effect of temperature on the transesterification of triolein with butyric and caproic acids was studied. Mole ratio, incubation time, and solvent were kept constant at 1:4:4 (triolein, butyric acid, and caproic acid, respectively), 24 hours, and 1.5 mL of hexane, respectively. Reaction temperatures were varied from 25 to 65° C. 55° C. was most preferable for the reaction (FIG. 2). At 55° C., 12.4% LLL remained unreacted, and 44% of LLS and 43% of SLS TAG were produced. As temperature increased, there was more disubstituted TAG, but a decrease was observed above 55° C.

Time course. Time-course studies (FIG. 3) indicated that incorporation of caproic and butyric acids increased steadily with increasing incubation but later dropped after 48 hours of incubation. The mol % of SLS TAG increased to 40% at 24 hours. After 48 hours of incubation, only a moderate further increase (15%) of the disubstituted SL product (SLS) was observed. These results indicate that incorporation was more rapid in the first 24 hours than in the second 24 hours. As the concentration of LLL in the reaction mixture dropped, the concentration of disubstituted TAG (SLS) increased. For the purposes of this study, a 24-hour reaction time was selected for further experiments.

Enzyme load. FIG. 4 shows that the SL yield increased with enzyme concentration up to 10% by weight of reactants. Thereafter, there were no significant increases in the SL yield, indicating that a lipase content of 10% was suitable in this study.

Reaction media. When lipases are placed in organic solvents, they can exhibit a number of novel properties, such as altered stereoselectivity, enhanced stability, and altered mode of catalysis. Compounds that are soluble in organic solvents become potential substrates for lipases. Previous reports suggest that the interaction between organic solvents and enzyme-bound water controls the activity of an enzyme and that a physical disruption of the enzyme bound water results in enzyme deactivation. Nonpolar solvents, such as toluene and hexane, are incapable of containing large amounts of soluble water, and are therefore unable to strip away substantial amounts of water from enzymes. It is shown hereon that nonpolar solvents, such as hexane and isooctane, gave higher yields of SL than polar solvents, such as acetone and acetonitrile. Hexane and isooctane gave disubstituted TAG yields of 49 and 53%, respectively (Table 1). With petroleum ether, the amount of unreacted LLL was not much different from the unreacted amount when the reaction was performed in hexane and isooctane. The amount of disubstituted TAG was 32% in petroleum ether.

Pancreatic lipase study. IM 60 lipase from *R. miehei* preferentially hydrolyzes the fatty acids at the sn-1 and 3 positions of TAG. This characteristic is especially desirable when the nutritional benefits of TAG are considered, largely because specialty oils with desired fatty acids at specific positions can be prepared with sn-1,3 specific lipases. In this study, a pancreatic lipase hydrolysis was performed to determine the fatty acid composition of the sn-2 position of this molecule. Analysis of the SL products indicated that only oleic acid could be found at the sn-2 position. No butyric or caproic acid was found at the sn-2 position. This indicates that under the conditions of this assay, IM 60 lipase from *R. miehei* retained its sn-1,3 selectivity. The SL prepared in this study are potentially useful as reduced-calorie oils. These SLs contain desirable functional fatty acids in the same molecule and may provide rapid delivery of energy.

TABLE 1

Effect of Organic Solvents as Reaction Media on Lipase-Catalyzed of Butyric and Caproic Acids into Triolein with IM 60 Lipase as Biocatalyst

| Solvent[a] | Water content[b] (ppm) | Log P value[c] | Mol %[d] | | |
|---|---|---|---|---|---|
| | | | LLL | LLS | SLS |
| Petroleum ether | 124 | — | 5.6 | 62.1 | 32.3 |
| Isooctane | 40 | 4.51 | 4.7 | 42.1 | 53.2 |
| n-Hexane | 35.5 | 3.50 | 5.9 | 45.1 | 49.0 |
| Toluene | 119 | 2.50 | 84.7 | 10.0 | 5.3 |
| Benzene | 156 | 2.00 | 9.56 | 4.4 | N/A[e] |
| Acetone | — | −0.23 | 100 | N/A | N/A |
| Acetonitrile | 524.7 | −0.33 | 100 | N/A | N/A |

[a]Solvents were dried over molecular sieve 4 Å.
[b]The water content of the solvents was measured with a 684 KF coulometer, equipped with a 649 stirrer (Brinkmann Instrument, Inc., Westbury, NY).
[c]Sources: Laane, et al., Biotech. Bio-eng., 30:81–87 (1987); Manjor, et al., Biotechnol. Lett., 13:339–344 (1991).
L designates long-chain fatty acid (18:1n-9), and S short-chain fatty acid ($C_{6:0}$, $C_{4:0}$); LLL, triolein (unreacted); LLS, monosubstituted structured lipid; and SLS, disubstituted structured lipid.
[e]N/A indicates no structured lipid formation.

EXAMPLE 2

LIPASE CATALYZED MODIFICATION OF BORAGE OIL: INCORPORATION OF CAPRIC AND POLYUNSATURATED ACIDS TO FORM STRUCTURED LIPID

In this example, gamma-linolenic rich oil is modified with medium chain and n-3 fatty acids.

MATERIALS AND METHODS

Materials. Borage oil, porcine pancreatic lipase and capric acid (10:0, 99% pure) were obtained from Sigma Chemical Co. (St. Louis, Mo.). Immobilized sn-1,3 specific lipase, IM 60, and non-specific lipase, SP 435, were provided by Novo Nordisk Biochem North America Inc. (Franklinton, N.C.). Eicosapentaenoic acid, 20:5n-3 or EPA (45% pure) was supplied by Callanish Ltd. (Scotland, UK). All solvents were analytical grade and were obtained from Aldrich Chemical Co. (Milwaukee, Wis.).

Enzymatic modification reaction. Unless otherwise specified, for general modification of borage oil, the reaction mixtures for acidolysis consisted of borage oil (100 mg), 20:5n-3 (76 mg), 10:0 (40 mg) (mole ratio 1:2:2, respectively) with 10% of enzyme (w/w of substrates) and 5% water in 3 mL hexane. The suspension which resulted was agitated in an orbital shaker at 55° C. for 24 hours at 200 revolutions/minute. Molecular sieves 4 Å were added after two hours. All reactions were in duplicate.

Analysis of products. The enzyme was filtered through an anhydrous sodium sulfate column. The triacylglycerols (TAG) were isolated from the modified borage oil by preparative thin-layer chromatography (TLC) on silica gel 60 plate with petroleum ether/ethyl ether\acetic acid (90/10/1, vol/vol/vol) as developing solvent. The bands were visualized under ultra-violet light after spraying with 0.2% dichlorofluorescein in methanol. Bands corresponding to TAG were scraped from the TLC plate and methylated with 3 mL of 6% HCl in methanol solution at 70–80° C. for two hours. The fatty acid methyl esters (FAME) were extracted twice with 2 mL hexane, dried over sodium sulfate, and concentrated under nitrogen. An HP 5890 Series II gas-liquid chromatograph (GLC, Hewlett-Packard, Avondale, Pa.) equipped with a DB-225 fused silica capillary column 30 m×0.25 mm i.d. (J & W Scientific, Folsom, Calif.) and FID detector was used for the analysis of fatty acid composition. The injector and detector temperatures were 250 and 260° C., respectively. The column temperature was held at 190° C. for five minutes and then programmed to 215° C. at 20° C./min. Helium was the carrier gas, and the total gas flow was 23 mL/min. The relative content of FAME as mol % was quantitated by an on-line computer with heptadecanoic acid (17:0) as internal standard.

sn-2 position fatty acid. The distribution of fatty acids at the sn-2 position of borage oil triacylglycerols was determined by a modified method of Luddy, et al., supra. TAG of borage oil were isolated from TLC and hydrolyzed with porcine pancreatic lipase, and the resulting 2-monoacylglycerols after developing the TLC plate with hexane/ethyl ether/acetic acid (50:50:1, vol/vol/vol) were isolated, methylated and analyzed as FAME by GLC.

RESULTS AND DISCUSSION

Transesterification (acidolysis) reactions catalyzed by sn-1,3 specific IM 60 and non-specified SP 435 lipases were carried out with a 1:2:2 mole mixture of borage oil, 20:5n-3, and 10:0 in hexane for 24 hours. The fatty acid composition of borage oil and modified products at various substrate mole ratios are given in Table 2 (shown at the end of this example). Results show that the incorporation of 20:5n-3 was almost similar in both reactions, 10.2% with IM 60 and 8.8% with SP 435, but the incorporation of 10:0 was higher with IM 60 (26.3%) than with SP 435 (15.5%).

After transesterification, the total n6 PUFA fatty acids content of borage oil triacylglycerols decreased by 21.5 and 14.7%, respectively, with IM 60 and SP 435, while saturated fatty acids increased, respectively, by 17.4 and 10.5%. Overall, both reactions led to reduction in the n-6 PUFA and an increase in saturated fatty acids and incorporation of 20:5n-3 and medium-chain fatty acids (10:0).

Time course is a factor in monitoring the progress of enzymatic reactions by determining the shortest time necessary to obtain good yields and for minimizing the overall production cost for the process. The rates of transesterification given in FIG. 5 show that as incubation time increased, 20:5n-3 and 10:0 incorporation into triacylglycerols of borage oil increased. EPA and capric acid incorporation increased rapidly at an early stage of the reaction, between 10 and 16 hours for both enzymes, but the optimum incorporation occurred around 40 hours.

Mole ratio of substrates (TAG:acyl donors, 20:5n-3 and 10:0) and enzyme load also affected mol % incorporation of 20:5n-3 and 10:0. Mol % incorporation increased as the mole ratio (Table 2) and enzyme load (FIG. 6) increased. For IM 60 lipase, the largest increase in 10:0 (5.3%) occurred between a mole ratio of 1:2:2 and 1:3:3 while the 20:5n-3 (5.5%) increase occurred between 1:1:1 and 1:2:2. This reaction was also performed in other solvents such as isooctane, pentane, hexane, toluene, acetone and acetonitrile and found higher incorporation of 10:0 and 20:5n-3 with hexane and isooctane with both enzymes (Table 3, shown at the end of this example). These two solvents with high log P values (Laane, et al., Supra), defined as the partition coefficient between water and octanol showed high biocatalytic activity than solvents with medium log P values such as pentane and toluene, and solvents with low log P values, acetone and acetonitrile. Incorporation of 20:5n-3 and 10:0 decreased with a decrease in log P value or an increase in polarity.

It has been reported that some amount of water is necessary for maintaining the three-dimensional structure of enzymes; however, excess water usually leads to hydrolysis. FIG. 7 shows that the incorporation of 20:5n-3 and 10:0 decreased when water was added to the reaction mixture containing SP 435 and increased when added to IM 60.

Thus, IM 60 lipase tolerated more water during this acidolysis reaction than SP 435 lipase.

The use of an sn-1,3 specific lipase apparently ensures modification of the acyl composition of triacylglycerols exclusively at the sn-1 and sn-3 positions yielding products that cannot be obtained by conventional transesterification using chemical catalysts. It also appears that triacylglycerols having unusual structures seldom occur in nature and can only be prepared by transesterification of common fats and oils using lipases. For instance, triacylglycerols containing 20:5n-3 and 10:0 at the sn-1,3 positions and 18:3n-6 at the sn-2 position using IM 60 and 20:5n-3, 18:3n-6, and 10:0 at the sn-2 position using SP 435, which rarely occur in nature can easily be obtained by transesterification of MCFA and n-3 PUFA (Table 4, shown below). Such triacylglycerols are of interest as dietetic products, since fatty acids, 20:5n-3 and 10:0, at the sn-1,3 position would be rapidly released by the pancreatic lipase of most mammalian origins and 20:5n-3 would be available as an essential fatty acid in addition to 18:2n-6. The absence of 20:5n-3 and 10:0 at the sn-2 position of modified borage oil catalyzed by IM 60 demonstrates the assay conditions utilized hereon, this enzyme acted as an sn-1,3 specific lipase. On the other hand, SP 435 acted as a non-specific lipase leading to the incorporation of some 20:5n-3 and 10:0 at the sn-2 position with a concomitant decrease in 18:3n-6 at this position.

These results demonstrate that borage oil, rich in 18:3n6 and poor in n-3 PUFA, can be modified to incorporate both 20:5n-3 and 10:0 in the glycerol molecules. This modified or re-structured borage oil can be useful in the treatment of certain clinical disorders, which at present involves use of individual sources of 18:3n-6, 20:5n-3 and MCPA, or physical mixtures. SL enzymatically obtained from borage oil can also be used to ameliorate inflammatory response and modulate eicosanoids biosynthesis. These SL also provide essential fatty acids (18:2n-6, 18:3n-6, and 20:5n-3) as well as 10:0 for quick energy, and can be used as a dietary fat in the treatment of lipid or triacylglycerol malabsorption disorders.

TABLE 2

Fatty Acid Profile (Mol %) of Unmodified and Modified Borage Oil Catalyzed
by IM 60 and SP 435 Lipases at Different Substrate Mole Ratios[a]

| Substrate mole ratio | Lipase | Fatty Acids | | | | | | | | | | |
|---|---|---|---|---|---|---|---|---|---|---|---|---|
| | | 10:0 | 16:0 | 18:0 | 18:1 n-9 | 18:2 n-6 | 18:3 n-6 | 20:1 n-9 | 20:5 n-3 | Total n-6 | Total n-3 | Total saturated |
| 1:1:1 | IM 60 | 21.5 | 8.3 | 3.2 | 16.5 | 28.7 | 17.1 | ND[b] | 4.7 | 45.8 | 4.7 | 33.0 |
| | SP 435 | 12.7 | 13.4 | 3.6 | 16.8 | 32.7 | 17.7 | ND | 3.1 | 50.4 | 3.1 | 29.7 |
| 1:2:2 | IM 60 | 26.3 | 7.6 | 2.4 | 16.3 | 20.7 | 16.5 | ND | 10.2 | 37.2 | 10.2 | 36.3 |
| | SP 435 | 15.5 | 10.4 | 3.5 | 17.5 | 26.9 | 17.1 | ND | 8.8 | 44.0 | 8.8 | 29.4 |
| 1:3:3 | IM 60 | 31.6 | 7.2 | 2.1 | 15.4 | 32.3 | 14.0 | ND | 11.4 | 46.3 | 11.4 | 40.9 |
| | SP 435 | 14.7 | 9.8 | 2.0 | 15.0 | 34.4 | 15.1 | ND | 9.0 | 49.5 | 9.0 | 26.5 |
| Unmodified | borage oil | ND | 14.6 | 4.3 | 19.2 | 38.6 | 20.1 | 3.2 | ND | 58.7 | ND | 18.9 |

[a]Mole ratio of borage oil:20:5n-3:10:0. The reaction was performed in the presence of 5% added water and 10% (w/w of substrates) of lipase. Incubation was at 55° C. for 24 hours.
[b]ND = not detectable.

TABLE 3

Effect of Organic Solvent on the Mol % Incorporation of
20:5n-3 and 10:0 into Borage Oil[a]

| Log P value Fatty Acid | Lipase | Hexane 3.5 | Isooctane 4.5 | Pentane 3.0 | Toluene 2.5 | Acetone −0.23 | Acetonitrile −0.33 |
|---|---|---|---|---|---|---|---|
| 10:0 | IM 60 | 26.3 | 27.1 | 12.3 | 11.0 | 5.3 | 3.4 |
| | SP 435 | 15.5 | 14.2 | 6.5 | 6.1 | 2.4 | 2.0 |
| 20:5n-3 | IM 60 | 10.2 | 9.8 | 5.7 | 5.2 | 3.9 | 3.5 |
| | SP 435 | 8.8 | 6.7 | 3.5 | 4.3 | 3.0 | 1.8 |

[a]Mole ratio of borage oil:20:5n-3: 10:0 = 1:2:2. See Table 2 for reaction conditions.

TABLE 4

Analysis of the Fatty Acid at the sn-2 Position of Unmodified and Lipase Modified Borage Oil[a]

| | Fatty acid at the sn-2 position (Mol %) | | | | | | | | | | |
|---|---|---|---|---|---|---|---|---|---|---|---|
| | 10:0 | 16:0 | 18:0 | 18:1 n-9 | 18:2 n-6 | 18:3 n-6 | 20:1 n-9 | 20:5 n-3 | Total n-6 | Total n-3 | Total saturated |
| Unmodified borage oil | ND[b] | 3.9 | 2.1 | 23.1 | 46.7 | 20.2 | ND | ND | 66.9 | ND | 6.0 |
| IM 60 modified borage oil | ND | 5.2 | 1.7 | 22.1 | 49.1 | 21.9 | ND | ND | 71.0 | ND | 6.9 |
| SP 435 modified borage oil | 7.5 | 6.0 | 1.9 | 15.2 | 49.7 | 14.5 | ND | 5.2 | 64.2 | 5.2 | 15.0 |

[a]Mole ratio of borage oil:20:5n-3:10:0 = 1:2:2.
[b]ND = not detectable.

EXAMPLE 3

EFFECTS OF SELECTED SUBSTRATE FORMS ON THE SYNTRESIS OF STRUCTURED LIPIDS BY TWO IMMOBILIZED LIPASES

Linoleic acid is an essential fatty acid. It is not synthesized by humans and must be obtained from the diet. Medium-chain TAG have been reported to possess several health benefits. Thus, SL that contain both linoleic acid and medium-chain fatty acids in the same glycerol molecule are of interest and are produced herein. In this example, SL were synthesized from tricaprin and trilinolein.

MATERIALS AND METHODS

Materials. Tricaprin (1,2,3-tridecanoylglycerol), trilinolein (1,2,3-tri-[(cis,cis)-9,12-octadecadienoyl]glycero), tristearin (1,2,3-trioctadecanoylglycerol), capric acid ethyl ester, 1,3 distearoyl-2-oleoyl-glycerol, and porcine pancreatic lipase (Type II, crude) were purchased from Sigma Chemical Co. (St. Louis, Mo.). Immobilized enzymes SP 435 and IM 60 were provided by Novo Nordisk Biochem North America Inc. (Franklinton, N.C.). Organic solvents were obtained from Fisher Scientific (Norcross, Ga.). $AgNO_3$—TLC plates (20% $AgNO_3$/silica gel) were purchased from Alltech Associates, Inc. (Deerfield, Ill.).

Enzymatic interestification reactions. To compare the selectivity of lipases for tricaprin and capric acid ethyl ester as substrates to synthesize SL from trilinolein, immobilized enzymes (SP 435 and IM 60, 40% of the total weight of reactants) were added to a 1:1 mole ratio of trilinolein (100 mg) to tricaprin (63) mg or a 1:3 mole ratio of trilinolein (100 mg) to capric acid ethyl ester (68 mg) in 3 mL hexane in a screw-cap tube, respectively. The reactions were incubated at 55° C. in an orbital shaking water bath for 12 hours at 200 rpm. Samples (17 μL) were withdrawn from the reaction mixture, mixed with 10 μL of internal standard solution (triolein, 10 mg/mL in hexane), and diluted to 1 mL with an acetone/acetonitrile (A/ACN) (50:50, vol/vol) mixture for high-performance liquid chromatography (HPLC) analysis.

To compare the selectivity for chainlength between tricaprin and tristearin in the synthesis of SL from trilinolein, a 1:1 mole ratio of trilinolein (100 mg) to tristearin (120 mg) or tricaprin (63 mg) was mixed with 40% (total weight of reactants) inmobilized enzymes in 3 nL hexane and incubated at 55° C. for 12 hours at 200 rpm. Samples were collected and prepared for HPLC as described above, except that a mixture of A/chloroform (15:85, vol/vol) was used to dilute and to solubilize tristearin.

HPLC analysis. TAG molecular species were analyzed by HPLC with a Hewlett-Packard 1090 Win liquid chromatographic system (Hewlett-Packard, Avondale, Pa.), fitted with a reversed phase Ultrasphere® ODS 5 μm spherical 80 Å pore (4.6 mm×250 mm) column (Beckman Instruments, Inc., Fullerton, Calif.). The reactants and product were quantitated on-line with an evaporative light-scattering detector (ELSD) (Sedex 45; Richard Scientific, Novato, Calif.). The ELSD was set to 40° C. at a nebulizer gas ($N_2$) pressure of 2.1 atm and a gain of 10. The injection volume was 20 μL, and the column oven temperature was 40° C. A mobile-phase gradient of ACN and A was used as described in Table 5 (shown below).

$AgNO_3$-TLC. $AGNO_3$-TLC plates were used to separate TAG according to their unsaturation. A 1:1 mole ratio of tricaprin and trilinolein was interesterified with immobilized enzymes (IM 60 or SP 435, 40% of total weight of reactants) under the conditions described above. After removing the enzyme by passage through an anhydrous sodium sulfate column, the mixture was analyzed by $AgNO_3$-TLC. Each mixture was spotted several times to obtain enough TAG for further analysis. The mobile phase was a mixture of chloroformn/benzene (90:10, vol/vol). The bands were visualized, after spraying with 0.2% 2,7-dichlorofluorescein in methanol, under ultraviolet (UV) light. The bands corresponding to TAG, SL1 (containing one linoleic acid) and SL2 (containing two linoleic acids), were scraped and pooled for further analysis. These TAG were extracted twice with diethyl ether and centrifuged (1000 rpm×1 min.).

TABLE 5

The High-performance Liquid Chromatography Mobile Phase Gradient

| Time (min.) | $ACN^a$ (%) | $A^a$ (%) | Flow rate (mL/min.) |
|---|---|---|---|
| 0 | 50 | 50 | 1.8 |
| 12.5 | 5 | 95 | 2 |
| 13.0 | 50 | 50 | 1.8 |
| 18.0 | 50 | 50 | 1.8 |

$^a$ACN, acetonitrile; A, acetone.

Hydrolysis by pancreatic lipase. The hydrolysis condition was slightly modified from the method described by Yoshida and Alexander, Nutr. Rep. Int., 26:655–665 (1982). After evaporating all solvents, 1 mL of I M Tris-HCl buffer (p)H 7.6), 0.25 mL of bile salt solution, 0.1 ml of 2.2% $CaCl_2$ solution, and 8 mg of pancreatic lipase wetre mixed and incubated at 37° C. for 2 min., followed by vigorous vortex (2 min.), centrifugation (1900 rpm, 3 min.), extraction with 3 mL of diethyl ether (two times) and elution through an anhydrous sodium sulfate column. Prolonged incubation time may cause acyl migration within the TAG molecule. Extraction of sn-2 monoacylglycerol and methylation for gas chromatography (GC) analysis was performed as described in Lee and Akoh, J. Am. Oil Chem. Soc., 73:611–615 (1996). Pancreatic lipase hydrolysis method was validated by incubating a solution of 1,3-distearoyl-2-oleoylglycerol standard in hexane under the same condition and analyzing the fatty acid at the sn-2 position. GC analysis. For fatty acid composition, a Hewlett-Packard 5890 Series II gas chromatograph equipped with a flame-ionization detector (Hewlett-Packard) was used. A fused-silica capillary column (DB-255, 30 m×0.25 mm i.d.; J&W Scientific, Folsom, Calif.) was used. The temperature was programmed (initial temperature: 120° C. hold for 3 min., final temperature: 215° C. hold for 10 min., rate: 10° C./min.). The injector and detector temperatures were 250 and 260° C., respectively.

RESULTS AND DISCUSSION

FIG. 8 shows the HPLC reverse-phase separation of the TAG molecular species according to polarity and total carbon number. The identity of each molecular species was established based on Akoh and Huang, supra. Each peak was collected at predetermined retention time and analyzed by GC after methylation. Fatty acid composition at the sn-2 position. $AgNO_3$—TLC indicated that the more unsaturated TAG (trilinolein) showed the least migration. SL1, with one linoleic acid and two capric acids, has less unsaturation and migrated higher on the $AgNO_3$ plate than SL2, which contains two linoleic acids. The $R_f$ (×100) values were 51.5 for tricaprin, 29.1 for SL with one linoleic acid (SL1), 12.1 for SL with two linoleic acids (SL2), and 3 for trilinolein.

It has been reported that the fatty acid at the sn-2 position is easily absorbed, e.g., Quinlan and Moore, INFORM, 4:580–585 (1993). Thus, the study of the fatty acid profile at the sn-2 position is useful for further metabolic studies. Using TAG substrate forms and IM 60 and SP 435, linoleic acid is present at the sn-2 position from both the first and second steps. For example, see the schematic shown in FIGS. 9A and 9B which show the interesterification between trilinolein and tricaprin with (A) IM 60, or (B) SP 435. After GC analysis, the fatty acid composition at the sn-2 position was determined (Table 6, shown below). With IM 60, 57.7 mol % capric acid and 42.3 mol % linoleic acid were obtained at the sn-2 position for SL1 and 43.3 mol % capric acid and 56.7 mol % linoleic acid were obtained for SL2. On the other hand, the fatty acids at the sn-2 position with SP 435 were 43.6 mol % capric acid and 56.4 mol % linoleic acid for SL1 and 56.6 mol % capric acid and 43.4 mol % linoleic acid for SL2, respectively (Table 6, shown below). Confirmation of the hydrolysis method was achieved with a known molecule, 1,3-distearoyl-2-oleoyl-glycerol which gave only oleic acid at the sn-2 position. Possible products from a reaction between capric acid ethyl ester and trilinolein are illustrated in FIGS. 10A (IM 60) and 10B (SP 435).

TABLE 6

Fatty Acid Positional Analysis of Structured Lipids Synthesized by Interesterification of Tricaprin and Trilinolein Catalyzed by Immobilized Lipases

| | Fatty acid at the sn-2 position (Mol %) | | | |
|---|---|---|---|---|
| | SL1[a] | | SL2[a] | |
| Enzyme | Capric acid | Linoleic acid | Capric acid | Linoleic acid |
| IM 60 | 57.7 | 42.3 | 43.3 | 56.7 |
| SP 435 | 43.6 | 56.4 | 56.6 | 43.4 |

[a]SL1: structured lipid containing one linoleic acid and two capric acid molecules;
SL2: structured lipid containing two linoleic acid and one capric acid molecules.

Selectivity between tricaprin and capric acid ethyl ester forms. The results of the course studies of interesterification between trilinolein and tricaprin or capric acid ethyl ester are illustrated in FIGS. 11A and 11B. IM 60 showed a more rapid reaction than SP 435. Most of the interesterification occurred within the first 2 hours with IM 60 as the biocatalyst (FIG. 11A). With SP 435, the interesterification was slow and continued throughout the 12-hour reaction (FIG. 11B). The amount of SL1 produced with capric acid ethyl ester was less than with tricaprin up to at least 23 hours with IM 60. After 24 hours, the amount of SL1 was 32.1 mol % with capric acid ethyl ester and 31.6 mol % with tricaprin. Capric acid ethyl ester as substrate produced more SL2, compared to tricaprin, up to 12 hours with IM 60. After 24 hours, less SL2 was produced with capric acid ethyl ester (50.9 mol % with capric acid ethyl ester and 58.9 mol % with tricaprin.

Interesterification is initiated by hydrolysis of an ester bond and the formation of an acyl-enzyme intermediate, followed by exchange of the acyl moiety and new ester bond formation. If capric acid ethyl esters are used as acyl donor for trilinolein to produce SL, SL2 is first produced and then used for the synthesis of SL1 (FIGS. 10A and 10B). When tricaprin is used as substrate, both SL1 and SL2 can be produced in the first step, then used as substrates for further conversions before reaching equilibrium (FIGS. 9A and 9B). Overall production of SL (total mol % of synthesized SL1 and SL2) with IM 60 was greater with tricaprin than with capric acid ethyl ester during 12 hours of incubation. Tricaprin was a better interesterification substrate with trilinolein than capric acid ethyl ester for the production of SL1 and SL2 with SP 435 (FIG. 11B). More SL was produced with tricaprin than with capric acid ethyl ester with both enzymes (IM 60 and SP 435). Additionally, Table 7 shows that tricaprin was more rapidly used for synthesis of SL1 and SL2 than trilinolein with IM 60 and SP 435. Because most of the reaction occurred during the first 2 hours with IM 60, the values did not change much after 2 hours (steady state). But during the first 2 hours, IM 60 showed preference toward tricaprin, resulting in a more rapid consumption than trilinolein. SP 435 showed an apparent preference toward tricaprin, compared with trilinolein, during the reaction.

TABLE 7

Mol % of Unreacted Substrates During Interesterification Reaction Between Tricaprin and Trilinolein with IM 60 and SP 435 Lipases[a]

| Enzymes | Substrate | 2 hr | 4 hr | 6 hr | 8 hr | 10 hr | 12 hr |
|---|---|---|---|---|---|---|---|
| IM 60 | Tricaprin | 11.2 | 7.8 | 7.4 | 7.7 | 8.3 | 8.1 |
| | Trilinolein | 20.3 | 9.0 | 12.1 | 9.6 | 9.0 | 7.6 |
| SP 435 | Tricaprin | 29.6 | 23.4 | 20.0 | 14.3 | 12.1 | 11.1 |
| | Trilinolein | 60.2 | 52.4 | 40.2 | 33.1 | 22.7 | 19.5 |

[a]After the reaction, mol % of unreacted substrates were obtained along with mol % of synthesized structured lipids.

Selectivity with regard to substrate chainlength. FIGS. 12A and 12B show the selectivity of IM 60 and SP 435 with regard to substrate chainlength. IM 60 showed a more rapid reaction with tricaprin than with tristearin, because structured lipids (SL1 and SL2) were more rapidly synthesized and reached steady state in 4 hours (FIG. 12A). After 2 hours, the amount of SL1 and SL2 synthesized with tricaprin were 1.5 and 4.6 times, respectively, compared with tristearin. Most reaction with tricaprin occurred within 2 hours. But with tristearin, the reaction was slower, reaching equilibrium in 6 hours. Total mol % of synthesized SL were also greater with tricaprin than with tristearin before 4 hours, indicating that short-chain fatty acids were rapidly reacted to produce SL. After 12 hours of reaction, the amount of SL1 and SL2 with tricaprin was 38.8 and 52.8 mol %, respectively. With tristearin, 44.4 and 46.1 mol % of SL1 and SL2 were obtained, respectively. Tristearin did not fully dissolve in hexane at room temperature, but at the reaction temperature, 55° C., it was fully dissolved.

SP 435 showed somewhat different results (FIG. 12B). This enzyme did not show a preference for either substrate (tricaprin and trilinolein) at the early stages. After 12 hours, the mol % of SL1 and SL2 from tristearin were approximately 41.3 and 38.9%, respectively, and 45.8% for SL2 and 32.1% for SL1 with tricaprin. In addition, tristearin was more rapidly used than trilinolein within the first 2 hours, even though trilinolein was used for synthesis of SL after that period (Table 8). This is surprising since others have reported that some lipases tend to prefer unsaturated substrates, see, e.g., Brisson, *Lipids in Human Nutrition*. Jack K. Burgess, Inc., Englewood, 65–70 (1981). Overall, IM 60 showed more rapid interesterification than SP 435 (FIGS. 12A and 12B).

TABLE 8

Mol % of Unreacted Substrates During Interesterification Reaction Between Tristearin and Trilinolein with IM 60 and SP 435 Lipases[a]

| Enzymes | Substrate | 2 hr | 4 hr | 6 hr | 8 hr | 10 hr | 12 hr |
|---|---|---|---|---|---|---|---|
| IM 60 | Tristearin | 27.5 | 20.5 | 18.7 | 19.4 | 13.0 | 12.5 |
| | Trilinolein | 49.9 | 27.3 | 10.0 | 8.1 | 8.5 | 8.2 |
| SP 435 | Tristearin | 36.7 | 42.0 | 37.2 | 28.0 | 21.3 | 19.1 |
| | Trilinolein | 55.3 | 35.8 | 31.0 | 25.1 | 21.2 | 16.0 |

[a]After the reaction, mol % of unreacted substrates were obtained along with mol % of synthesized structured lipids.

From this study, it seems that SP 435 has a preference to some degree for the TAG form. IM 60 reacted better with tricaprin than with capric acid ethyl ester for the overall synthesis of SL. Thus, more SL were synthesized with the TAG substrate form than with the ethyl ester form of capric acid. SP 435 exhibited no apparent preference for either tricaprin or tristearin because total mol % of synthesize SL1 and SL2 were similar. But with IM 60 and tricaprin as substrate, SL1 and SL2 were produced more rapidly and reached steady state faster than with tristearin as substrate. Additionally, tricaprin was more rapidly consumed than trilinolein with both enzrnes (IM 60 and SP 435).

EXAMPLE 4

ENZYMAC SYNESIS OF STRUCTURED LIPIDS

This example shows the production of low calorie SL with specific fatty acids at the sn-1,3 positions by interesterifing tristearin (C18:0) with medium chain triacylglycerols such as tricaprin (C10:0) or tricaprylin (C8:0) with sn-1,3-specific immobilized lipase IM 60 from Rhizomucor miehei.

MATERIALS AND METHODS

Materials. Tristearin (1,2,3-trioctadecanoylglycerol), tricaprin (1,2,3-tridecanoylglycerol), tricaprylin (1,2,3-trioctanoylglycerol), and porcine pancreatic lipase (Type II, crude) were obtained from Sigma Chemical Co. (St. Louis, Mo.). Immobilized sn-1,3 specific lipase IM 60 from *Rhizomucor miehei* was obtained from Novo Nordisk Biochem North America Inc. (Franklinton, N.C.). n-Hexane and all other organic solvents were purchased from Fisher Scientific (Norcross, Ga.).

Enzymatic interesterification. Typical interesterification consisted of adding 50 mg tristearin, 31.1 mg tricaprin, 8.1 mg lipase (10% w/w of reactants), and 3 mL hexane to screw capped test tubes. The reaction mixture was incubated in a gyratory shaking water bath at 55° C. for 24 hours at 200 rpm. All reactions were in duplicate.

Extraction and analysis. After the incubation, reaction mixtures were filtered through an anhydrous sodium sulfate column to remove the enzyme and any residual water. A 50 µL aliquot of product mixture was redissolved in 950 µL acetone:acetonitrile (50:50 vol/vol) and 50 µL trilaurin (C12:0) added as internal standard. Products were analyzed with a Hewlett-Packard (Avondale, Pa.) 1090 Win high performance liquid chromatograph (HPLC) equipped with a Sedex 45 evaporative light scattering detector, ELSD (Richard Scientific, Novato, Calif.).

The ELSD was set to 45° C., a nebulizer gas pressure of 2.1, and a gain of 5 for the nonaqueous reverse-phase system. A Hewlett-Packard 35900 digital A/D analog interface connected the ELSD electronically to the on-line computer. Triacylglycerols (TAG) and SL molecular species were analyzed by nonaqueous reverse-phase HPLC on a BecknanlAltex (San Ramon, Calif.) Ultrasphere ODS 5µm, (4.6 mm×25 cm) column. Separation was obtained with acetonitrile (solvent A) and acetone (solvent B) as eluent, with the following gradient profile: initial condition 50:50 (A/B) at a flow rate of 1.8 mL/min.; brought to 5:95 (A/B) at 2 mL/min. for 12.5 min., and returned to original conditions. Total run time was 18 min.

Products were further analyzed by thin-layer chromatography (TLC) on a precoated silica gel G plates (Fisher Scientific, Norcross, Ga.), developed with petroleum ether:diethyl ether:acetic acid (90:10:1, vol/vol/vol). The bands were visualized under ultraviolet light after spraying with 0.2% 2,7-dichlorofluorescein in ethanol. Bands corresponding to TAGs were scraped, methylated in 3 mL methanolic HCL at 75° C., for 2 hours. The fatty acid methyl esters (FAME) were extracted with 2 mL hexane and 1 mL of 0.1 M KCL solution, centrifuged at 1000 rpm for 3 min. and concentrated under nitrogen.

Fatty acid composition and identification was obtained with a Hewlett-Packard 5890 Series II gas chromatograph (Hewlett-Packard, Avondale, Pa.), equipped with a flame-ionization detector (FID) and a fused-silica capillary column (DB-225, 30 m×0.25 mm I.D., J & W Scientific, Folsom, Calif.). The column was held at 120° C. for 3 min. and programmed to 215° C. for 10 min. at a rate of 10° C./min. Helium was the carrier gas, and the total flow rate was 23 mL/min. Injector and detector temperatures were set at 250 and 260° C., respectively. Heptadecanoic acid methyl ester was the internal standard and used to quantify mol % of FAME with the aid of an on-line computer.

A modified version of Luddy, et al., supra, was used to perform pancreatic lipase hydrolysis to determine the fatty acids at the sn-2 position of the SL products. At least 2 mg SL product was mixed with 1 mL of 0.4M tris-HCL buffer (pH 7.6), 0.25 mL of 0.05% bile salts, 0.1 mL of 2.2% $CaCl_2$ and 8 mg pancreatic lipase. The mixture was incubated in a 37° C. water bath for 30 sec. and vortexed vigorously. This was repeated 2 times before centrifugation at 1000 rpm for 3 min., and extracting with 3 mL ethyl ether (2 times). The extract was filtered through a sodium sulfate column and the sample concentrated to a small volume with nitrogen. The residual sn-2 monoacylglyercol (MAG) was separated by TLC on a silica gel G plate developed with hexane:diethyl ether:acetic acid (50:50:1, vol/vol/vol). Bands corresponding to the sn-2 MAG were scraped, methylated and analyzed by GC as described above.

RESULTS AND DISCUSSION

Mole ratio. FIG. 13 shows the mol % of structured lipid molecular species C41, C49, and unreacted tristearin (C57) in the reaction product after interesterification tristearin with tricaprin catalyzed by IM 60 lipase. In general, as mole ratio increased (1:1 to 1:5, tristearin:tricaprin), yields for C41 and C49 dropped (except for C41 at 1:2 mole ratio), possibly indicating inhibitory effects by tricaprin at high substrate mole ratios. The drop in yields were more noticeable for C49 than for C41.

However, the same was not observed when free capric acid was used. On the contrary, SL synthesis was enhanced as substrate mole ratio increased from 1 to 5 (tristearin:capric acid) with yields as high as 48.6 and 48.5% of C41 and C49, respectively. Previous results have shown that *Rhizomucor miehei* lipase (IM 60) has a preference for free fatty acids compared to *Candida antarctica* lipase, SP 435. Table 9 shows the SL product yields using different medium chain TAGs-tricaprin, tricaprylin, and free fatty acids, to transesterify tristearin at a 1:1 mole ratio. Comparable yields (41 and 43.5%) for the disubstituted SL (C37 and C41, respectively) molecular species were obtained with the medium chain TAG substrates. Only 2.3% of tristiearin was left unreacted when T10:0 was the substrate indicating excellent conversion to desired products. Free caprylic acid as acyl donor at 1:1 mole ratio gave better product yield than free capric acid. These results indicate that both capric and caprylic acids as well as their triacylglycerols can be used to produce high yields of desired SL with IM 60 lipase as biocatalyst.

Enzme load. Enzyme load was investigated with lipase concentrations ranging from 2–30% (w/w of reactants). A 2–10% added lipase gave high yields of desired products with 10% yielding up to 41% C41, 43.7% C49, and 4.1% C57 (FIG. 14). No major improvements were observed at greater enzyme loads.

Time course. Products were analyzed after 1, 2 ,3, 4, 5, 6, 12, 18, 24, 36, 48 and 72 hours (FIG. 15) to follow the interesterification ability of IM 60 lipase with time. For the first 5 hours, product formation was low. However, yields increased greatly for both C41 and C49 after 6 hours (33.4 and 29.4%, respectively). The reaction seemed to have reached equilibrium at 24 hours, after which there was no point in prolonging the reaction. All further experiments were conducted at 24 hours.

Effect of added water. The effect of added water on IM 60 lipase interesterification ability and 24 yields of C41 and C49 SL molecular species is shown in FIG. 16. Although it is known that a minuscule amount of water is required by enzymes to maintain their 3-dimensional structure and catalytic ability, the highest product formation was obtained under near anhydrous conditions. As the amount of water increased from 0–10% (w/w of reactants), inhibitory effects on IM 60 lipase become more noticeable, especially in the case of C49 product formation. Between 15–25% added water, an increase in yields, although small, was observed for both SL, possibly indicating water's ability to accelerate acyl migration, thus making the sn-2 or sn-3 position available for capric acid incorporation. From these results, this lipase seemed to perform best between 10–20% added water. However, the best yield for C41 species (44.3%) was obtained with zero added water.

Effect of reaction media. Organic solvents of varying log P values were chosen to study the effect of reaction media on the interesterification of tristearin and tricaprin (Table 10). Log P value, the partition coefficient between water and octanol is often used as an indicator of solvent polarity. It has been postulated that solvents with log P>4 (nonpolar solvents) allow high biocatalytic activity. The results herein show that solvents with log P>3 were the most suitable media, with heptane (log P=4, 41.6 and 44.2%), hexane (log P=3.5, 43.5 and 37.8%), and iso-octane (log P=4.5, 40.8 and 38.7%) giving the best yields for C41 and C49, respectively. Petroleum ether (no log P value reported) also gave high yields (39.0 and 47.5% for C41 and C49, respectively). Polar solvents such as chloroform (log P=2), ethyl ether (log P=0.85), and toluene (log P=2.5) gave low or no product formation. The poor yield obtained in the reaction with no solvent indicates that a mutual solvent that will allow mobility of the substrates to the enzyme active site is preferred. Tristearin is solid at room temperature and does not melt completely at 55° C. used in this reaction, and therefore, must be solubilized in a solvent. Use of higher temperatures may alternatively be used, but the resulting product yield may be reduced.

Enyme reuse. One of the advantages of enzyme reuse is that it allows for enzymes to be recovered. For this example, the enzyme was isolated from reaction products after each batch, washed with distilled water (3 times) and dried under vacuum until next use. Rinsing with hexane after water wash did not improve enzyme activity. Up to 5 runs were performed. FIG. 17 shows the experimental results. Acceptable yields were obtained for the first 4 runs. After run 5, no SL formation was detected.

Pancreatic lipase Study. Several studies have shown that the nature of the fatty acids and their positions in a glycerol molecule can affect their metabolism, availability as an energy source, and as an essential fatty acid source. Pancreatic lipase hydrolysis was performed to determine the fatty acid composition at the sn-2 position (Table 11). Values show that IM 60 lipase incorporated 21.2% C10 and 78.8% C18 at the sn-2 position. IM 60 was able to produce SL containing specific fatty acids at the sn-1,3 positions.

TABLE 9

Yields of Structured Lipid Molecular Species Produced by Transesterification of Different Substrates with Tristearin

| Substrate type | Molecular species (Mol %) | | | | |
|---|---|---|---|---|---|
| | C37 | C41 | C47 | C49 | C57 |
| TAG as acyl donor | | | | | |
| T8:0 | 41.0 | — | 44.9 | — | 9.7 |
| T10:0 | — | 43.5 | — | 37.8 | 2.3 |
| FFA as acyl donor | | | | | |
| C8:0 | 20.0 | — | 52.0 | — | 27.9 |
| C10:0 | — | 3.7 | — | 56.4 | 39.8 |

Reactions were performed with a 1:1 mole of substrates. Incubations were at 55° C., 220 rpm for 24 hours with IM 60 lipase as the biocatalyst. TAG = triacylglycerol, FFA = free fatty acids, T8:0 = tricaprilyn, T10:0 = tricaprin, C37 and C41 - disubstituted products with caprylic and capric acids, respectively, C47 and C49 = monosubstituted products with caprylic and capric acids, respectively, and C57 = unreacted tristearin. The balance of thereported mol % belong to the medium chain fatty acid or TAG.

TABLE 10

Effect of Reaction Media on Lipase-Catalyzed Interesterification of Tristearin and Tricaprin with IM 60 as Biocatalyst

| Solvent[a] | Log P[b] | Molecular species (Mol %) | | |
|---|---|---|---|---|
| | | C41 | C49 | C57 |
| No Solvent | — | 23.0 | 3.2 | 16.3 |
| Pet Ether | — | 39.0 | 47.5 | 4.0 |
| Iso-octane | 4.5 | 40.8 | 38.7 | 6.7 |
| Heptane | 4.0 | 41.6 | 44.2 | 3.0 |
| Hexane | 3.5 | 43.5 | 37.8 | 2.3 |
| Cyclohexane | 3.2 | 38.4 | 35.2 | 6.3 |
| Pentane | 3.0 | 36.9 | 44.9 | 10.7 |
| Toluene | 2.5 | 30.1 | 17.4 | 11.7 |
| Chloroform | 2.0 | — | — | 46.9 |
| Ethyl Ether | 0.85 | — | — | 59.9 |

[a]Solvents dried over molecular sieve 4 Å.
[b]Source: Laane, et al., Biotechnol. Bio-eng., 30:80–87 (1987).
See Table 9 for explanation of abbreviations.

TABLE 11 sn-2 Positional Analysis of Structured Lipid Products by Lipase = Catalyzed Interesterification of Tristearin and Tricaprin with IM 60 Lipase as Biocatalyst

| Fatty acid | GC profile (Mol %)[a] | Mol % of fatty acid at sn-2 position[b] |
|---|---|---|
| C10:0 | 35.2 | 21.2 |
| C18:0 | 64.8 | 78.8 |

[a]Fatty acid composition of structured lipids after TLC separation of products from reactants.
[b]After pancreatic lipase hydrolysis of structured lipid products.

EXAMPLE 5

LIPASE-CATALYZED INTERESTERIFICATION OF TRICAPROIN AND TRILINOLEIN

Triacylglycerol (TAG) lipases that hydrolyze TAG to diacylglycerols (DAG), monoacylglycerols (MAG), fatty acids and glycerol are utilized in this example. Specifically, the interesterification of trilinolein and tricaproin to produce structured lipids containing linoleic acid and caproic acid is shown.

MATERIALS AND METHODS

Materials. Tricaproin, trilinolein, porcine pancreatic lipase, triacylglycerol standards, and 1,3 distearoyl-2-oleoyl-glycerol were obtained from Sigma Chemical Company (St. Louis, Mo.). Immobilized lipases IM 20, IM 60 from *Rhizomucor miehei* and SP 435 from *Candida antarctica* were obtained from Novo Nordisk Biochem North America Inc. (Franklinton, N.C.). Nonspecific lipase AK from Pseudomonas sp., sn-1,3 specific lipase L from *Candida lipolytica*, lipase N from *Rhizopus niveus*, lipase PS from Pseudomonas sp., and PGE (pregastric esterase) from cow tongue root and salivary glands were kindly provided by Amano International Enzyme Co. (Troy, Va.). 20% silver nitrate plates were purchased from Alltech (Deerfield, Ill.). All solvents were of HPLC grade and were obtained from Fisher Scientific (Norcross, Ga.).

Interestenification reaction. Structured lipid synthesis was performed in screw capped test tubes. Eight lipases were screened for their ability to catalyze the interesterification reaction. For enzyme screening, a 1:1 mole ratio of trilinolein (50 mg) to tricaproin (22 mg) was incubated at 55° C. for 24 hours with 7.4 mg of enzyme. Unless otherwise specified, all other interesterification reactions typically contained a mixture of 50 mg trilinolein, 44 mg tricaproin (i.e., 1:2 mole ratio), and 9.4 mg of lipase (i.e., 10% w/w of total substrate) in 3 mL hexane previously dried over molecular sieves of 4 Å. The reaction mixture was incubated in an orbital shaking warer bath at 200 rpm, 45° C. and 55° C., for IM 60 and SP 435 catalyzed reactions, respectively. All reactions were performed in duplicate.

Determination of interestenfied products. Reaction products were cooled and filtered through a sodium sulfate column to remove any moisture and enzyme particles. Products were analyzed with a Hewlett-Packard 1090 HPLC equipped with a Sedex 45 evaporative light scattering detector (ELSD, Richard Scientific, Novato, Calif.). The ELSD was set at 40° C., a nebulizer nitrogen gas pressure of 2.1 atm and a gain of 5 for nonaqueous reverse phase system. A Hewlett-Packard 35900 digital A/D analog interface connected the ELSD electronically to the online computer. Triacylglycerol species were separated by nonaqueous reverse phase HPLC with a Beckiman/Altex (San Ramon, Calif.) Ultrasphere ODS 5 $\mu$m (4.6 mm×25 cm) column. The mobile phase consisted of acetonitrile (A) and acetone (B) with a gradient profile as follows: initial conditions (A:B) 50:50 at a flow rate of 1.8 mL/min. held for 4 min., then 5:95 (A:B) at a flow rate of 2.0 mL/min., held for 8.5 min., and then returned to the original conditions. Trilaurin as the internal standard was added to the reaction products prior to HPLC analysis. Product identification was based on polarity, total carbon number (TCN) and use of triacylglycerol standards.

Positional analysis of TAG. Structured lipids (SL) were separated by spotting samples along with standards on 20% silver nitrate thin layer chromatography (TLC) plates (Alltech Associates, Inc., Deerfield, Ill.) and developed in chloroform: benzene (85:15, v/v). SL bands were visualized under UV light after spraying with 0.2% 2,7-dichlorofluorescein in methanol. Bands corresponding to SL were scraped and eluted with diethyl ether. The composition of each band was determined by HPLC. Positional analysis of TAG was done using the pancreatic hydrolysis method of Luddy, et al. (Supra). After hydrolysis the mixture was extracted with ethyl ether, filtered and dried over anhydrous sodium sulfate. The individual products were isolated by TLC on silica gel G plates developed with hexane: ethyl ether: acetic acid (50:50:1, v/v). The sn-2 monoacylglycerol (MAG) was visualized under UW light after spraying with 0.2% 2,7-dichlorofluorescein in methanol. The monoacylglycerol (MAG) band was propylated with 6% HCl in propanol at 75° C. for 2 hours. The fatty acid propyl esters (FAPE) were extracted with hexane and 0.1M KCl solution. To establish the accuracy of the pancreatic hydrolysis method for sn-2 positional analysis, a TAG standard with known structure, 1,3 distearoyl-2-oleoyl-glycerol was similarly analyzed except that the standard was dissolved in 0.5 mL of hexane prior to hydrolysis. This was done because the standard was not soluble in the assay buffer. The fatty acid composition of the MAO band was determined using a Hewlett-Packard 5890 gas chromatograph equipped with a flame ionization detector (FID) and operated in a splitless mode. Helium was the carrier gas and the total gas flow rate was 24 mL/min. The oven temperature was 70° C. initially and was held for 4 min., then programmed to 210° C. at 100° C./min. and held isothermally for 10 min. Heptadecanoic acid was the internal standard. The fatty acid propyl esters were analyzed and integrated by an on-line computer.

RESULTS AND DISCUSSION

Lipase screening. Eight commercial lipases were screened for their ability to catalyze the interesterification of trilinolein and tricaproin. The enzymes screened were immobilized lipozyme IM 60, IM 20 and SP 435 (Novo Nordisk Biochem North America Inc., Franklinton, N.C.), uninunobilized lipase AK, PS, L, PGE and LN (Amano Enzyme Co., Troy, Va.). For simplicity, the same amount of enzyme was used irrespective of their specific activities. FIG. 18 shows that immobilized lipases IM 60, IM 20, SP 435. and unimmobilized lipases PS and AK are capable of synthesis of structured lipids (SL) by interesterification. No structured lipids were formed with unimmobilized lipases L, PGE and LN. IM 60 and SP 435 lipases were used for the rest of the study because they gave high conversions of substrates to desired products (C33 and C45). Both lipases were chosen to allow a comparison of the interesterification activity of a 1,3 specific lipase and a nonspecific lipase in the model reaction. Substrate mole ratio. Mole ratio study was performed with SP 435 which contains the lipase from *Candida antarctica*, and IM 60 which contains the lipase from *Rhizemucor miehei*. The mole ratio of trilinolein to tricaproin was varied from 1:1 to 1:4. Trilinolein amount (50 mg) was kept constant while the amount of tricaproin was varied (22–88 mg) to achieve the desired mole ratio. Enzyme amount was kept constant at 7.4 mg rather than at 10% w/w substrates so that any effect on yield will be attributed to mole ratio. FIG. 19 shows that with IM 60 lipase, a mole ratio of 1:2 gave optimum incorporation of caproic acid in the products, yielding 50.7% of dicaproyllinolein (C33) and 23.6% monocaproyldilinolein (C45). The amount of unreacted tricaproin (C21) and trilinolein (C57) in the final product were 2.3% and 23.5%, respectively (Table 12). Less than 1% of MAG and diacylglycerol (DAG) were formed at this level of assay. All yield calculations were based on the amount of structured lipid formed and the unreacted trilinolein and tricaproin.

From the amounts of unreacted trilinolein and tricaproin in the final product, it can be deduced that hydrolysis of tricaproin was more predominant than that of trilinolein at a 1:2 mole ratio (trilinolein:tricparoin). With SP 435 as biocatalyst, a similar triacylglycerol profile was observed at a substrate mole ratio of 1:2, producing optimum incorporation of caproic acid into the SL. In this case, the product yields with SP 435 were lower than with IM 60, with yields of 41 and 18% for C33 and C45, respectively. The mol % of unreacted trilinolein and tricaproin were 8% and 33% respectively, with SP 435 as the biocatalyst. Previous reports showed an inhibitory effect of short chain fatty acids on the reactivity of some lipases (Kuo and Perkin, *J. Am Oil Chem Soc.*, 70:393–399 [1993]). This example showed no significant inhibition of both IM 60 and SP 435 lipases by tricaproin, although a small decrease in C33 yield was observed in the SP 435 system.

Temperature effect. This reaction parameter was studied to determine the optimum reaction temperature for IM 60 and SP 435 lipases. The temperature range was varied from 25 to 65° C. (FIG. 20), and the substrate mole ratio was kept at 1:2 trilinolein:tricaproin. With IM 60 lipase, the product yield varied slightly over the temperature range studied and showed an optimum yield (53.5%) of C33 and (22.2%) of C45 at 45° C. The variation with SP 435 was not as subtle; at 25° C. only 5% of C33 and 3% of C45 were formed. The products yield increased with an increase in temperature with a maximum yield at 55 ° C. of 41% C33 and 18% C45. These results show that lipase SP 435 is more active at higher temperatures than at lower temperatures. IM 60 is active at both low and high temperatures.

Added water. It is generally accepted that water is essential for enzymatic catalysis. This could be attributed to the role water plays in all non-covalent reactions. Water is responsible for maintaining the active conformation of proteins, for facilitating reagent diff-usion and also for maintaining enzyme dynamics. Generally, a low water content favors synthesis over hydrolysis. Table 12 shows the results obtained with IM 60 lipase only. Without water a higher percentage of C33 was formed (50.7%), but this amount dropped to 44.3% with the addition of 10% water. A corresponding increase in C45 from 23.6 to 44.7% was also observed. Adding water at 15 wt% enzyme to SP 435 lipase resulted in a reduction of SL formation from 18% C45 and 41% C33 to 1.5% C45 and 6.2% C33. At water content of 30 wt % enzyme, there were no formation of C33 and C45 by SP 435 lipase.

Effect of solvent polarity. Interaction between organic solvents and enzyme bound water controls the activity of enzymes. The partition coefficient of a solvent between octanol/water is a quantitative measure of solvent polarity. In general, catalytic activity is low in solvents with log P<2 and high in apolar solvents with log P>2 (Laane, et al., *Biotechnol. Bio-eng.*, 30:81–87 [1987]). Nonpolar solvents such as hexane are incapable of containing large amounts of water, and are therefore unable to strip away substantial amounts of water from enzymes, Gorman and Durdick, *Biotechnol. Bioeng.*, 39:392–397 (1992). In the current study, both IM 60 and SP 435 lipase showed apparent increase in SL synthesis (C33) with increase in log P value (Table 13). Interestingly, SP 435 lipase produced SL in acetonitrile (log P=−0.33) and none in benzene (log P=2.0). This result appears to confirm that desorption of water from enzymes is both solvent and enzyme dependent. Hexane and isooctane supported the synthesis of SL in very good yields. In the absence of organic solvents, good yields of C33 (52.3%) and C45 (15.6%) were obtained with IM 60 lipase as the biocatalyst.

Time course. Time course of IM 60 lipase catalyzed interesterification of trilinolein and tricaproin was performed using 1:2 substrate mole ratio. Reaction products were analyzed at 3, 6, 9, 12, 18, 24, 30, 36, 42, and 48 hours. FIG. 21 shows that the highest incorporation of caproic acid (C33) was achieved in 24 hours after which there were no significant increase in yield. The yield of C45 increased initially between 6 to 9 hours incubation and thereafter decreased as more C33 is being formed. 24 hours was used for all other studies because the reaction reached equilibrium at this time.

Effect offreefatty acid as acyl donor. A mole ratio study was carried out using caproic acid as the acyl donor instead of tricaprin. The mole ratio of trilinolein to caproic acid was varied from 1:1 to 1:6 (trilinolein: caproic acid), and 5.7 mg of enzyme (10% w/w of total substrate at 1:1 mole ratio) was added in all mole ratio incubations. At a mole ratio of 1:4, maximum incorporation of caproic acid was observed with both enzymes (FIG. 22). IM 60 lipase produced more C33 than SP 435 lipase indicating preference for free acids. At a substrate mole ratio of 1:4, SP 435 lipase produced 32.5% of C45 and 14.5% of C33 while IM 60 lipase produced 33.3% C45 and 62.9% C33. When caproic acid is compared with tricaproin as the donor, a higher yield of C33 was obtained using caproic acid (82.8% increase) and IM 60 as the biocatalyst. With SP 435 lipase a lower yield of C33 was obtained with free acid as the acyl donor. In this reaction SP 435 lipase was more sensitive to the presence of free acid. After a mole ratio of 1:4, caproic acid inhibited SP 435 activity as reflected by a big decrease in mol % SL. No significant decrease in SL product yield was observed when IM 60 lipase was used.

Pancreatic lipase study. A pancreatic lipase study was done to determine the fatty acid composition of the sn-2 position of the structured lipid (and thus whether the SL have improved absorption of fatty acids at the sn-2 positions of triacylglycerols). SL were separated based on degree of unsaturation using argentation silver nitrate TLC and pancreatic lipase analysis performed on the C33 and C45 SL species. The result is given in Table 14. When IM 60 lipase was used, 47.9% of C33 consisted of LCC and CCL and 52.1% consisted of CLC where L=linoleic acid, and C=caproic acid. We found more caproic acid (57.6%), at the sn-2 position of C33 synthesized with SP 435 lipase than with IM 60 lipase (47.9%). For C45 species, SP 435 gave more C18:2 (73.9%) at the sn-2 position than IM 60 lipase (44.9%). IM 60 lipase catalyzes the exchange of esters from the sn-1, and 3 positions of the TAG leaving the sn-2 position intact. With SP 435 lipase, the ester exchange takes place at all three positions of the TAG.

TABLE 12

Effect of Added Water on the Lipase-Catalyzed Interesterification of Trilinolein and Tricaproin with IM 60 as Biocatalyst

| Added Water | Mol % | | | |
|---|---|---|---|---|
| (% w/w/enzyme) | C57 | C45 | C33 | C21 |
| 0 | 6.3 ± 0.5 | 44.7 ± 1.1 | 44.3 ± 0.01 | 3.7 ± 2.7 |
| 15 | 7.5 ± 1.5 | 44.7 ± 2.1 | 43.9 ± 0.5 | 3.9 ± 0.1 |
| 30 | 7.1 ± 1.4 | 44.7 ± 2.2 | 45.9 ± 0.5 | 4.3 ± 0.3 |
| 60 | 6.3 ± 0.9 | 44.0 ± 4.2 | 45.7 ± 5.2 | 4.0 ± 0 |
| 90 | 9.7 ± 2.8 | 41.4 ± 2.9 | 43.9 ± 1.3 | 5.0 ± 1.4 |

Amount of water varied from 0–90% w/w of enzyme. The reaction mixture was incubated at 45° C. for 24 hours. The mole ratio of trilinolein to tricaproin was 1:2. C57 = unreacted trilinolein, C33 = dicaproyllinolein, and C45 = monocaproyldilinolein, C21 = tricaproin. Number after C indicates total carbon number of the triacylglycerols.

TABLE 13

Effect of Selected Organic Solvents on SP 435 and IM 60 Catalyzed Synthesis of Structured Lipids

| Solvent[a] | Water content (wt %) | Log P value[b] | Mol % C33 IM 60 | Mol % C33 SP 435 | Mol % C45 IM 60 | Mol % C45 SP 435 |
|---|---|---|---|---|---|---|
| No solvent | | | 52.3 ± 0.2 | 32.5 ± 0.7 | 15.6 ± 0.1 | 6.2 ± 0.1 |
| iso-Octane | 0.004 | 4.51 | 57.6 ± 0.1 | 44.3 ± 5.0 | 16.9 ± 0.9 | 8.6 ± 0.2 |
| n-Hexane | 0.004 | 3.50 | 54.8 ± 2.5 | 39.3 ± 0.5 | 21.4 ± 1.6 | 14.5 ± 5.0 |
| Benzene | 0.016 | 2.00 | 34.8 ± 3.0 | N/A[c] | 4.7 ± 6.0 | N/A |
| Tetrahydrofuran | 0.140 | 0.49 | N/A | N/A | N/A | N/A |
| Acetonitrile | 0.053 | −0.33 | N/A | 20.2 ± 1.1 | N/A | 10.3 ± 1.2 |

[a]Solvents were dried over molecular sieve 4A.
[b]Source: Laane, et al., Supra, and iso-octane Manjon, et al., Supra.
[c]N/A indicates no SL formation.
The water content of the solvents were measured using a 684 KF coulometer equipped with a 649 stirrer (Brinkman Instrument, Inc., Westbury, NY). Where IM = IM 60, SP = SP 435, C33 = dicaproyllinolein, and C45 = monocaproyldilinolein. Number after C indicates total carbon number of the triacylglycerols.

TABLE 14 sn-2 Fatty Acid Analysis After Pancreatic Lipase Hydrolysis

| sn-2 fatty acid (%) | C33 (IM 60) | C33 (SP 435) | C45 (IM 60) | C45 (SP 435) |
|---|---|---|---|---|
| C6 | 47.9 ± 10 | 57.6 ± 8 | 55.1 ± 11 | 26.1 ± 12 |
| C18:2 | 52.1 ± 10 | 42.4 ± 8 | 44.9 ± 12 | 73.9 ± 12 |

Pancreatic lipase hydrolysis was done using the method of Luddy, et al. Supra. C33 = dicaproyllinolein, and C45 = monocaproyldilinolein. Number after C indicates total carbon number of the triacylglycerols.

EXAMPLE 6

CHARACTERIZATION OF ENZYMATICALLY SYNTHESIZED STRUCTURE LIPIDS CONTAINING EICOSAPENTAENOIC, DOCOSAHEXAENOIC AND CAPRYLIC ACIDS

In this example, SL containing n-3 and medium-chain fatty acids (caprylic acid) were synthesized with immobilized lipase (SP 435) in gram quantities.

MATERIALS AND METHODS

Materials. Tricaprylin (1,2,3-trioctanoyl glycerol, 97–98%), porcine pancreatic lipase (type II, crude), TEP (1,1,3,3,-tetrarnethoxy propane), BHT (butylated hydroxytoluene), and a-tocopherol were obtained from Sigma Chemical Company (St. Louis, Mo.). n-3 fatty acids (EPAX 6000) and fish oil TAG (EPAX 5500) were provided by Pronova Biocare (Sandeijord, Norway). Hanus solution (Labchem, Inc., Pittsburgh, Pa.), 4,6-dihydroxy pyrimidine-2-thiol (Aldrich Chemical Company, Milwaukee, Wis.) were purchased. TCA (trichloroacetic acid), chloroform, and potassium iodide were purchased from J. T. Baker, Inc. (Phillipsburg, N.J.). Isooctane, ethanol, and hexane were obtained from Fisher Scientific (Fair Lawn, N.J.). Sodium thiosulfate was obtained from EM Science (Gibbstown, N.J.). Immobilized enzye, SP 435, was provided by Novo Nordisk Biochem North America Inc. (Franklinton, N.C.).

Synthesis of SL. Structured lipids containing eicosapentaenoic, docosahexaenoic, and medium-chain fatty acids (caprylic acid) were synthesized in gram quantities by mixing 5 grams tricaprylin with eicosapentaenoic acid-rich fish oil fatty acids, EPAX 6000 (6.5 g) in a 1:2 molar ratio in 90 mL hexane and transesterified by incubation at 55° C. in a shaking water bath (200 rpm) for 24 hours with SP 435 lipase (10% by weight of total substrates) as the biocatalyst using 125 mL Elrenmeyer flasks as the bioreactor. After 48 batches of reaction, the products were pooled and the hexane was evaporated in Buchi rotary evaporator (Postfach, Switzerland). Short-path distillation was then used for the purification of synthesized SL. Distillation conditions were 1.1 Torr and 170° C. at a feed flow rate of 3 mL/min. After distillation, approximately 240 grams of purified SL was obtained.

Deacidification by ethanol extraction. 80, 75, and 70% ethanol-water (v/v) solvents were prepared and saturated with hexane. Distilled SL was mixed with hexane (1:2, w/w) to form miscella. This SL miscella in hexane was mixed with prepared 80, 75, and 70% ethanol at a ratio of 2:1 miscella/solvent, v/v). A separatory funnel was used for phase separation. The separatory funnel was shaken for 5 min. and left for 20 min. The upper hexane miscella phase was separated and evaporated under nitrogen.

Deacidification by alkaline extraction. Deacidification by alkaline extraction was modified from the method described by Shimada, et al., *J. Am. Oil. Chem. Soc.*, 72:1577–1581 (1995). 5 grams of SL purified by short-path distillation was mixed with hexane (150 mL), phenolphthalein solution and 80 mL of 0.5 N KOH solution in 20% ethanol. The separatory funnel was shaken and the upper phase (hexane phase) collected. Then, 30 mL of 0.5 N KOH in 20% ethanol and 60 mL of saturated NaCI solution were mixed and hexane phase collected. The hexane phase containing SL was passed through an anhydrous sodium sulfate column and hexane evaporated to obtain the deacidified SL (3.6 grams). The deacidification steps were repeated to obtain enough amount of purified SL for further studies. The deacidification procedure is illustrated in FIG. 23.

Chemical properties of SL. Percentages of free fatty acids (AOCS, Ca 5a-40), peroxide value (AOAC, 965.33), iodine value (AOAC, 920.158), and saponification number (AOAC, 920.160) were determined by methods previously described in, i.e., *Official Methods and Recommended Practices of the American Oil Chemists' Society*, ed. D. Firestone, American Oil Chemists' Society, Campaign, Ill., (1992) and *Official Methods of Analysis 15th Edition Association of Official Analysis Chemists*, ed. K. Helrich, Association of Official Analysis Chemists, Inc., Arlington, Va. (1990).

TBA. A modified extraction 2-thiobarbituric acid method was used, Salih, et al., *Poult. Sci.*, 66:1483–1488 (1987). The TBA test expresses lipid oxidation in milligram malonaldehyde (secondary oxidation product of polyunsaturated fatty acids) per kilogram of sample. 1±0.002 grams of SL was mixed with 0.01, 0.02, and 0.04 grams of α-tocopherol in a 25 mL flask and left at room temperature without protection from light for 12, 24, and 48 hours. Each sample was then purged with nitrogen and stored at −90° C. until assay. One milliliter of 6% BHT in ethanol and 25 mL 5% TCA solution in distilled water were added to each sample and blended. A 2 mL aliquot of the blended sample was mixed with 0.02 M TBA solution (3 mL) in screw capped test tubes. After vortexing (30 sec.), the tubes were incubated in boiling water for 30 min., cooled and the absorbance against blank was measured at 535 nm. A 5 μL aliquot of TEP (0.92 g/mL) was diluted to 5 mL with 5% TCA solution and diluted to prepare various concentrations ranging from $9.2 \times 1_{0-1}$ g/mL to $3.68 \times 101$ g/mL. Each dilution was incubated and the absorbance against blank was measured after cooling. Standard curve was plotted using absorbance values vs amount of TEP which was converted from concentration.

Conjugated diene value (CD). Two grams of SL were placed into a 25 mL flask and exposed to standard room light at room temperature for 12, 24, and 48 hours. During lipid oxidation, conjugated diene formation can be measured at 233 nm (AOCS, Ti la-64) as described in Shimada, et al., *J. Am. Oil. Chem. Soc.*, 73:1577–1581 (1995). To measure the CD, 13 μL of sample (approximately 0.01 grams) was mixed thoroughly with 10 mL of isooctane and diluted ten times with isooctane. Absorbance was then measured against blank with a Beckman DU-64 spectrophotometer (Beckman Instruments, Fullerton, Calif.). The observed absorbance was between 0.2 and 0.8.

Oxidative stability index (OSI). An Oxidative Stability Instrument (Omnion, Rockland, Mass.) was used to measure induction times. Five grams of tricaprylin, EPAX 5500 (fish oil TAG, Pronova Biocare, Sandefjord, Norway), and SL which was deacidified by alkali-liquid extraction were placed into the disposable borosilicate glass reaction tubes with disposable pipets. The heating temperature was 80° C. The polycarbonate conductivity tubes were filled with deionized water and he probes were connected. After temperature reached 80° C., air was bubbled in. The air flow was set to 2.5 mL/sec. OSI time was determined with an on-line computer, which monitored the conductivity vs time and plotted the induction period automatically. OSI values at 80° C. were converted to AOM and OSI values at 97.8° C.

sn-2 Fatty acids in SL by pancreatic hydrolysis. 1 mL of 1 M Tris-HCl buffer (pH 7.6), 0.25 mL of bile salt solution (0.05%), 0.1 mL of 2.2% $CaCl_2$ solution and 10 mg of pancreatic lipase were mixed and incubated at 37° C. for 2 min. Extraction of the sn-2 monoacylglycerol and methylation for fatty acid analysis is described in Lee and Akoh, *J. Am Oil. Chem. Soc.*, 73:611–615 (1996).

GC analysis. For fatty acid composition, a Hewlett-Packard 5890 Series II gas chromatograph (GC) equipped with flame-ionization detector (Hewlett-Packard, Avondale, Pa.) was used. The column and analysis condition were as described in Lee and Akoh, supra.

Statistics. The Statistical Analysis System (SAS, Cary, N.C.) was used to perform statistical computations. Data were expressed as means±standard deviation. Duncan's multiple range test was performed to test for significance of difference. Significance was determined at $p<0.05$.

RESULTS AND DISCUSSION

Synthesis andfatty acid analysis of SL. N−3 free acids (EPAX 6000) which were used as substrate for providing n-3 acyl moieties contained 33.8% EPA and 26% DHA and 73% of total n-3 polyunsaturated fatty acids (specified by manufacturer). SL purified by short-path distillation (approximately 240 grams, total yield=43.5% based on the total weight of substrates) contained 46.9 mol % caprylic acid, 23.2 mol % EPA and 21.7 mol % DHA as major fatty acids. The fatty acid composition of SL are described in Table 15.

Deacidification. Table 16 shows the % free fatty acid values after deacidification by alkaline extraction or 80, 75, and 70% ethanol-water solvents. Refining with alkaline extraction was the most effective in reducing the % FFA among these methods. The % FFA was reduced to 1. In this way 14.6 grams of refined SL (73% yield) was obtained from 20 grams of unrefined sample after alkaline reaction, leading to 27% weight loss. Deacidification of miscella by ethanol-water solvents was effective in removing FFA in this study. Only a 2% drop in FFA value was obtained with 80% ethanol-water solvent compared to SL before refining. Higher ethanol contents (85, 90 and 95%) tended to form one phase, in which extraction of miscella was impossible. Deacidification of oil by alkaline extraction as used in this study can serve as an alternative process to reduce FPA from high acidity oils when the procedure is conducted at normal atmospheric pressure and temperature.

Chemical properness of SL. Table 17 shows selected chemical properties of SL compared to other oils. Iodine value (IV) is a measurement of the unsaturation of a lipid which is also a measure of the sample's content of double bonds. The result is defined as the number of grams of iodine absorbed by 100 grams of sample. The IV of this SL was 129.2. Generally, menhaden oil and cod-liver oil were reported to contain>22% EPA and DHA. When compared with menhaden oil (IV, 150–165) and cod-liver oil (IV, 159–166), SL has less IV due to saturation by caprylic acids in SL. The IV of a rich source of MCFA (medium-chain fatty acid), palm kernel oil, is 16–20. Saponification number (SN) is defined as the number of milligrams of potassium hydroxide to saponify 1 gram of sample. SN is an estimate of the mean molecular weight of the constituent acids in oils. This SL has a SN of 292.9. SNs of coconut oil, menhaden oil and cod liver were 248–265, 189–193, and 180–190, respectively.

Peroxide value (PV), conjugated diene (CD), TBA and OSI. Peroxide value determination is one method for measuring oxidative deterioration and is defined in units of milk equivalents of peroxide per kg of sample. Generally, a fresh fish oil sample has PV in the range of 0 to 2. This SL had a PV of 2.1 and we can assume that oxidation of SL has not occurred to any appreciable extent.

Spectrophotometric determination of conjugated dienoic acid determines the diene conjugation of unsaturated linkages present, which is expressed as a percentage of conjugated dienoic acid (CD). Formation of CD increased with time of exposure as expected. It seems that acceleration of oxidation occurred after 24 hours because the change in absorbance was increased during a 24 to 48 hour period. The % conjugated diene after 0, 12, 24, and 48 hours were 1.7%, 1.7%, 1.8% and 2.2%, respectively. Thus, this SL was more susceptible to oxidation after 24 hours in the absence of an antioxidant.

FIG. 24 shows the antioxidant effect of α-tocopherol on SL. TBA value increased with time as expected: TBA value of fresh SL was 0.07 and this value increased to 0.77, 1.01 and 1.4 after 12, 24, and 48 hours, respectively, without antioxidant present. However, 4% α-tocopherol, the highest concentration examined, was the most effective in reducing oxidation. After 48 hours, the presence of 1, 2, and 4% α-tocopherol reduced the oxidation of SL significantly (FIG. 24).

An OSI value for tricaprylin could not be obtained in this study because of complete saturation of its fatty acids, indicating that tricaprylin was quite stable to oxidation (FIG. 25). OSI value of SL purified by alkaline extraction was 2.55 at 80° C. which was longer than the OSI value or EPAX 5500 (fish oil). However, approximately 1% free fatty acid still remained in this SL and should be considered because free fatty acid can easily be converted to volatile organic acids, leading to an increase in conductivity. Because the free fatty acid form instead of triacylglycerol form of n-3 polyunsaturated fatty acids cause more rapid oxidation and it is difficult to obtain their DSI value, we used fish oil (EPAX 5500, triacylglycerol form of n-3-rich fatty acids) for OSI comparison with SL. From the OSI results, we can assume that caprylic acid, the saturated fatty acid moiety in triacylglycerol molecule of SL tended to protect SL against oxidation and increased the induction periods. The high content of unsaturation in EPAX 5500 contributed to the lower DSI values. The usual operating temperature of OSI is 110° C. but OSI can be run at lower temperature (80° C.) for highly unstable oils, such as fish oil. The automatic conversion of OSI value at 80° C. to AOM and OSI at 97.8° C. were obtained for comparative purpose (FIG. 25).

sn-2 Analysis of SL. Caprylic acid (64.3 mol %), EPA (17.8 mol %) and DHA (15 mol %) were the major fatty acids incorporated at the sn-2 position (Table 15). Because we used non-specific lipase (SP 435), some of the caprylic acid at the sn-2 position as well as sn-1, 3 positions on tricaprylin were replaced by EPA and DHA, the major fatty acids in EPAX 6000. The total n-3 incorporation at the sn-2 position is 32.8% in this example.

TABLE 15

Fatty Acid Composition (Mol %) of Structured Lipids and their sn-2 Position

| Fatty acid | SL[a] | sn-2 position |
|---|---|---|
| 8:0 | 46.9 | 64.3 |
| 16:0 | 0.6 | nd[b] |
| 16:1 n-7 | 1.3 | 3 |
| 18:0 | 2.1 | nd |
| 18:1 n-9 | 0.5 | nd |
| 18:2 n-6 | 0.5 | nd |
| 18:3 n-3 | 0.6 | nd |
| 20:0 | 2.6 | nd |
| 20:5 n-3 | 23.2 | 17.8 |
| 22:6 n-3 | 21.7 | 15.0 |

[a]Structured lipids containing caprylic and n-3 (eicosapentaenoic and docosahexaenoic) acids.
[b]Non-detectable.

TABLE 16

% FFA (Free Fatty Acid) Values Before and After Deacidification with Alkaline Extraction or Various Concentrations of Ethanol-Water Solvents

| Refining Methods | % FFA |
|---|---|
| Before Refining | 10.2 |
| 70% ethanol-water | 9.3 |
| 75% ethanol-water | 8.6 |
| 80% ethanol-water | 8.1 |
| Alkaline Extraction | 1.0 |

TABLE 17

Saponification Number and Iodine Values of Structured Lipids Compared to Selected Oils

| Oil | Saponification Number | Iodine Value |
|---|---|---|
| SL | 292.9 | 129.2 |
| Soybean Oil | 188–195 | 120–141 |
| Coconut Oil | 248–265 | 7.5–10 |
| Palm kernel Oil | 230–254 | 16–20 |
| Cod-liver Oil | 185–187 | 159–166 |
| Menhaden Oil | 192–199 | 150–165 |

The saponification numbers and iodine values for other oils are from Stansby, Fish Oils, AVI Publishing Co., Inc., West Port, CT, p. 433 (1967) and Hamilton and Russell, Analysis of Oils and Fats, Elsevier Science Pub. Co., New York, NY, pp. 1–90 (1986).

EXAMPLE 7

ENZYMATICALLY PRODUCED STRUCTURED LIPIDS CONTAINING OMEGA-3 AND MEDIUM CHAIN FATTY ACIDS MODULATE SERUM LIPIDS IN MICE

In this example, diets supplemented with SL containing n-3 PUFA (eicosapentaenoic and docosaxhexaenoic) and caprylic acid or soybean oil (16.7 g/100 g) were fed to four to six week old female mice for 21 days. The effect of the diets on serum lipids (HDL-cholesterol, LDL-cholesterol, total cholesterol, triacylglycerol), weight, and glucose concentrations were determined. Each was significantly lower in the SL-fed group. The proportion of total T-cells (Thy 1.2+), T helper cells (CD4+), T cytotoxic-suppressor and the ratio of $CD4^+$ to $CD8^+$ in spleen were analyzed. The SL-fed group had a higher $CD4_+/CD8^+$ ratio.

MATERIALS AND METHODS

Animals. Animal care and use were carried out in accordance with the Institutional Animal Care and Use Committee guidelines of the University of Georgia. Twenty four, four to six week old female ICR (Hsd:ICR) mice (Harlan Sprague Dawley, Indianapolis, Ind.), weighing 21 to 24 grams were used. The animal room was kept at 23±0.5° C. Room lighting consisted of a reversed light (12 hours) and dark (12 hours) cycle. After seven days acclimatization period, mice were divided into two groups and weighed. Each diet group comprised 12 mice. Mice were fed the experimental diet for 21 days and weighed every day. Experimental diet was obtained from L/M Animal Farms (Pleasant Plate, Ohio). The proximate composition of diet was (%) protein: 18, fat: 3, fiber: 16, calcium: 1.4, phosphorous: 0–8, salt: 0.4, nitrogen free extract: 55 and vitamin/mineral mixtures: 2.5. The 3% fat in the diet would provide the essential fatty acid requirements for the mice. From a preliminary test, 5 grams of diet was enough for one mouse during 24 hours. Every morning (1000 hours), 5 grams of fresh diets were mixed with 1 gram of soybean oil or SL. SL was produced from n-3 rich (eicosapentaenoic and docosahexaenoic) polyunsaturated fatty acids and tricaprylin with a non-specific immobilized lipase (SP 435, Novo Nordisk Biochem North America Inc., Franklinton, N.C.) in our laboratory. The reaction mixture was incubated at 55° C. in water bath (200 rpm) using 125 mL Erlenmeyer flasks as the bioreactor. After the reaction, SL was purified by short-path distillation at 1.1. Torr, 170° C. and a feed rate of 3 mL/minute. SL used for diet formulation contained (mol %): 46.9, 8:0; 0.6, 16:0; 1.3, 16:1 n-7; 2.1, 18:0; 0.5, 18:1 n-9; 0.5, 18:2 n-6; 0.6, 18:3 n-3; 2.6, 20:0; 23.2, 20:5 n-3; and 21.7, 22:6 n-3. Soybean oil used for diet formulation contained (mol %): 12.9, 16:0; 4.6, 18:0; 19.6, 18:1 n-9; 54.4, 18:2 n-6; and 8.5, 18:3 n-3. Both oils were analyzed by gas chromatography. Water was given ad libitum during the experimental period. The sn-2 fatty acid composition of the supplemented lipids, soybean oil and SL are described in Table 18. To prevent oxidation, soybean oil and SL were portioned into small containers and stored under nitrogen atmosphere in the freezer (−90° C.) until the preparation of diets.

Analysis of Liver and Blood. After 21 days of consuming the experimental diets, mice were killed by $CO_2$ inhalation. Mice were fasted before being killed. Blood was collected in heparin containing tubes from the heart. Blood samples from each diet group were delivered to Athens Regional Medical Center soon after collecting for analysis. Serum lipids were analyzed using Boehringer Mannheim Hitachi 911 system (San Jose, Calif.). Livers were removed from each mouse and stored at −90° C. until analyzed. Each spleen was removed, placed in an Eppendorf tube containing nutrient mixture F-12 Ham (Sigma Chemical Company, St. Louis, Mo.) and stored at 4° C. until analyzed. All spleens were analyzed within 12 hours.

Monoclonal Antibodies (MoAb). FITC-conjugated MoAb-Mouse CD4 (product #F7400), R-phycoerythrin-conjugated MoAbmouse CD8 (#P3067) were used for staining T helper cells and T cytotoxic-suppressor cells. PITC-conjugated MoAb-Mouse Thy 1.2 (#F7650) was used as a pan T-cell marker. FITC-conjugated, isotype-matched, non-specific rat or mouse immunoglobulin (mouse IgG 2bk, #F6647) was used as negative staning control. All MoAb used in this study were purchased from Sigma Chemical Company (St. Louis, Mo.).

Staining of Splenocytes and Flow Ctometry. Preparation and staining of splenocytes were conducted using manufacturer's protocol. Each spleen was teased through fine stainless-steel screen into 10 mL prechilled 0.01 M phosphate buffered saline (PBS, pH 7.4) containing 1% BSA and 0.1% $NaN_3$. Cells were pelleted by centrifugation (3000 g×6 minutes). Erythrocytes were lysed by resuspending cell pellets in 10 mL red blood cell (RBC) lysing solution (Sigma Chemical Company, St. Louis, Mo.) for 10 minutes on ice. Cells were pelleted, resuspended, and washed two times to 5 mL PBS-BSA-$NAN_3$ buffer. Cells were counted and adjusted to $1\times10^7$ cells/mL. Cells were>90% viable as determined by dye exclusion. Each $1\times10^6$ was allocated for staining into 15 mL centrifuge tubes (Fisher Scientific, Pittsburgh, Pa.). Cell surface Fc receptors were blocked by incubating the cells with 15% normal goat serum for 10 minutes at 4° C. After adding 4 $\mu$L MoAb-Mouse Thy 1.2 for staining pan T-cells and MoAb-Mouse CD4 and CD8 for staining each Tcell subpopulation, mixtures were vortexed gently and incubated for 30 minutes at 4° C. After incubation, 2 mL of prechilled PBS-BSA-$NaN_3$ buffer was added and mixed, centrifuged (1800 rpm×10 minutes) and washed twice. Cells were fixed in 0.5 mL of 1% paraformaldehyde.

Flow Cytometry. Cell-mediated immune responses were measured by total T-cell proportion and the ratio of T-cell subsets. The proportion of T-cells in leukocytes and the ratio of T-cell subsets were determined by flow cytometry after staining and incubating with monoclonal antibodies. Cell analysis was performed on a Coulter Elite Analyzer (Hlaleah, Fla.), operating the air-cooled argon laser at 15 mW (488 nm). Four detectors simultaneously measure forward, side scatter and green/red fluorescence for each cell. Fluorescence signals were amplified logarithmically. Dead lymphocytes, granulocytes and monocytes were gaged out according to preliminary settings due to their cell granulocytes and cell monocytes were gaged out according to preliminary settings due to their cell granularity and cell size. Histogram and data were analyzed with an on-line computer.

Fatty Acid Composition of Liver, Soybean Oil and SL. Liver from each mouse was weighed and approximately 1 gram of liver tissue was homogenized with 12 mL prechilled $CHCl_3$/MeOH (2:1, v/v) containing 0.005% BHT (Folch reagent). After homogenization with Polytron (Brinknann Instruments, Inc., Westbury, N.Y.) for 2–3 minutes, extracts were filtered and 4 mL of 0.88% KCl was added. Lower phase was collected and solvents were evaporated. Lipids were methylated with 3 mL 6% HCl in methanol at 75° C. for two hours, extracted with hexane (2 mL) and 0.1 M KCl solution (1 mL), centrifuged, and concentrated under nitrogen. Approximately 10 mg of soybean oil or SL were also methylated and concentrated as described above for fatty acid composition analysis.

sn-2 Fatty Acids in Soybean Oil and SL by Pancreatic Hydrolysis. 100 mg of lipid, 1 mL 1 M Tris-HCl buffer (pH 7.6), 0.25 mL bile salt solution, 0.1 mL 2.2% $CaCl_2$ solution and 10 mg pancreatic lipase were mixed and incubated at 37° C. for two minutes. Extraction of sn-2 monoacylglycerol and methylation for GC analysis was described in Lee and Akoh, *J. Am. Oil. Chem. Soc.*, 73:611–15 (1996).

GC Analysis. For fatty acid composition, a Hewlett-Packard 5890 Series II gas chromatograph (GC) equipped with flame-ionization detector (Hewlett-Packard, Avondale, Pa.) was used. The column and analysis condition were described previously in Lee and Akoh, supra.

Statistics. The Statistical Analysis System (SAS, Cary, N.C.) was used to perform statistical computations. Data are expressed as means±standard deviation. Student's t-test was performed. Values at p<0.05 were considered significant.

The fatty acid (FA) composition of SL and soybean oil after pancreatic hydrolysis are shown in Table 18. The major FA at the sn-2 position of SL were 8:0, 20:5 n-3, and 22:6 n-3. In soybean oil, 18:1 n-9 and 18:2 n-6 were the major FA at that position. Serum glucose concentration was not statistically significant between groups (Table 19). In the SL-fed mice, a 49% decrease in total cholesterol concentration and 35.4% decrease in low density lipoprotein (LDL) cholesterol were observed compared to soybean oil-fed group. Total triacylglycerol (TAG) concentration in serum was significantly higher in soybean oil-fed than in SL-fed mice (p<0.05). Along with higher total serum cholesterol and LDL concentrations in the mice-fed soybean oil, HDL-cholesterol concentration was also significantly greater p<0.05). The proportion of total T cells, T helper cells (CD4+), and T cytotoxic-suppressor cells (CD8+) in spleen were not significantly different between two dietary groups. However, a 16% higher CD4+/CD8+ ratio of SL-fed group was observed (Table 19).

The body weight after 21 days in soybean oil-fed mice was significantly greater than that in SL-fed mice atp<0.05 (5.8% increase in SL-fed and 11.4% increase in soybean oil-fed, respectively), even though the mean initial body weights of two groups did not differ. At the end of the experiment, however, liver weights of SL-fed group were significantly greater than that of soybean oil-fed group (p<0.05) (Table 19).

TABLE 18 sn-2 Fatty Acid Composition of Structured Lipids (SL) and Soybean Oil

| Fatty acid | SL | Soybean oil Mol % |
|---|---|---|
| 8:0 | 64.3 ± 0.2 | nd |
| 16:0 | nd* | 3.1 ± 0.2 |
| 16:1 n-7 | 3.0 ± 0.5 | nd |
| 18:0 | nd | 1.3 ± 0.0 |
| 18:1 n-9 | nd | 24.8 ± 0.7 |
| 18:2 n-6 | nd | 65.8 ± 0.6 |
| 18:3 n-3 | nd | 5.1 ± 0.3 |
| 20:5 n-3 | 17.8 ± 0.7 | nd |
| 22:6 n-3 | 15.0 ± 0.5 | nd |

*nd, non-detectable.
Data are expressed as mean ± SD, n-3.

The fatty acid (FA) composition of liver TAG showed that there were significant differences in the amount of 16:1 n-7, 18:1 n-9, 18:2 n-6, 20:3 n-6, 20:4 n-6, 20:5 n-3, 22:5 n-6, 22:5 n-3 and 22:6 n-3 (Table 20). The major FA in soybean oil was 18:2 n-6, (54.4 mol %) whereas those of SL were 8:0 (46.9 mol %), 20:5 n-3, (23.2 mol %), and 22:6 n-3 (21.7 mol %). The amount of 16:0 was 12.9 mol % in soybean oil and 0.6 mol % in SL. After 21 days' experiment, however, the mol % of 16:0 in liver was not significantly different between the two groups. The mol % of EPA and DHA in the liver were much higher in SL-fed mice than those of soybean oil-fed. It is interesting that in spite of higher content of 8:0 (46.9 mol %) in SL, we could not detect 8:0 in the liver of SL-fed group, indicating rapid metabolism of 8:0 for quick energy. The overall ratio of n-3/n-6 FA in the liver were 2.8 in SL-fed and 0.4 in soybean oil-fed, respectively.

TABLE 19

Concentration of Serum Lipids, Glucose, T Cells, CD4+, CD8+ Cells, Body Weight Gain and Liver Weight in Response to Soybean Oil vs. Structured Lipids (SL) Containing N-3 and Medium-Chain Fatty Acids

| Parameter | SL | Soybean oil |
|---|---|---|
| Glucose (mg/L) | 2000.8 ± 80.0 | 2170.3 ± 320.0 |
| Total cholesterol (mg/L) | 720.2 ± 100.4 | 1410.8 ± 180.7* |
| LDL cholesterol (mg/L) | 170.0 ± 40.6 | 260.3 ± 30.7* |
| HDL cholesterol (mg/L) | 420.4 ± 60.0 | 940.4 ± 180.8* |
| Total triacylglycerol (mg/L) | 630.8 ± 210.1 | 1360.2 ± 590.7* |
| Total T cell (%) | 41.9 ± 8.2 | 43.6 ± 9.1 |
| CD4+ (%) | 28.8 ± 5.1 | 28.6 ± 4.9 |
| CD8+ (%) | 8.0 ± 1.6 | 9.3 ± 2.0 |
| Day-1 Body weight (g) | 22.6 ± 1.2 | 22.9 ± 1.2 |
| Day-21 Body weight (g) | 24.0 ± 1.7 | 26.0 ± 1.5* |
| Liver weight (g) | 1.4 ± 0.1 | 1.2 ± 0.2* |

*Means significant difference between SL-fed and soybean oil-fed group (p < 0.05).
Data are expressed as mean ± SD n = 12.

TABLE 20

Dietary Effects of Structured Lipids (SL) vs. Soybean Oil on Liver Fatty Acid Composition

| Fatty acid | SL | Soybean Oil Mol % |
|---|---|---|
| 16:0 | 8.2 ± 0.6 | 8.0 ± 1.0 |
| 16:1 | 0.3 ± 0.9 | 0.1 ± 0.1* |
| 18:0 | 15.1 ± 0.8 | 15.4 ± 1.0 |
| 18:1 n-9 | 6.4 ± 0.9 | 8.5 ± 1.2* |
| 18:2 n-6 | 8.1 ± 0.9 | 22 ± 2.6* |
| 18:3 n-3 | 0.7 ± 0.2 | 0.7 ± 0.3 |
| 20:3 n-6 | 0.9 ± 0.0 | 1.9 ± 0.3* |
| 20:4 n-6 | 8.4 ± 0.6 | 20.2 ± 2.6* |
| 20:5 n-3 | 7.7 ± 0.8 | 0.7 ± 0.4* |
| 22:5 n-6 | 0.8 ± 0.4 | 3.4 ± 2.2* |
| 22:5 n-3 | 2.2 ± 0.1 | 0.5 ± 0.3* |
| 22:6 n-3 | 40.1 ± 3.4 | 18.4 ± 25* |
| Total n-3 | 50.7 ± 2.9 | 19.9 ± 3.3* |
| Total n-6 | 18.2 ± 0.3 | 47.5 ± 4.4* |

*Asterisk means significant difference between SL-fed and soybean oil-fed (p < 0.05).
Data are expressed as mean ± SD, n = 12.

The results showed that total serum cholesterol and TAG decreased −49% and −53.2%, respectively, in SL-fed mice. It is possible that the reduced cholesterol and TAG concentrations in serum by SL diet are due to 8:0, n-3 PUFA, or both. The reduction in serum HDL-cholesterol by SL, while not desirable, is not unusual. Body weight gain in soybean oil-fed was much higher than in SL-fed mice, but the liver weight/body weight was vice versa. Higher liver weight in SL-fed group may be partly attributed to liver fractional protein synthetic rates (FRS), causing improved hepatic protein synthesis by MCT. The proportions of T cells were 41.9% in SL-fed and 43.6% in soybean oil-fed mice, respectively, with no significant difference, suggesting that different types of lipids (SL vs. soybean oil) did not affect the proliferation of T-cells. T cell subsets, T helper cells (CD4+) and T cytotoxic-suppressor cells (CD8+), in spleen were not significantly different between the two dietary groups.

MCFA in the SL were oxidized rapidly and did not accumulate in the liver because we could not detect the presence of caprylic acid in the liver of SL-fed mice (Table 20). Significantly higher amount of EPA (20:5 n-3), docosapentaenoic acid (22:5 n-3) and DHA (22:6 n-3) in the liver from SL-fed were due to higher contents of n-3 PUFA in SL. Different types of FA in the diets may lead to different accumulation and/or incorporation of FA into intrahepatic TAG, and eventually lead to change in fatty acid composition of the liver. From these results, SL containing both MCFA and n-3 PUFA are shown to be a therapeutic or medical lipid source and useful in enteral and parenteral nutrition. These SL are expected to lead to a decrease in the concentrations of serum cholesterols, TAG, and to reduce body weight. The MCPA in SL showed rapid oxidation and a source of quick energy compared to soybean oil.

Table 21 shows the fatty acid profile of a SL mixture also found to improve immune system function, reduce serum cholesterol and reduce weight gain, as discussed above in this Example 7, (far right). The entirety of Table 21 shows a comparison of this SL mixture to other lipid emulsions. Neobee is based on glycerol esters of 8:0, 10:0 and long-chain fatty acids which may vary from 16:0 to 18:3n-3 (Stepan Company, Maywood, N.J., USA). Intralipid is a 20% soybean oil emulsion (Kabi Vitrum, Berkeley, Calif., USA, and Pharmacia AB, Stockholm, Sweden), and Fat Emulsion 73403 is an emulsion of 8:0, 10:0 and long-chain fatty acids (Pharmacia AB, Stockholm, Sweden).

Typical fatty acid profiles of selected structured lipid products and MCT are given in Table 21. The applications for these products will vary depending on the need of the patient or intended food products.

TABLE 21

Fatty acid profiles of typical lipid emulsions (FE 73403 and Intralipid), medium-chain triacylglycerols (MCT) and structured lipids (SL)

| Fatty acid | Fatty acid composition (%) | | | |
|---|---|---|---|---|
| | FE 73403 | Intralipid 20% | MCT | SL[1] |
| 8:0 | 27 | — | 65–75 | 46.9 |
| 10:0 | 10 | — | 25–35 | — |
| 12:0 | — | — | 1–2 | — |
| 16:0 | 7 | 13 | — | 0.6 |
| 18:0 | 3 | 4 | — | 2.1 |
| 18:1 n-9 | 13 | 22 | — | 0.5 |
| 18:2 n-6 | 33 | 52 | — | 0.5 |
| 18:3 n-3 | 5 | 8 | — | 0.6 |
| 20:5 n-3 | — | — | — | 23.3 |
| 22:6 n-3 | — | — | — | 21.7 |
| Others | 2 | 1 | 1–2 | 3.8 |

[1]Structured lipid enzymatically synthesized from fish oil rich in n-3 fatty acids (eicosapentaenoic and docosahexaenoic acid) and tricaprylin with immobilized *Rhizomucor miehei* lipase (IM 60). This structured lipid was found to improve immune system function and reduce serum cholesterol.

CONCLUDING REMARKS

The foregoing description details specific methods which can be employed to practice the present invention. Having detailed such specific methods, those skilled in the art will well enough know how to devise alternative reliable methods at arriving at the same information by using the fruits of the present invention. Thus, however detailed the foregoing may appear in text, it should not be construed as limiting the overall scope thereof; rather, the ambit of the present invention is to be determined only by the lawful construction of the appended claims. All documents cited herein are hereby expressly incorporated by reference.

What is claimed is:

1. A synthetic triacylglycerol having $R_1$, $R_2$ and $R_3$ in the form:

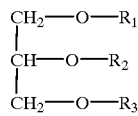

wherein at least one of $R_1$, $R_2$ and $R_3$ is a short chain fatty acid and at least one of $R_1$, $R_2$ and $R_3$ is an unsaturated fatty acid.

2. A synthetic triacylglycerol having $R_1$, $R_2$ and $R_3$ in the form:

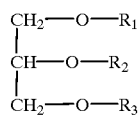

wherein at least one of $R_1$, $R_2$ and $R_3$ is a short chain fatty acid and at least one of $R_1$, $R_2$ and $R_3$ is an n-9 fatty acid.

3. A synthetic triacylglycerol having $R_1$, $R_2$ and $R_3$ in the form:

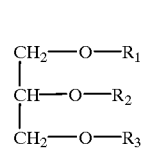

wherein two of $R_1$, $R_2$ and $R_3$ is a short chain fatty acid and one of $R_1$, $R_2$ and $R_3$ is an unsaturated fatty acid.

4. A synthetic triacylglycerol having $R_1$, $R_2$ and $R_3$ in the form:

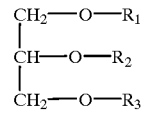

wherein one of $R_1$, $R_2$ and $R_3$ is a short chain fatty acid and each of the remaining $R_1$, $R_2$ and $R_3$ is a long chain fatty acid.

5. A method of forming a mixture comprising structured lipids comprising:
    combining triolein, caproic acid, butyric acid and a lipase under conditions which allow formation of said mixture.

6. The method of claim 5 wherein said structured lipids include at least one of any of said synthetic triacylglycerols of claims 1, 2, 3 and/or 4.

7. A method of forming a mixture comprising structured lipids comprising:
    combining a gamma-linolenic rich oil, a short or medium chain fatty acid, an unsaturated fatty acid other than said gamma-linolenic fatty acid and a lipase under conditions which allow formation of said mixture.

8. The method of claim 7 wherein said short or medium fatty acid is a medium chain fatty acid.

9. The method of claim 7 wherein said unsaturated fatty acid is an n-3 fatty acid.

10. The method of claim 7 wherein said lipase is non-specific.

11. The method of claim 7 wherein said lipase is an sn-1,3 specific lipase.

12. The method of claim 7 further comprising the step of separating at least one of said structured lipids from said mixture.

13. The method of claim 7 wherein said oil is selected from the group consisting of borage oil, primrose oil, black currant seed oil, algae oil and fungal oil.

14. Borage oil comprising at least 20 mol % saturated fatty acids and at least 3 mol % n-3 unsaturated fatty acids.

15. A structured lipid mixture comprising from 40 mol % to 70 mol % medium chain fatty acids, 0 mol % to 3 mol % saturated long chain fatty acids, and 30 mol % to 50 mol % unsaturated long chain fatty acids.

16. A method of forming a mixture comprising structured lipids comprising:
    combining an n-3 fatty acid rich oil, tricaprylin and a lipase under conditions which allow formation of said mixture.

17. The mixture formed by said method of claim 16.

18. A method of forming a mixture comprising structured lipids comprising:
    combining tricaprin or trilinolein, capric acid ethyl ester and a lipase under conditions which allow formation of said mixture.

19. The mixture formed by said method of claim 18.

20. A method of forming a mixture comprising structured lipids comprising:

combining tristearin, a medium chain fatty acid and a lipase under conditions which allow formation of said mixture.

21. The method of claim 20 wherein said medium chain fatty acid comprises:

tricaprin or tricaprylin.

22. The mixture formed by said method of claim 20.

23. A method of forming a mixture comprising structured lipids comprising:

combining trilinolein, tricaprin or caproic acid and a lipase under conditions which allow formation of said mixture.

24. The mixture formed by said method of claim 23.

25. A method of forming a mixture comprising structured lipids comprising:

combining tricaprylin, an n-3 unsaturated fatty acid and a lipase under conditions which allow formation of said mixture.

26. The mixture formed by said method of claim 25.

27. The synthetic triacylglycerol according to claim 1, wherein at least one of $R_1$ and $R_3$ is a short chain fatty acid and $R_2$ is an unsaturated fatty acid.

* * * * *